US012648801B2

(12) United States Patent
Lui et al.

(10) Patent No.: US 12,648,801 B2
(45) Date of Patent: Jun. 9, 2026

(54) ORTHOPEDIC FIXATION SYSTEMS AND METHODS OF USE THEREOF

(71) Applicant: DEPUY SYNTHES PRODUCTS, INC., Raynham, MA (US)

(72) Inventors: Eric Lui, Royersford, PA (US); Kenneth Kobayashi, Downington, PA (US); Troy Probst, Wilmington, DE (US); Daniel Cheney, Downington, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 322 days.

(21) Appl. No.: 18/096,386

(22) Filed: Jan. 12, 2023

(65) Prior Publication Data

US 2023/0225774 A1 Jul. 20, 2023

Related U.S. Application Data

(60) Provisional application No. 63/300,933, filed on Jan. 19, 2022.

(51) Int. Cl.
*A61B 17/80* (2006.01)
*A61B 17/064* (2006.01)
*A61B 17/00* (2006.01)

(52) U.S. Cl.
CPC ...... *A61B 17/8004* (2013.01); *A61B 17/0642* (2013.01); *A61B 17/808* (2013.01);
(Continued)

(58) Field of Classification Search
CPC ........ A61B 17/0642; A61B 2017/0645; A61B 2017/681; A61B 17/8004; A61B 17/808; A61B 17/809
See application file for complete search history.

(56) References Cited

U.S. PATENT DOCUMENTS 5,785,713 A 7/1998 Jobe
6,273,903 B1 * 8/2001 Wilk ...................... A61B 17/10
606/151
(Continued)

FOREIGN PATENT DOCUMENTS

EP 0826340 A2 3/1998
WO 2008129061 A1 10/2008
WO 2017139315 A1 8/2017

OTHER PUBLICATIONS

EasyClip® Osteosynthesis Compression Staples Brochure, Stryker GmbH, Bohnackerweg 1, CH—2545 Selzach Switzerland, Copyright © 2015 Stryker.

*Primary Examiner* — Larry E Waggle, Jr.
(74) *Attorney, Agent, or Firm* — Christopher L. Makay

(57) ABSTRACT

An orthopedic fixation system includes an implant transitionable between a natural shape and an insertion shape and an implant retainer. The implant includes a transition section deformable to move the implant between the natural shape and the insertion shape. The implant includes a first post and a second post protruding therefrom across the transition section. The first post and second post each include an opening therethrough, whereby, when the implant resides in the insertion shape, the opening of the first post and the opening of the second post align. The implant retainer being configured to insert in the openings of the first and second posts when the implant resides in the insertion shape such that the implant retainer interconnects the first post and second post while spanning the transition section, thereby constraining the implant in the insertion shape.

23 Claims, 51 Drawing Sheets

(52) U.S. Cl.
    CPC .. *A61B 17/809* (2013.01); *A61B 2017/00867*
           (2013.01); *A61B 2017/0645* (2013.01)

(56)                  References Cited

U.S. PATENT DOCUMENTS

| | | | |
|---|---|---|---|
| 6,685,708 | B2 | 2/2004 | Monassevitch et al. |
| 7,115,129 | B2 | 10/2006 | Heggeness |
| 7,771,457 | B2 | 8/2010 | Kay et al. |
| 7,931,679 | B2 | 4/2011 | Heggeness |
| 8,062,378 | B2 | 11/2011 | Fonte |
| 8,100,954 | B2 | 1/2012 | Kay et al. |
| 8,118,846 | B2 | 2/2012 | Either et al. |
| 8,137,351 | B2 | 3/2012 | Prandi |
| 8,409,258 | B2 | 4/2013 | Aubin et al. |
| 8,512,384 | B2 | 8/2013 | Beutter et al. |
| D691,722 | S | 10/2013 | Cheney |
| D717,951 | S | 11/2014 | Cheney et al. |
| 8,951,291 | B2 | 2/2015 | Impellizzeri |
| 8,998,903 | B2 | 4/2015 | Price et al. |
| 9,005,255 | B2 | 4/2015 | Lewis et al. |
| 9,011,507 | B2 | 4/2015 | Schelling |
| 9,060,822 | B2 | 6/2015 | Lewis et al. |
| 9,125,698 | B2 | 9/2015 | Miller |
| 9,144,443 | B2 | 9/2015 | Leither et al. |
| 9,220,546 | B2 | 12/2015 | Medoff et al. |
| 9,259,251 | B2 | 2/2016 | Kay et al. |
| 9,259,252 | B2 | 2/2016 | Kay et al. |
| 9,259,253 | B2 | 2/2016 | Kay et al. |
| 9,393,058 | B2 | 7/2016 | Aubin et al. |
| 9,408,647 | B2 | 8/2016 | Cheney |
| 9,545,278 | B2 | 1/2017 | Ducharme et al. |
| 9,597,130 | B2 | 3/2017 | Pappalardo et al. |
| 9,615,874 | B2 | 4/2017 | Orbay et al. |
| 9,730,742 | B2 | 8/2017 | Lewis et al. |
| 9,883,897 | B2 | 2/2018 | Taber |
| 9,907,588 | B2 | 3/2018 | Parekh et al. |
| 9,918,762 | B2 | 3/2018 | Federspiel et al. |
| 9,943,348 | B2 | 4/2018 | Schelling |
| 10,064,619 | B2 | 9/2018 | Palmer et al. |
| 10,070,904 | B2 | 9/2018 | Madjarov et al. |
| 10,076,372 | B2 | 9/2018 | Madjarov et al. |
| 10,123,831 | B2 | 11/2018 | Gephart |
| 10,194,959 | B2 | 2/2019 | Gephart et al. |
| 2009/0182345 | A1 | 7/2009 | Medoff et al. |
| 2010/0133316 | A1 | 6/2010 | Lizee et al. |
| 2011/0178555 | A1 | 7/2011 | Heggeness |
| 2013/0231667 | A1 | 9/2013 | Taylor et al. |
| 2015/0230843 | A1 | 8/2015 | Palmer et al. |
| 2015/0265325 | A1 | 9/2015 | Matheny |
| 2017/0007305 | A1 | 1/2017 | Hollis et al. |
| 2017/0172634 | A1 | 6/2017 | Palmer et al. |
| 2017/0181779 | A1 | 6/2017 | Either et al. |
| 2017/0196604 | A1 | 7/2017 | Hartdegen et al. |
| 2017/0209193 | A1 | 7/2017 | Hartdegen et al. |
| 2017/0281157 | A1 | 10/2017 | Hartdegen et al. |
| 2017/0303978 | A1 | 10/2017 | Palmer et al. |
| 2021/0228206 | A1 | 7/2021 | Cheney et al. |
| 2022/0015812 | A1 | 1/2022 | Cheney et al. |

\* cited by examiner

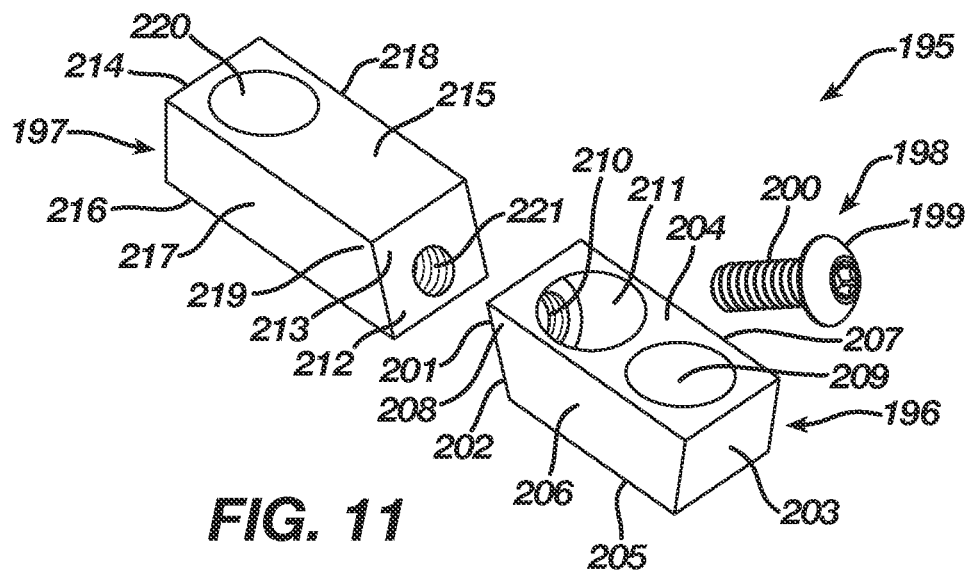
FIG. 11
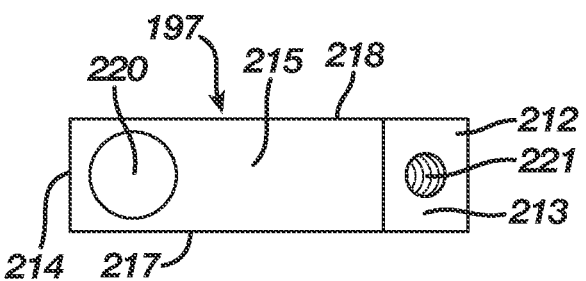
FIG. 13A
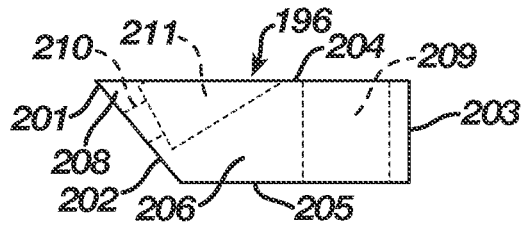
FIG. 12A
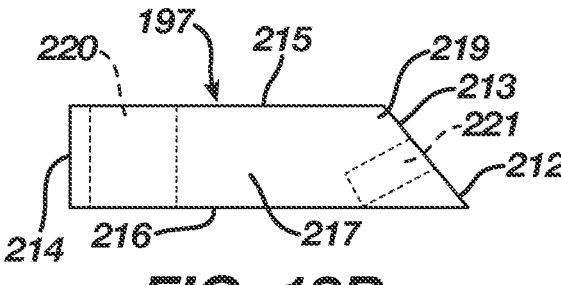
FIG. 13B
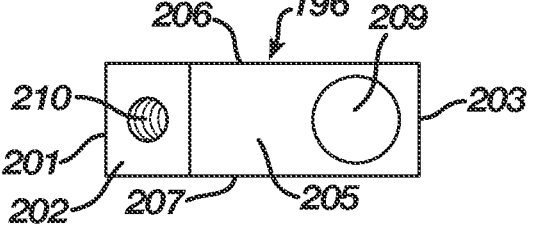
FIG. 12B
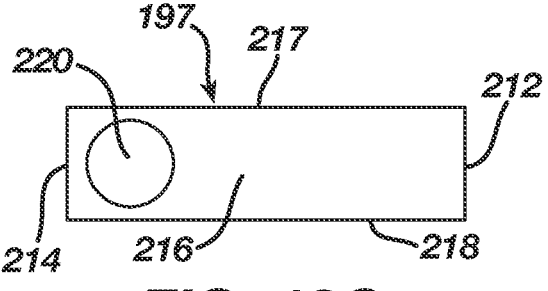
FIG. 13C
FIG. 12C

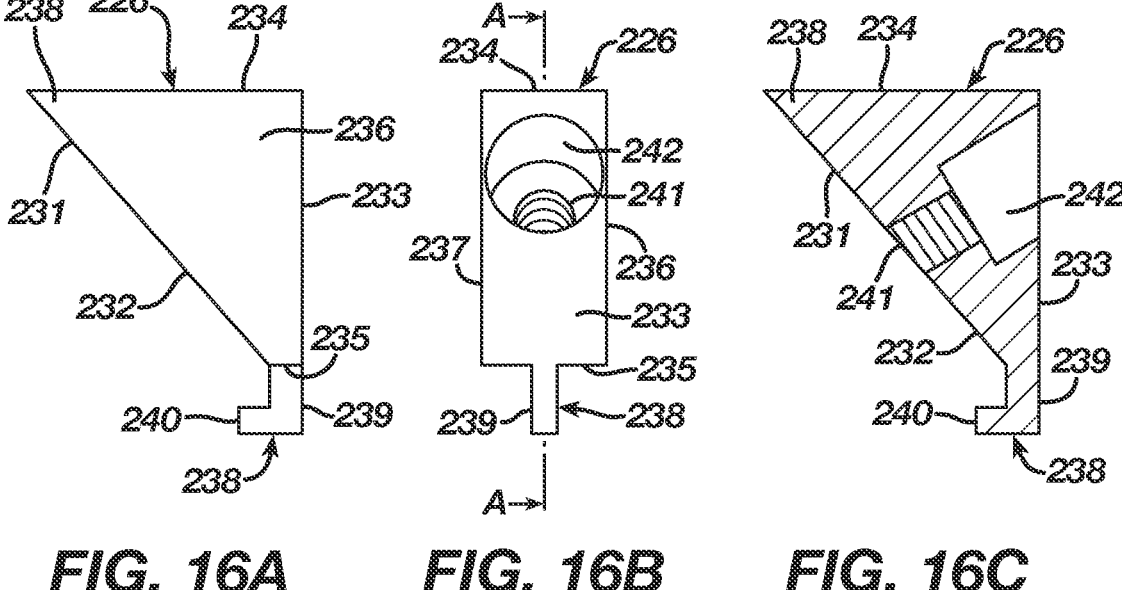
FIG. 16A          FIG. 16B          FIG. 16C
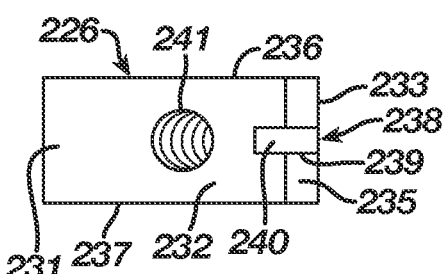
FIG. 16D

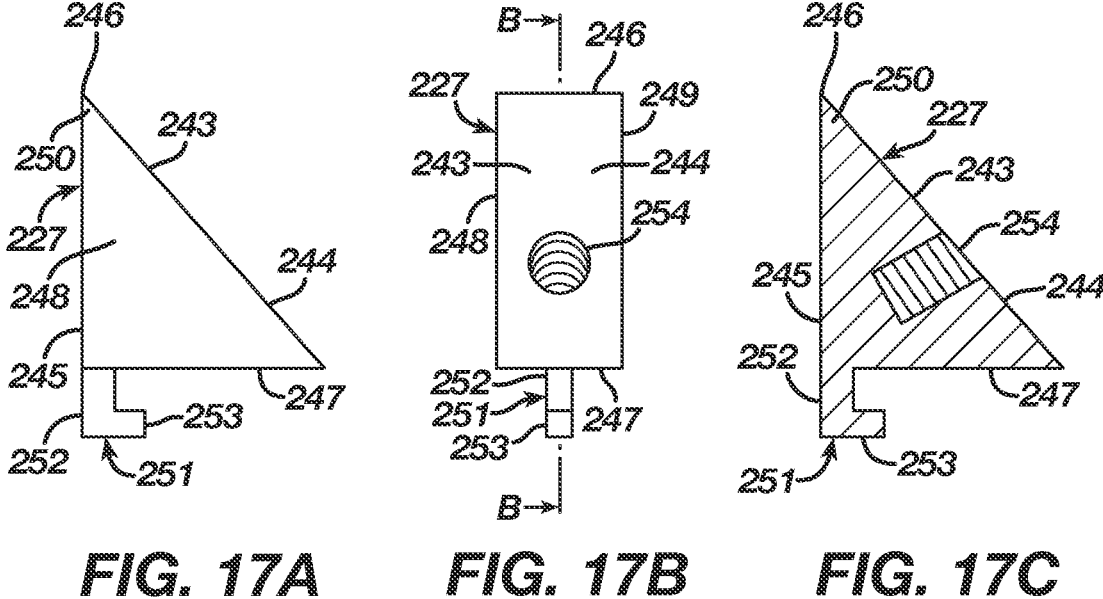
FIG. 17A          FIG. 17B          FIG. 17C
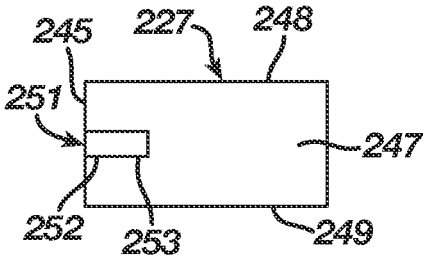
FIG. 17D

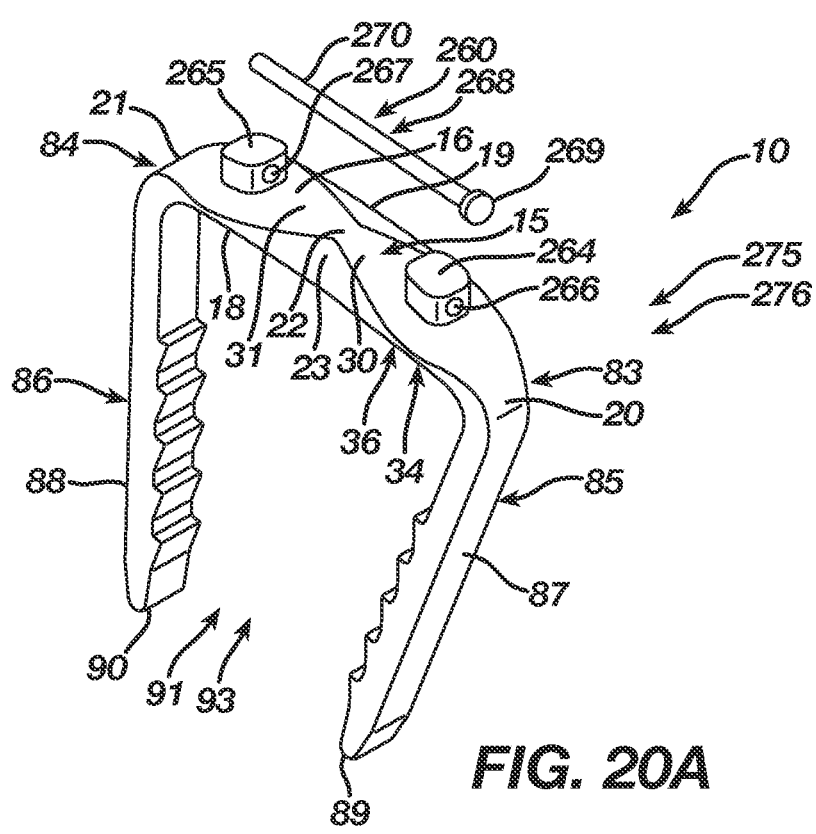
FIG. 20A
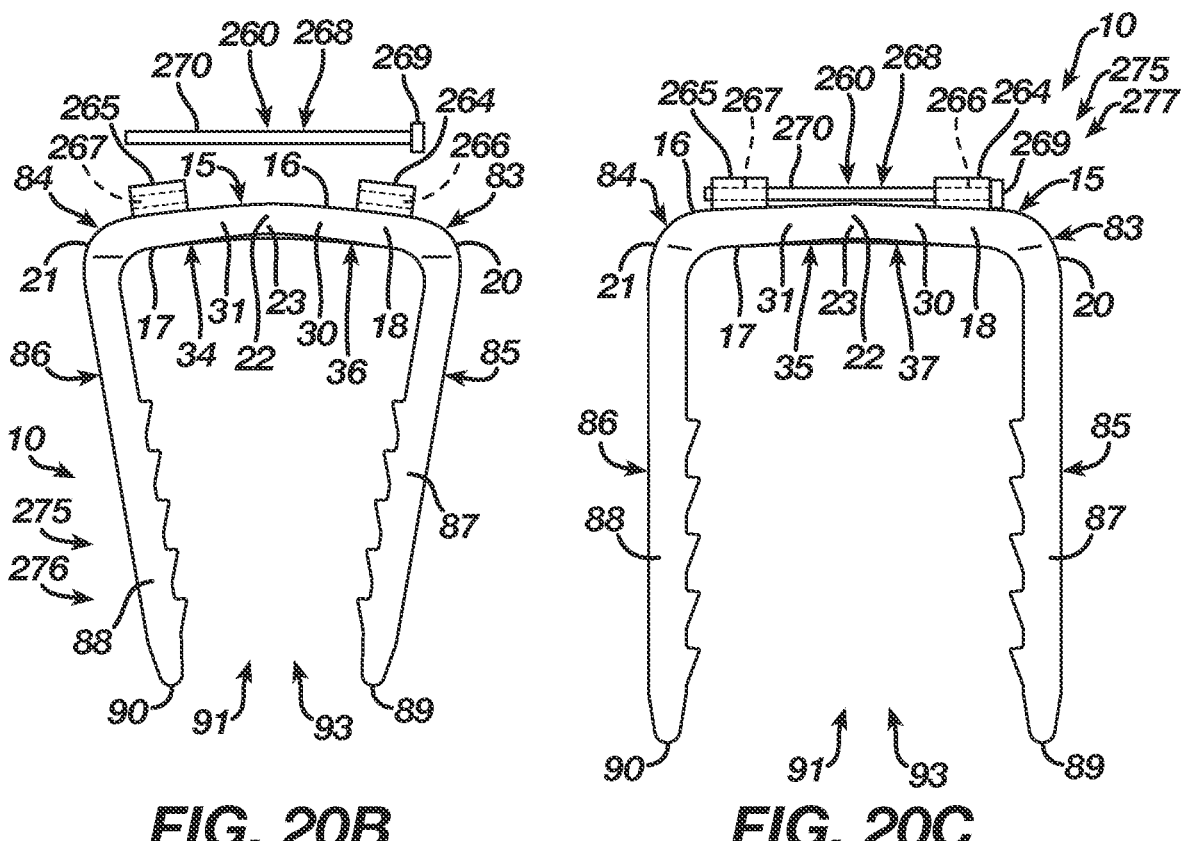
FIG. 20B          FIG. 20C

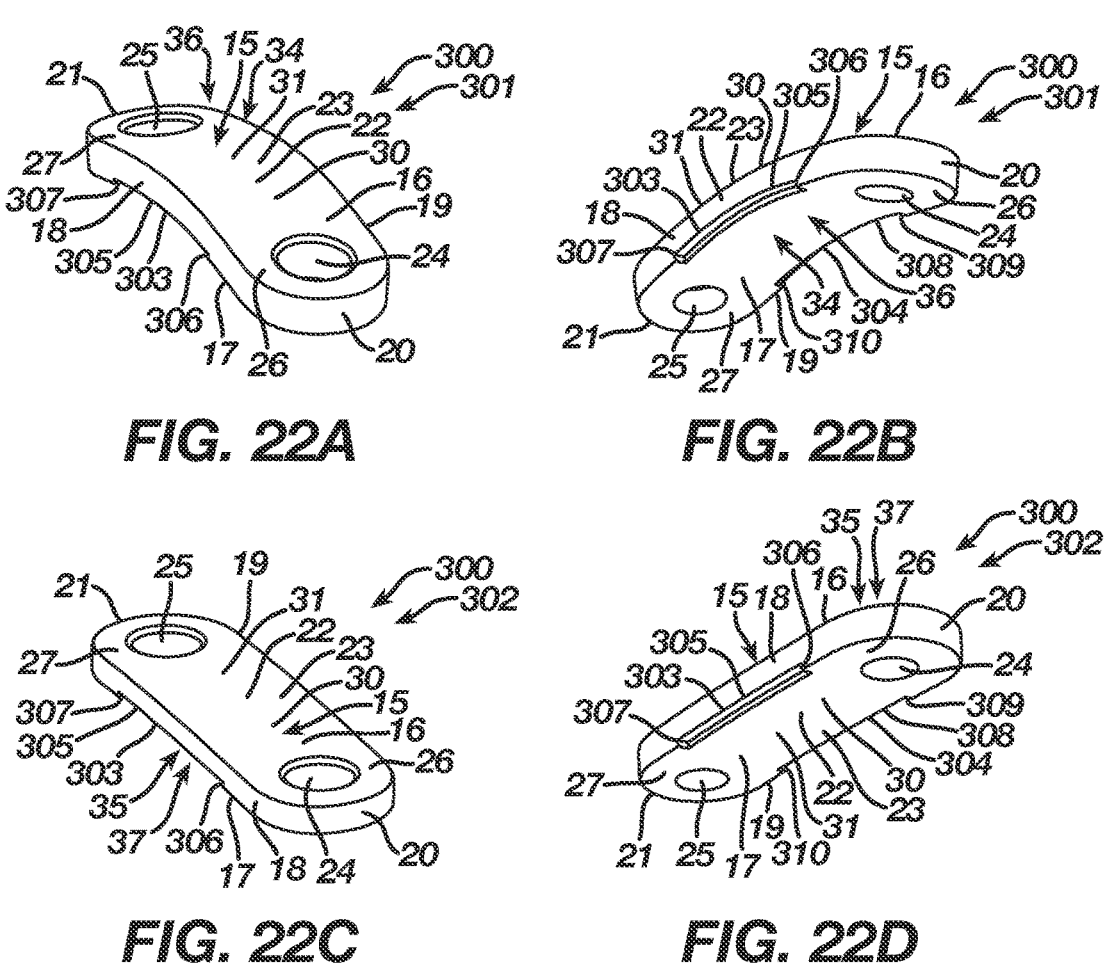
FIG. 22A          FIG. 22B
FIG. 22C          FIG. 22D
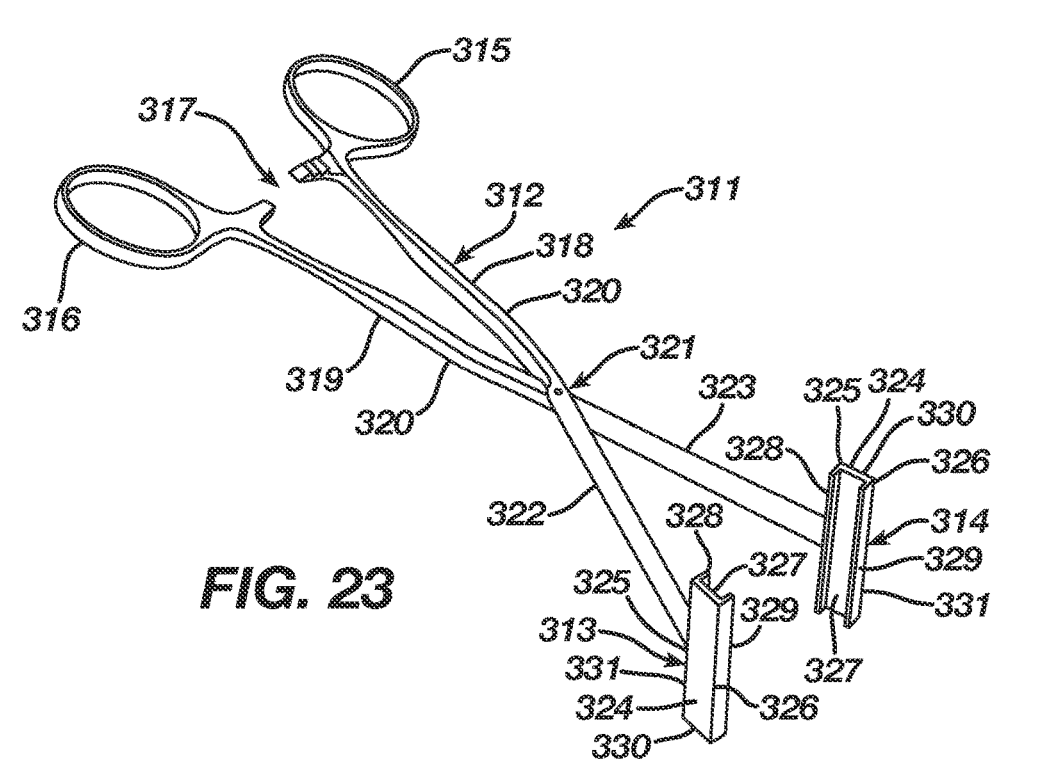
FIG. 23

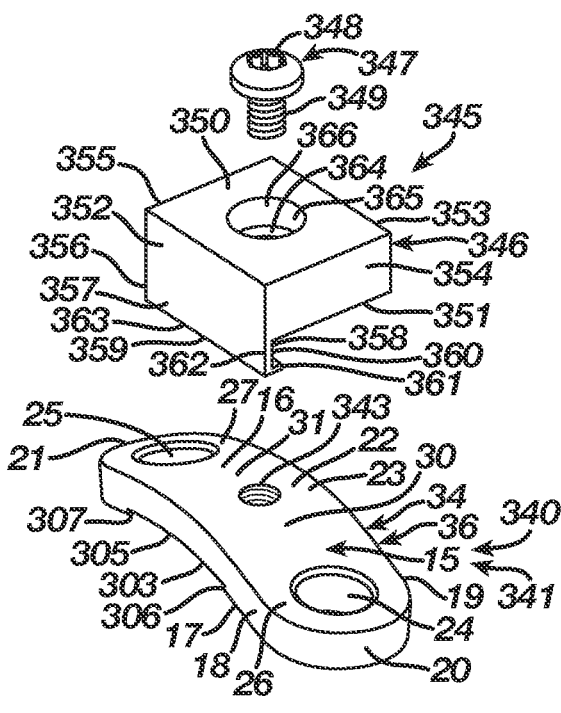
FIG. 29A
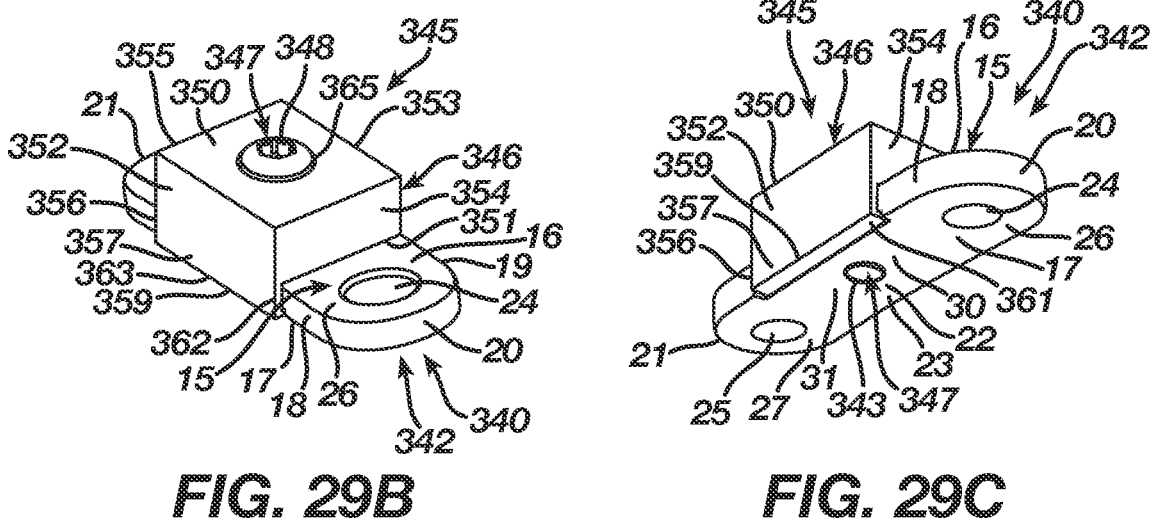
FIG. 29B          FIG. 29C

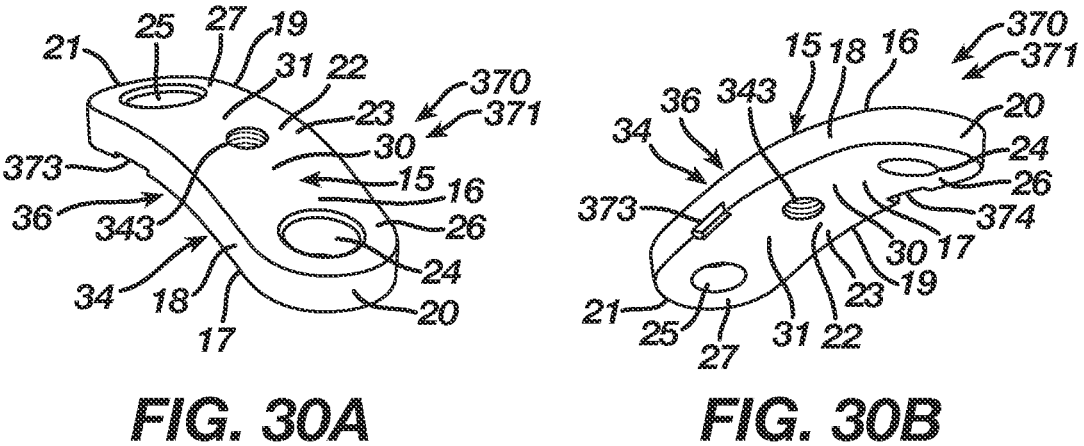
FIG. 30A
FIG. 30B
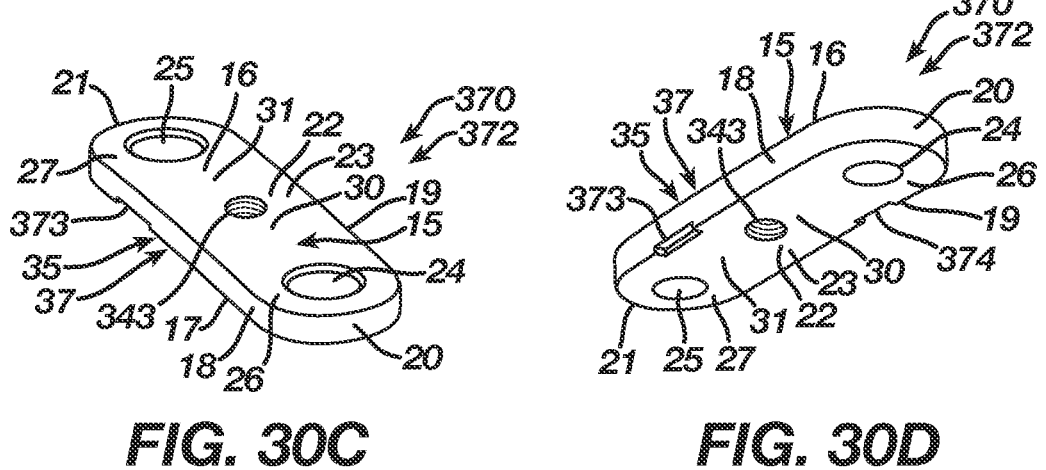
FIG. 30C
FIG. 30D

ORTHOPEDIC FIXATION SYSTEMS AND METHODS OF USE THEREOF

BACKGROUND OF THE INVENTION

1. Field of the Invention

The present invention relates generally to orthopedic fixation and, more particularly, but not way of limitation, to orthopedic fixation systems including a shape memory implant and an implant retainer.

2. Description of the Related Art

Orthopedic fixation systems commonly used in surgical procedures requiring a reattachment or fusing of bone, bones, or bone pieces include shape memory implants. The shape memory implants typically are composed of a shape memory material such as Nitinol that allows a shape memory implant to have a first final shape and the ability to transition into a second shape. Shape memory implants either can be thermally activated, in which an external heating source or body temperature would be required to activate the implants, or mechanically activated, in which a constraining instrument would be required. A shape memory implant that requires mechanical constraint stores mechanical energy due to elastic (recoverable) deformation, and then releases the stored mechanical energy when the constraining instrument is removed. In these types of implants, the implants are mechanically deformed into their second shape and maintained in their second shape by instrumentation such that, upon release from the instrumentation, the implants elastically return from their second shape to their first final shape. Although thermally activated shape memory implants may be used without a constraining instrument, thermally activated shape memory implants often include a mechanical constraint in order to prevent premature activation prior to implantation in the event of exposure to a heat source.

In surgical procedures, the elastic or thermal properties of constrained shape memory implants are used as follows. Bone, bones, or bone pieces requiring fixating are aligned in a desired orientation, and the shape memory implant, which has been mechanically deformed to the second shape, is maintained in instrumentation and then inserted across a fixation zone of the bone, bones, or bone pieces. After insertion, the shape memory implant is released from the instrumentation, whereupon the shape memory implant elastically or upon heating attempts to return from the second shape to the first final shape such that the shape memory implant delivers the mechanical energy stored therein thereby maintaining the bone, bones, or bone pieces fixated in the desired orientation. In accordance therewith, the shape memory implant, because it stores mechanical energy, continuously applies a force to the bone, bones, or bone pieces as the shape memory implant attempts to transition from the second shape to the first final shape that aids in the healing process through the affixing of the bone, bones, or bone pieces in the desired orientation.

Accordingly, although current instruments for constraining a shape memory implant in its second shape operate adequately, implant retainers that simplify removal of a shape memory implant after implantation while potentially allowing the shape memory implant to be preloaded and sterilized prior to surgery as well as a release of the shape memory implant at a bone surface thereby eliminating tamping would be beneficial.

SUMMARY OF THE INVENTION

In accordance with the present invention, an orthopedic fixation system includes an implant transitionable between a natural shape and an insertion shape and an implant retainer. A transition of the implant from the natural shape to the insertion shape stores deliverable energy, whereas a transition of the implant from the insertion shape to the natural shape delivers the stored energy. The implant retainer is configured to engage the implant when the implant resides in the insertion shape, thereby constraining the implant in the insertion shape.

The implant includes a bridge with a first end and a second end and a transition section disposed in the bridge, whereby the transition section deforms to move the implant between the natural shape and the insertion shape. The implant includes a first anchoring segment disposed at the first end of the bridge and a second anchoring segment disposed at the second end of the bridge. The implant includes a first post protruding from the bridge adjacent the transition section at a first side thereof and a second post protruding from the bridge adjacent the transition section at a second side. The first post and the second post each include an opening therethrough, whereby, when the implant resides in the insertion shape, the opening of the first post and the opening of the second post align. The first post and the second post may be removable from the bridge.

The implant retainer, which is configured to insert in the opening of the first post and the opening of the second post when the implant resides in the insertion shape, interconnects the first post and second post while spanning the transition section, thereby constraining the implant in the insertion shape. The implant retainer preferably includes a pin insertable in the opening of the first post and the opening of the second post when the implant resides in the insertion shape. The pin accordingly interconnects the first post and second post while spanning the transition section, thereby constraining the implant in the insertion shape.

A removal of the pin from the opening through the first post or the opening through the second post allows attempted transition of the implant from the insertion shape toward the natural shape. Alternatively, a cutting of the pin prior to a removal of the pin from the openings through the first post and the second post allows attempted transition of the implant from the insertion shape toward the natural shape. When the first post and the second post are removable from the bridge, a pivoting of the first post removes the pin from the opening through the second post or a pivoting of the second post removes the pin from the opening through the first post thereby allowing attempted transition of the implant from the insertion shape toward the natural shape.

The openings through the first post and the second post may comprise a bore. In accordance therewith, the pin inserts through the bore of the first post and the bore of the second post when the implant resides in the insertion shape. The pin accordingly interconnects the first post and second post while spanning the transition section, thereby constraining the implant in the insertion shape and preventing the implant from returning to the natural shape.

The first anchoring segment includes an opening configured to receive therethrough a first fixation member. Likewise, the second anchoring segment includes an opening configured to receive therethrough a second fixation member. Alternatively, the first anchoring segment includes a first leg extending from the bridge. Likewise, the second anchoring segment includes a second leg extending from the bridge.

The implant in a further embodiment includes the transition section being a first transition section located at a center section of the bridge. In addition to the first transition section, the implant includes a second transition section between the first transition section and the first anchoring segment and a third transition section between the first transition section and the second anchoring segment. The first transition section, the second transition section, and the third transition section deform to move the orthopedic implant between the natural shape and the insertion shape. Moreover, the first transition section, the second transition section, and the third transition section produce a continuous curve in the implant when the implant resides in the natural shape.

The implant in the further embodiment includes the first post protruding from the bridge between the first transition section and the second transition section and the second post protruding from the bridge between the first transition section and the third transition section. In addition to the first and second posts, the implant includes a third post protruding from the bridge between the second transition section and the first anchoring segment and a fourth post protruding from the bridge between the third transition section and the second anchoring segment. The third post and the fourth post each include an opening therethrough, whereby, when the implant resides in the insertion shape, the openings of the first post, the second post, the third post, and the fourth post align. The first post, the second post, the third post, and the fourth post may be removable from the bridge.

The implant retainer, which is configured to insert in the openings of the first post, the second post, the third post, and the fourth post when the implant resides in the insertion shape, interconnects the first post, the second post, the third post, and the fourth post while spanning the first transition section, the second transition section, and the third transition section, thereby constraining the implant in the insertion shape. The implant retainer preferably includes a pin insertable in the openings of the first post, the second post, the third post, and the fourth post when the implant resides in the insertion shape. The pin accordingly interconnects the first post, the second post, the third post, and the fourth post while spanning the first transition section, the second transition section, and the third transition section, thereby constraining the implant in the insertion shape.

The openings through the first post, the second post, the third post, and the fourth post may comprise a bore. In accordance therewith, the pin inserts through the bores of the first post, the second post, the third post, and the fourth post when the implant resides in the insertion shape. The pin accordingly interconnects the first post, the second post, the third post, and the fourth post while spanning the first transition section, the second transition section, and the third transition section, thereby constraining the implant in the insertion shape and preventing the implant from returning to the natural shape.

A removal of the pin from the openings through the fourth post, the second post, and the first post or a removal of the pin from the openings through the third post, the first post, and the second post allows attempted transition of the implant from the insertion shape toward the natural shape. Alternatively, the pin may be removed progressively from the openings through the fourth post, the second post, and the first post or the openings through the third post, the first post, and the second post. More particularly, a removal of the pin from the opening through the fourth post allows attempted transition of the implant from the insertion shape toward a first intermediate shape, a removal of the pin from the opening through the second post allows attempted transition of the implant from the first intermediate shape toward a second intermediate shape, and a removal of the pin from the opening through the first post allows attempted transition of the implant from the second intermediate shape toward the natural shape. Conversely, a removal of the pin from the opening through the third post allows attempted transition of the implant from the insertion shape toward a first intermediate shape, a removal of the pin from the opening through the first post allows attempted transition of the implant from the first intermediate shape toward a second intermediate shape, and a removal of the pin from the opening through the second post allows attempted transition of the implant from the second intermediate shape toward the natural shape.

The implant in another embodiment includes a first transition section, a second transition section, and a third transition section disposed along the bridge between the first anchoring segment and the second anchoring segment. The first transition section, the second transition section, and the third transition section deform to move the implant between the natural shape and the insertion shape. Moreover, the first transition section, the second transition section, and the third transition section produce a continuous curve in the implant when the implant resides in the natural shape.

The implant includes a first post protruding from the bridge between the first anchoring segment and the first transition section, a second post protruding from the bridge between the first transition section and the second transition section, a third post protruding from the bridge between the second transition section and the third transition section, and a fourth post protruding from the bridge between the third transition section and the second anchoring segment. The first post, the second post, the third post, and the fourth post each include an opening therethrough, whereby, when the implant resides in the insertion shape, the openings of the first post, the second post, the third post, and the fourth post align. The first post, the second post, the third post, and the fourth post may be removable from the bridge.

The implant retainer, which is configured to insert in the openings of the first post, the second post, the third post, and the fourth post when the implant resides in the insertion shape, interconnects the first post, the second post, the third post, and the fourth post while spanning the first transition section, the second transition section, and the third transition section, thereby constraining the implant in the insertion shape. The implant retainer preferably includes a pin insertable in the openings of the first post, the second post, the third post, and the fourth post when the implant resides in the insertion shape. The pin accordingly interconnects the first post, the second post, the third post, and the fourth post while spanning the first transition section, the second transition section, and the third transition section, thereby constraining the implant in the insertion shape.

The openings through the first post, the second post, the third post, and the fourth post may comprise a bore. In accordance therewith, the pin inserts through the bores of the first post, the second post, the third post, and the fourth post when the implant resides in the insertion shape. The pin accordingly interconnects the first post, the second post, the third post, and the fourth post while spanning the first transition section, the second transition section, and the third transition section, thereby constraining the implant in the insertion shape and preventing the implant from returning to the natural shape.

A removal of the pin from the openings through the fourth post, the third post, and the second post allows attempted transition of the implant from the insertion shape toward the natural shape. Alternatively, the pin may be removed progressively from the fourth post, the third post, and the second post. More particularly, a removal of the pin from the opening through the fourth post allows attempted transition of the implant from the insertion shape toward a first intermediate shape, a removal of the pin from the opening through the third post allows attempted transition of the implant from the first intermediate shape toward a second intermediate shape, and a removal of the pin from the opening through the second post allows attempted transition of the implant from the second intermediate shape toward the natural shape.

It is therefore an object of the present invention to provide an orthopedic fixation system with an implant transitionable between a natural shape and an insertion shape.

It is another object of the present invention to provide the orthopedic fixation system with an implant retainer configured to engage with the orthopedic implant such the implant retainer constrains the orthopedic implant in the insertion shape.

It is a further object of the present invention to provide an orthopedic fixation system with an implant configured to progressively deliver energy to a bone, bones, or bone pieces.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF DRAWINGS

FIG. 11 is a top isometric view illustrating an implant retainer according to a fifth embodiment.

FIG. 12A is a top view illustrating a first retention block of the implant retainer according to the fifth embodiment.

FIG. 12B is a side view illustrating the first retention block of the implant retainer according to the fifth embodiment.

FIG. 12C is a bottom view illustrating the first retention block of the implant retainer according to the fifth embodiment.

FIG. 13A is a top view illustrating a second retention block of the implant retainer according to the fifth embodiment.

FIG. 13B is a side view illustrating the second retention block of the implant retainer according to the fifth embodiment.

FIG. 13C is a bottom view illustrating the second retention block of the implant retainer according to the fifth embodiment.

FIG. 16A is a side view illustrating a first retention block of the implant retainer according to the sixth embodiment.

FIG. 16B is a rear view illustrating the first retention block of the implant retainer according to the sixth embodiment.

FIG. 16C is a cross-sectional view taken along line A-A of FIG. 16B illustrating the first retention block of the implant retainer according to the sixth embodiment.

FIG. 16D is a bottom view illustrating the first retention block of the implant retainer according to the sixth embodiment.

FIG. 17A is a side view illustrating a second retention block of the implant retainer according to the sixth embodiment.

FIG. 17B is a front view illustrating the second retention block of the implant retainer according to the sixth embodiment.

FIG. 17C is a cross-sectional view taken along line B-B of FIG. 17B illustrating the second retention block of the implant retainer according to the sixth embodiment.

FIG. 17D is a bottom view illustrating the second retention block of the implant retainer according to the sixth embodiment.

FIG. 20A is a top isometric view illustrating the implant retainer according to the seventh embodiment and an orthopedic implant according to a sixth embodiment in a natural shape.

FIG. 20B is a side view illustrating the implant retainer according to the seventh embodiment and the orthopedic implant according to the sixth embodiment in the natural shape.

FIG. 20C is side view illustrating the implant retainer according to the seventh embodiment and the orthopedic implant according to the sixth embodiment in the insertion shape forming the orthopedic fixation system.

FIG. 22A is a top isometric view illustrating an orthopedic implant according to a seventh embodiment in a natural shape.

FIG. 22B is a bottom isometric view illustrating the orthopedic implant according to the seventh embodiment in the natural shape.

FIG. 22C is a top isometric view illustrating the orthopedic implant according to the seventh embodiment in an insertion shape.

FIG. 22D is a bottom isometric view illustrating the orthopedic implant according to the seventh embodiment in the insertion shape.

FIG. 23 is an isometric view illustrating an implant retainer according to an eighth embodiment.

FIG. 29A is a top isometric view illustrating the implant retainer according to the alternative of the eighth embodiment and the orthopedic implant according to the alternative of the seventh embodiment in the natural shape.

FIG. 29B is a top isometric view illustrating the implant retainer according to the alternative of the eighth embodiment and the orthopedic implant according to the alternative of the seventh embodiment in the insertion shape forming the orthopedic fixation system.

FIG. 29C is a bottom isometric view illustrating the implant retainer according to the alternative of the eighth embodiment and the orthopedic implant according to the alternative of the seventh embodiment in the insertion shape forming the orthopedic fixation system.

FIG. 30A is a top isometric view illustrating an orthopedic implant according to an alternative of the seventh embodiment in a natural shape.

FIG. 30B is a bottom isometric view illustrating the orthopedic implant according to the alternative of the seventh embodiment in the natural shape.

FIG. 30C is a top isometric view illustrating the orthopedic implant according to the alternative of the seventh embodiment in an insertion shape.

FIG. 30D is a bottom isometric view illustrating the orthopedic implant according to the alternative of the seventh embodiment in the insertion shape.

DETAILED DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

An orthopedic fixation system 10 according to the present invention includes an orthopedic implant selected from a group of orthopedic implants described more fully herein. Each orthopedic implant transitions between a natural shape and an insertion shape. The orthopedic fixation system 10 according to the present invention further includes an implant retainer selected from a group of implant retainers described more fully herein. Each implant retainer is configured for engagement with an orthopedic implant whereby the implant retainer constrains the orthopedic implant in the insertion shape.

Figure 1A:
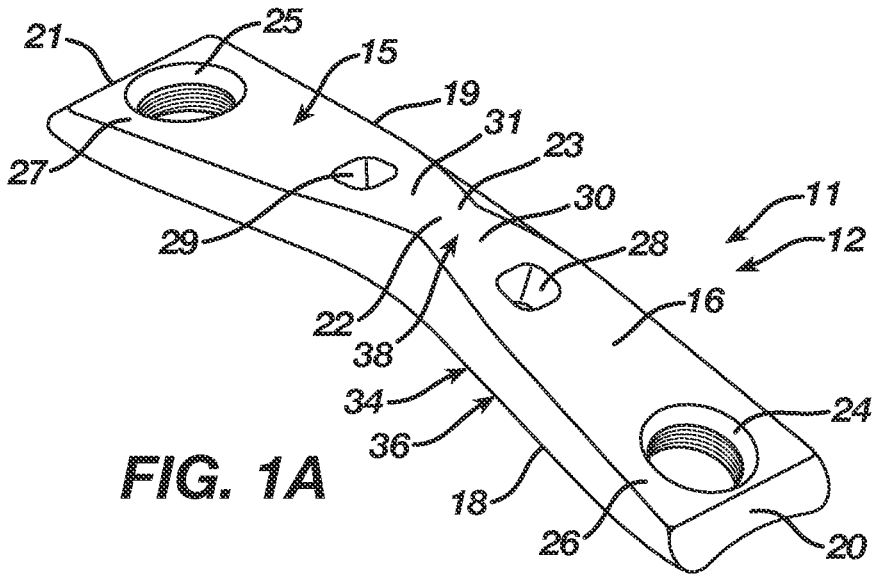
FIG. 1A is a top isometric view illustrating an orthopedic implant according to a first embodiment in a natural shape.
Figure 1B:
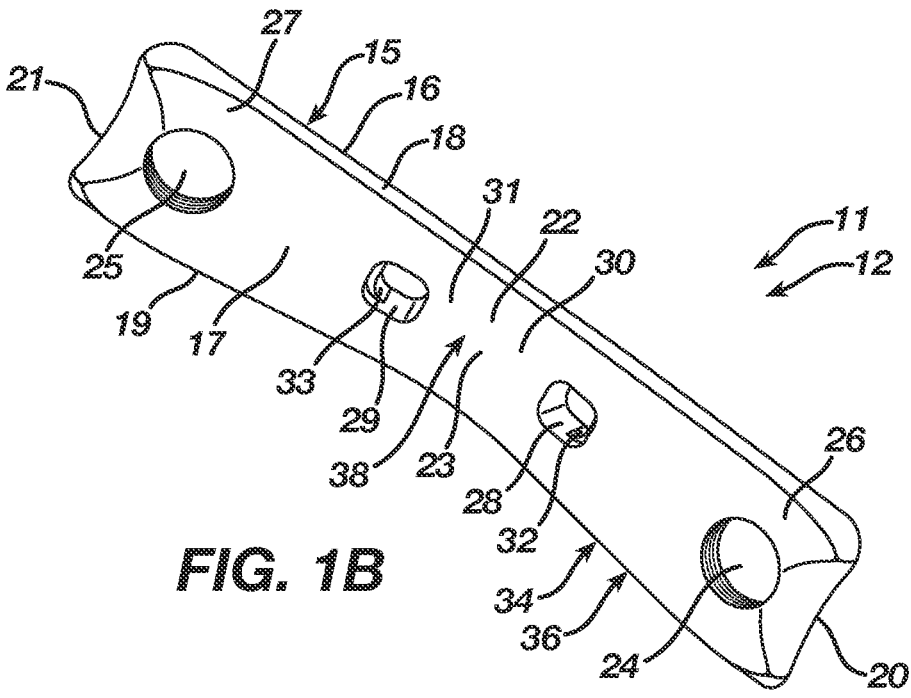
FIG. 1B is a bottom isometric view illustrating the orthopedic implant according to the first embodiment in the natural shape.
Figure 1C:
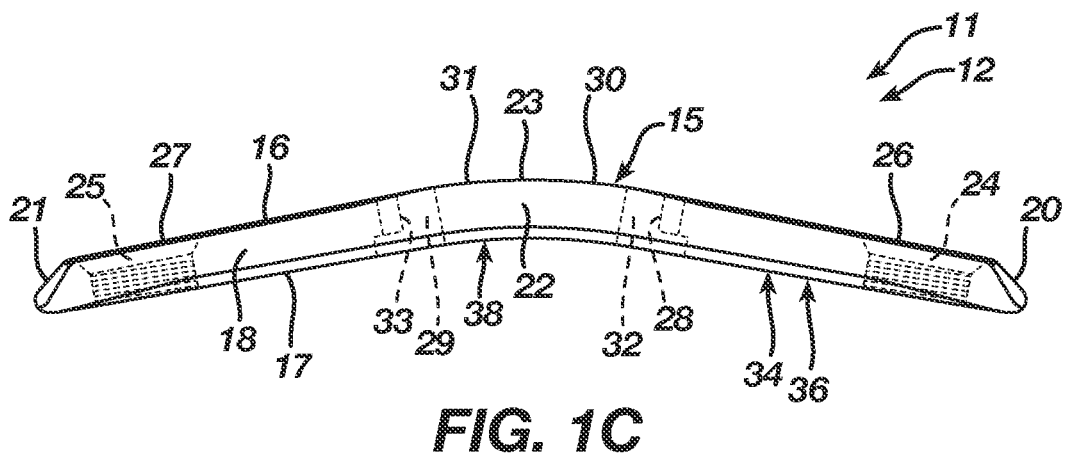
FIG. 1C is an elevation view illustrating the orthopedic implant according to the first embodiment in the natural shape.
Figure 1D:
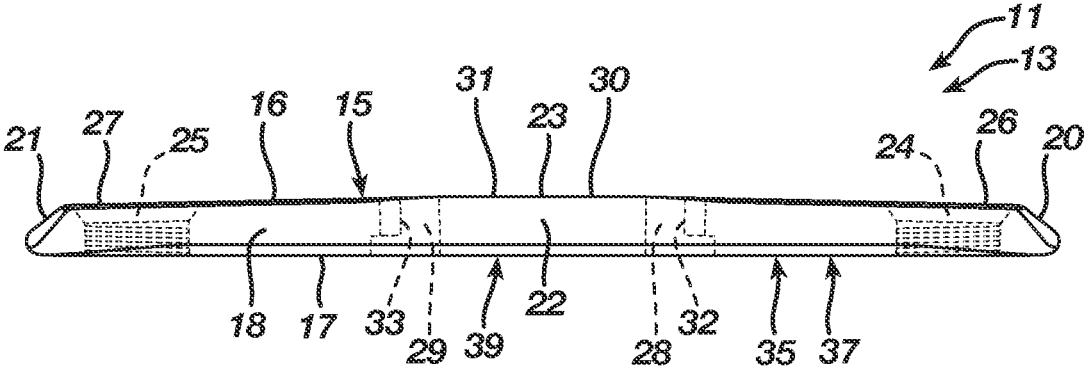
FIG. 1D is an elevation view illustrating the orthopedic implant according to the first embodiment in an insertion shape.

FIGS. 1A-1C illustrate an orthopedic implant 11 according to a first embodiment in a natural shape 12, whereas FIG. 1D illustrates the orthopedic implant 11 in an insertion shape 13. The implant 11 in the first embodiment may be manufactured from a shape memory material with superelastic or temperature dependent properties (e.g., Nitinol) such that the implant 11 transitions between the natural shape 12 and the insertion shape 13. The implant 11 when deformed from the natural shape 12 to the insertion shape 13 stores energy deliverable to bone, bones, or bone pieces. In accordance with its manufacture from shape memory material, the implant 11 begins in the natural shape 12, is transitionable to the insertion shape 13, and, once implanted in bone, bones, or bone pieces, attempts to transition from the insertion shape 13 to the natural shape 12 whereby the implant 11 delivers the energy stored therein to the bone, bones, or bone pieces in order to affix the bone, bones, or bone pieces and promote a healing thereof. In the first embodiment, attempted transition of the implant 11 from the insertion shape 13 to the natural shape 12 continuously compresses the bone, bones, or bone pieces to promote fusion thereof.

The implant 11 includes a bridge 15 with upper and lower surfaces 16 and 17, first and second sides 18 and 19, and first and second ends 20 and 21. The implant 11 includes a transition section 22 located at a center section 23 of the implant 11 and thus the bridge 15. The implant 11, and thus the bridge 15, includes a first opening 24 extending therethrough from the upper surface 16 to the lower surface 17 whereby the first opening 24 is located adjacent the first end 20 of the bridge 15 to provide the implant 11 and thus the bridge 15 with an anchoring segment 26. Likewise, the implant 11, and thus the bridge 15, includes a second opening 25 extending therethrough from the upper surface 16 to the lower surface 17 whereby the second opening 25 is located adjacent the second end 21 of the bridge 15 to provide the implant 11 and thus the bridge 15 with an anchoring segment 27. The first and second openings 24 and 25 receive therethrough anchoring members in the form of biocompatible locking, non-locking, or self-tapping bone screws in order to facilitate a securing of the implant 11 at the first and second anchoring segments 26 and 27 with bone, bones, or bone pieces whereby the bridge 15 between the first and second openings 24 and 25 traverses a fixation zone of the bone, bones, or bone pieces. In accordance therewith, the implant 11, after its insertion and attempted transition from the insertion shape 13 to the natural shape 12, delivers energy to the bone, bones, or bone pieces at the fixation zone. Although the first and second openings 24 and 25 of the implant 11 primarily operate to receive therethrough anchoring members, the first and second openings 24 and 25 may receive therein respectively drill guides. The drill guides facilitate a drilling of holes in the bone, bones, or bone pieces that assist in inserting anchoring members through the first and second openings 24 and 25 and into the bone, bones, or bone pieces. The first and second openings 24 and 25 in the first embodiment include threads that facilitate engagement of the first and second openings 24 and 25 with anchoring members or the drill guides.

The implant 11, and thus the bridge 15, includes a first securing feature in the form of a first aperture 28 extending therethrough from the upper surface 16 to the lower surface 17 whereby the first aperture 28 is located adjacent the transition section 22 at a first side 30 thereof. The implant 11, and thus the bridge 15, includes a catch 32 protruding into the first aperture 28, which, in the first embodiment, is located at an exterior side of the first aperture 28. Similarly, the implant 11, and thus the bridge 15, includes a second securing feature in the form of a second aperture 29 extending therethrough from the upper surface 16 to the lower surface 17 whereby the second aperture 29 is located adjacent the transition section 22 at a second side 31 thereof. The implant 11, and thus the bridge 15, includes a catch 33 protruding into the second aperture 29, which, in the first embodiment, is located at an exterior side of the second aperture 29. While the catch 32 and the catch 33 in the first embodiment protrude respectively into the first aperture 28 and the second aperture 29 at the exterior sides thereof, the implant 11, and thus the bridge 15, in an alternative illustrated in FIGS. 1E-1F, includes the catch 32 protruding into the first aperture 28 at an interior side thereof and the catch 33 protruding into the second aperture 29 at an interior side thereof. The first aperture 28 and the catch 32 thereof and the second aperture 29 and the catch 33 thereof provide points of engagement for the implant 11 with an implant retainer.

The regular inherent shape of the implant 11, as illustrated in FIGS. 1A-1C, is the natural shape 12 where the transition section 22 locates the bridge 15 in a natural form 34 consisting of a closed or angular profile whereby the first and second ends 20 and 21 reside at a first distance 36. Nevertheless, as illustrated in FIG. 1D, the implant 11 is deformable under the action of superelasticity or temperature dependent shape memory to the insertion shape 13 where the transition section 22 deforms to store energy while also moving the bridge 15 from the natural form 34 to an insertion form 35 which is an open or substantially linear profile whereby the first and second ends 20 and 21 reside at a second distance 37 that is greater than the first distance 36. When the implant 11 resides in the natural shape 12 with the bridge 15 in the natural form 34, the first aperture 28 and the second aperture 29 reside spaced apart at a first distance 38. Alternatively, when the implant 11 resides in the insertion shape 13 with the bridge 15 in the insertion form 35, the first aperture 28 and the second aperture 29 reside spaced apart at a second distance 39 that is greater than the first distance first distance 38. Since the insertion shape 13 is not the regular inherent shape of the implant 11, the bridge 15 typically is mechanically constrained using an implant retainer whereby the implant retainer maintains the bridge 15 in the insertion form 35. In particular, the implant retainer inserts into the first and second apertures 28 and 29 and engages the catches 32 and 33 such that the implant retainer holds the bridge 15, resulting in the implant retainer constraining the deformed transition section 22 in order to maintain the implant 11 in the insertion shape 13 with the bridge 15 in the insertion form 35. After implantation into bone, bones, or bone pieces and a release of the implant retainer, including if necessary a heating of the implant 11, the implant 11 delivers the energy stored in the transition section 22 whereby the implant 11 attempts to transition from the insertion shape 13 to the natural shape 12 through an attempted transition of the bridge 15 from the insertion form 35 to the natural form 34 such that the implant 11 affixes the bone, bones, or bone pieces through an application of a compressive force thereto.

Figure 2A:
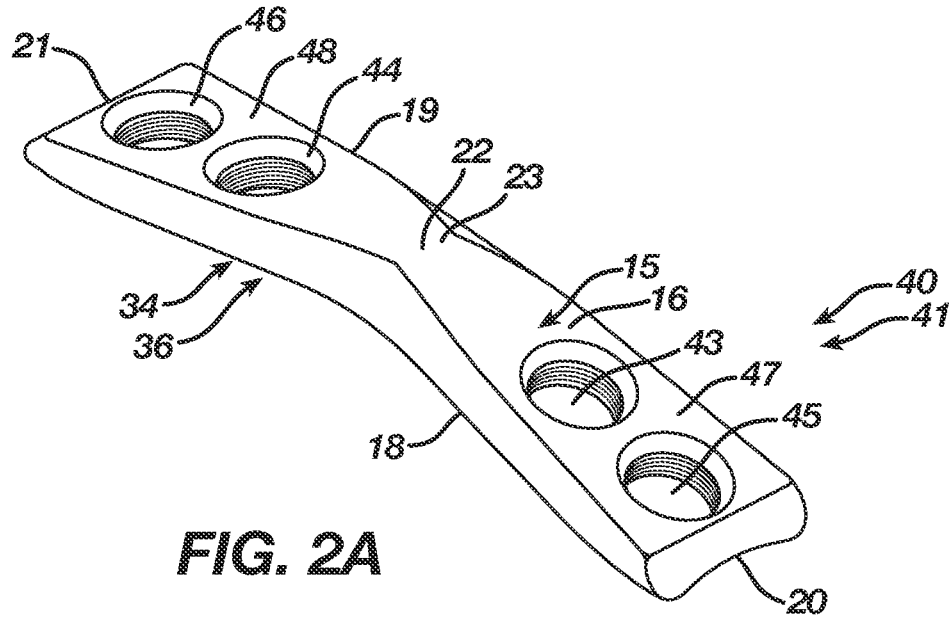
FIG. 2A is a top isometric view illustrating an orthopedic implant according to a second embodiment in a natural shape.
Figure 2B:
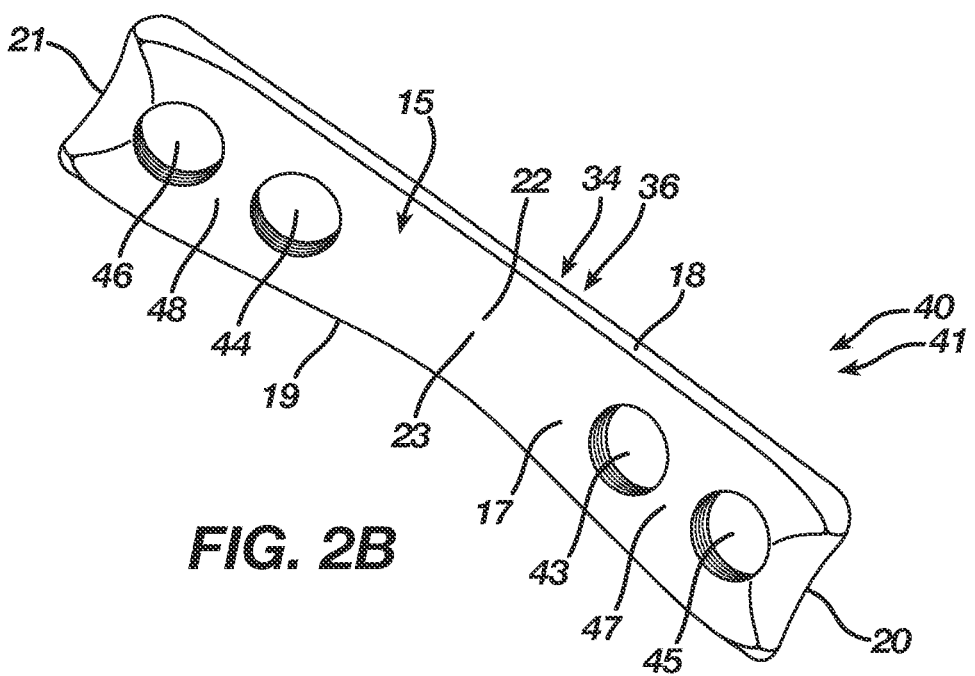
FIG. 2B is a bottom isometric view illustrating the orthopedic implant according to the second embodiment in the natural shape.
Figure 2C:
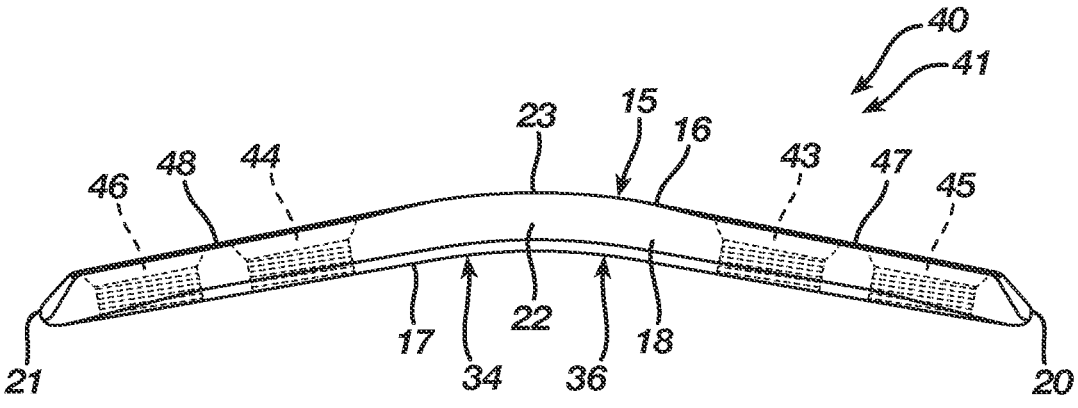
FIG. 2C is an elevation view illustrating the orthopedic implant according to the second embodiment in the natural shape.
Figure 2D:
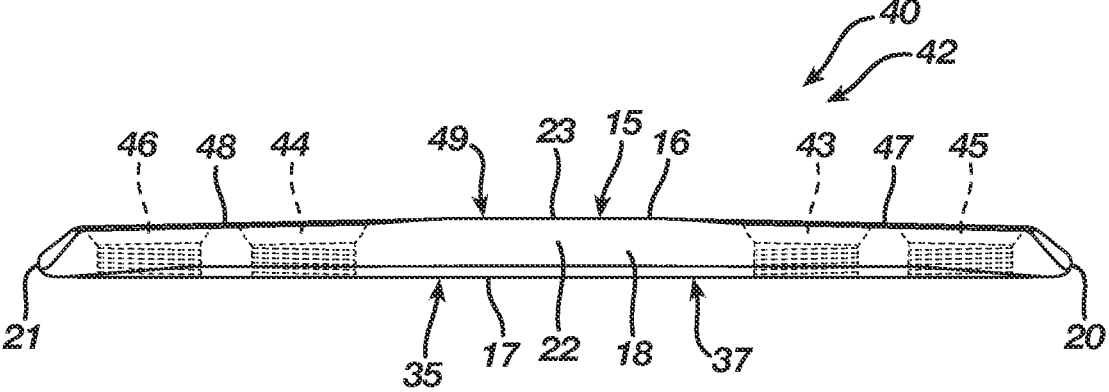
FIG. 2D is an elevation view illustrating the orthopedic implant according to the second embodiment in an insertion shape.

FIGS. 2A-2C illustrate an orthopedic implant 40 according to a second embodiment in a natural shape 41, whereas FIG. 2D illustrates the orthopedic implant 40 in an insertion shape 42. The implant 40 is substantially similar in design and operation relative to the implant 11 according to the first embodiment such that, for the sake of brevity, only differences therebetween will be described herein. Moreover, one of ordinary skill in the art will recognize that like parts of the implant 40 labeled with like numerals of the implant 11 incorporate a design and function as previously set forth in the detailed description of the implant 11 according to the first embodiment. The implant 11 includes the first opening 24 at the anchoring segment 26 and the second opening 25 at the anchoring segment 27, whereas the implant 40 includes first and third openings 43 and 45 at an anchoring segment 47 and second and fourth openings 44 and 46 at an anchoring segment 48 that receive additional drill guides therein or anchoring members therethrough in the form of biocompatible locking, non-locking, or self-tapping bone screws in order to more securely affix the implant 40 to bone, bones, or bone pieces. While the implant 11 includes the first and second apertures 28 and 29 and the catches 32 and 33 thereof in order to facilitate a securing of the implant 11 with an implant retainer, the implant 40 eliminates the first and second apertures 28 and 29 and the catches 32 and 33 in favor of an implant retainer, which will be described more fully herein, configured to engage drill guides coupled with the implant 40 at the first and second openings 43 and 44 thereof. In order for the implant retainer to engage drill guides coupled with the implant 40 at the first and second openings 43 and 44 thereof, the implant 40 when residing in the insertion shape 42 includes a known distance 49 between the first and second openings 43 and 44.

Figure 3A:
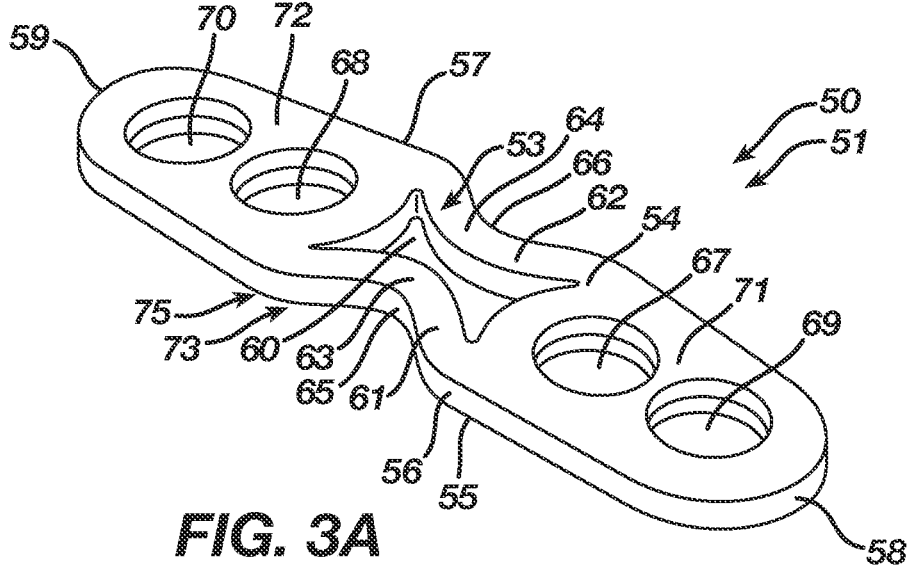
FIG. 3A is a top isometric view illustrating an orthopedic implant according to a third embodiment in a natural shape.
Figure 3B:
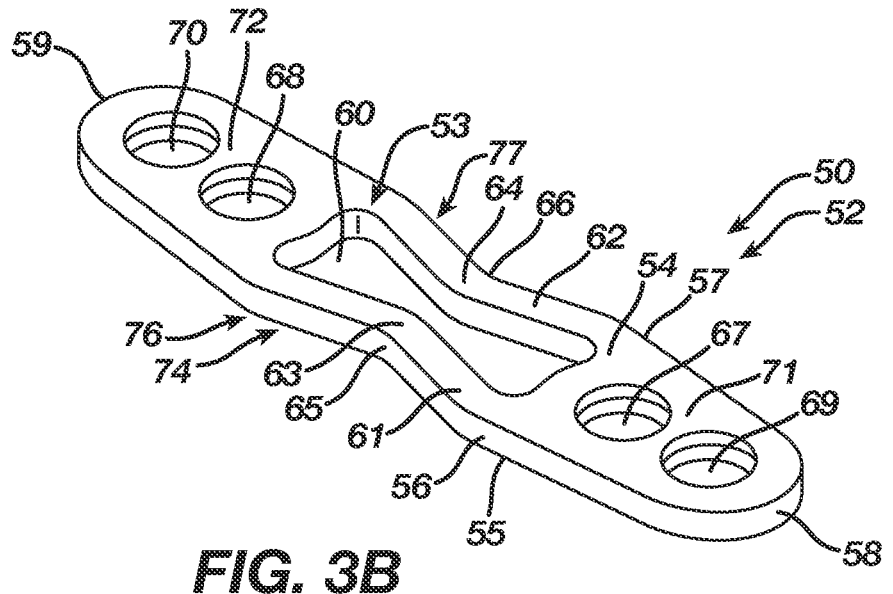
FIG. 3B is a top isometric view illustrating the orthopedic implant according to the third embodiment in an insertion shape.

FIG. 3A illustrates an orthopedic implant 50 according to a third embodiment in a natural shape 51, whereas FIG. 3B illustrates the orthopedic implant 50 in an insertion shape 52. The implant 50 in the third embodiment may be manufactured from a shape memory material with superelastic or temperature dependent properties (e.g., Nitinol) such that the implant 50 transitions between the natural shape 51 and the insertion shape 52. The implant 50 when deformed from the natural shape 51 to the insertion shape 52 stores energy deliverable to bone, bones, or bone pieces. In accordance with its manufacture from shape memory material, the implant 50 begins in the natural shape 51, is transitionable to the insertion shape 52, and, once implanted in bone, bones, or bone pieces, attempts to transition from the insertion shape 52 to the natural shape 51 whereby the implant 50 delivers the energy stored therein to the bone, bones, or bone pieces in order to affix the bone, bones, or bone pieces and promote a healing thereof. In the third embodiment, attempted transition of the implant 50 from the insertion shape 52 to the natural shape 51 continuously compresses the bone, bones, or bone pieces to promote fusion thereof.

The implant 50 includes a bridge 53 with upper and lower surfaces 54 and 55, first and second sides 56 and 57, and first and second ends 58 and 59. The implant 50 in the bridge 53 thereof defines a slot 60 that results in the bridge 50 being divided into a first bridge member 61 and a second bridge member 62. The implant 50 in the first bridge member 61 of the bridge 53 includes a transition section 63 located along a center section 65 of the implant 50 and thus the first bridge member 61 of the bridge 53. The implant 50 in the second bridge member 62 of the bridge 53 includes a transition section 64 located along a center section 66 of the implant 50 and thus the second bridge member 62 of the bridge 53. The implant 50, and thus the bridge 53, includes first and third openings 67 and 69 extending therethrough from the upper surface 54 to the lower surface 55 whereby the first and third openings 67 and 68 are located adjacent the first end 58 of the bridge 53 to provide the implant 50 and thus the bridge 53 with an anchoring segment 71. Likewise, the implant 50, and thus the bridge 53, includes second and fourth openings 68 and 70 extending therethrough from the upper surface 54 to the lower surface 55 whereby the second and fourth openings 68 and 70 are located adjacent the second end 59 of the bridge 53 to provide the implant 50 and thus the bridge 53 with an anchoring segment 72. The first, second, third, and fourth openings 67-70 receive therethrough anchoring members in the form of biocompatible locking, non-locking, or self-tapping bone screws in order to facilitate a securing of the implant 50 at the first and second anchoring segments 71 and 72 with bone, bones, or bone pieces whereby the bridge 53 between the first and second openings 67 and 68 traverses a fixation zone of the bone, bones, or bone pieces. In accordance therewith, the implant 50, after its insertion and attempted transition from the insertion shape 52 to the natural shape 51, delivers energy to the bone, bones, or bone pieces at the fixation zone. Although the first, second, third, and fourth openings 67-70 of the implant 50 primarily operate to receive therethrough anchoring members, the first, second, third, and fourth openings 67-70 may receive therein respectively drill guides. The drill guides facilitate a drilling of holes in the bone, bones, or bone pieces that assist in inserting anchoring members through the first, second, third, and fourth openings 67-70 and into the bone, bones, or bone pieces. The first, second, third, and fourth openings 67-70 in the third embodiment include threads that facilitate engagement of the first, second, third, and fourth openings 67-70 with anchoring members or the drill guides.

The regular inherent shape of the implant 50, as illustrated in FIGS. 3A, is the natural shape 51 where the transition sections 63 and 64 locate the bridge 53 and thus the first bridge member 61 and the second bridge member 62 in a natural form 73. In the natural form 73, the transition sections 63 and 64, respectively, contract the first and second bridge members 61 and 62 whereby the first and second bridge members 61 and 62 move linearly toward each other such that the first and second ends 58 and 59 move linearly to reside at a first distance 75. Nevertheless, as illustrated in FIG. 3B, the implant 50 is deformable under the action of superelasticity or temperature dependent shape memory to the insertion shape 52 where the transition sections 63 and 64 deform to store energy while also moving the bridge 53 and thus the first bridge member 61 and the second bridge member 62 from the natural form 73 to an insertion form 74. In the insertion form 74, the transition sections 63 and 64, respectively, expand the first and second bridge members 61 and 62 whereby the first and second bridge members 61 and 62 move linearly away from each other such that the first and second ends 58 and 59 move linearly to reside at a second distance 76 that is greater than the first distance 75. Since the insertion shape 52 is not the regular inherent shape of the implant 50, the bridge 53 typically is mechanically constrained using an implant retainer whereby the implant retainer maintains the bridge 53 and thus the first bridge member 61 and the second bridge member 62 in the insertion form 74. In particular, the implant retainer, which will be described more fully herein, is configured to engage drill guides coupled with the implant 50 at the first and second openings 67 and 68 thereof such that the implant retainer holds the bridge 53, resulting in the implant retainer constraining the deformed transition sections 63 and 64 in order to maintain the implant 50 in the insertion shape 52. In order for the implant retainer to engage drill guides coupled with the implant 50 at the first and second openings 67 and 68 thereof, the implant 50 when residing in the insertion shape 52 includes a known distance 77 between the first and second openings 67 and 68. After implantation into bone, bones, or bone pieces and a release of the implant retainer, including if necessary a heating of the implant 50, the implant 50 delivers the energy stored in the transition sections 63 and 64 whereby the bridge 53 and thus the first bridge member 61 and the second bridge member 62 attempt to transition from the insertion form 74 to the natural form 73 such that the implant 50 affixes the bone, bones, or bone pieces through an application of a compressive force thereto.

Figure 1E:
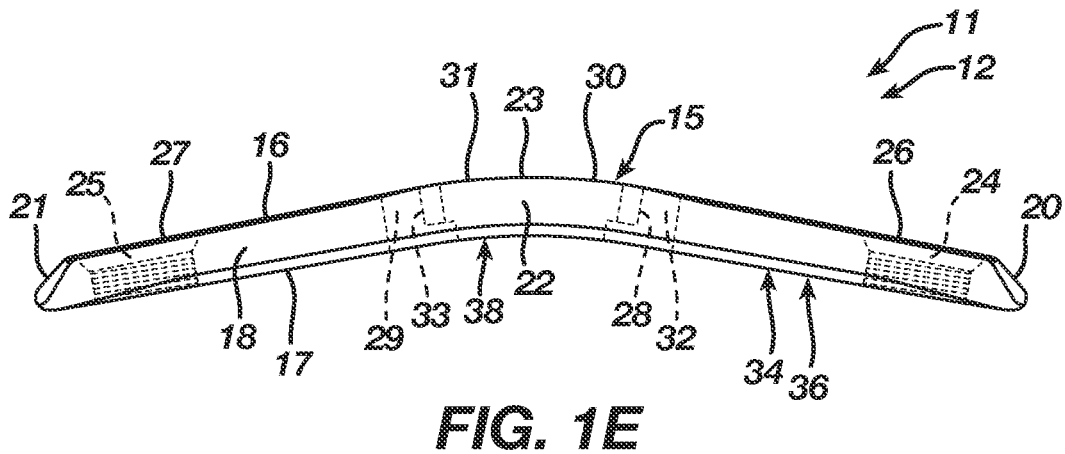
FIG. 1E is an elevation view illustrating an alternative of the orthopedic implant according to the first embodiment in a natural shape.
Figure 1F:
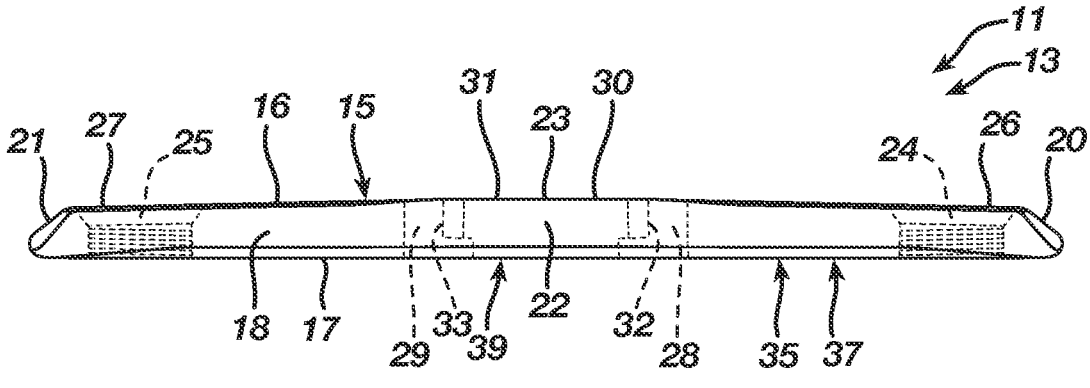
FIG. 1F is an elevation view illustrating an alternative of the orthopedic implant according to the first embodiment in an insertion shape.
Figure 4A:
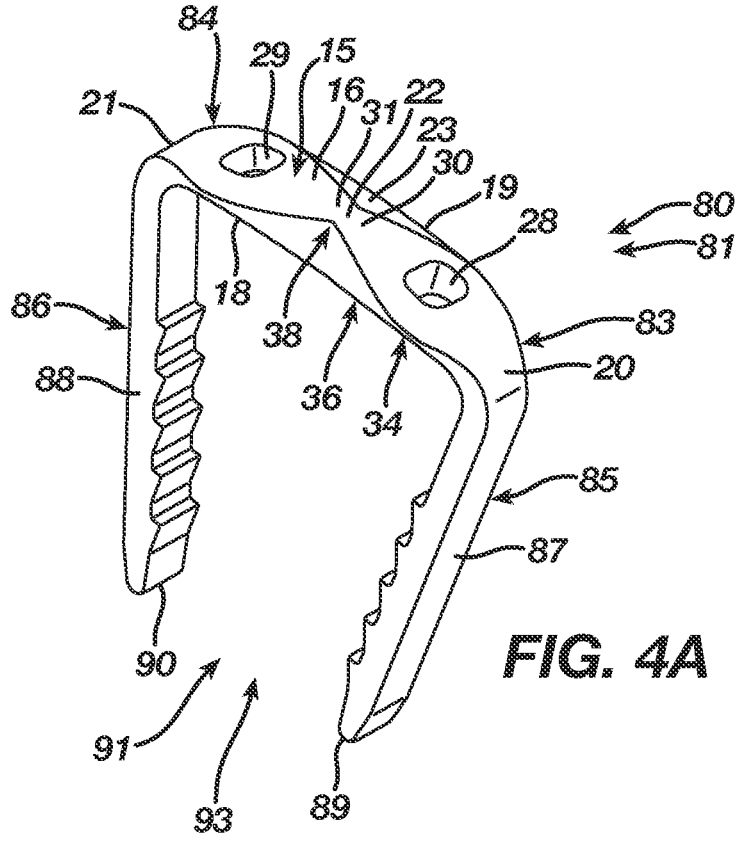
FIG. 4A is a top isometric view illustrating an orthopedic implant according to a fourth embodiment in a natural shape.
Figure 4B:
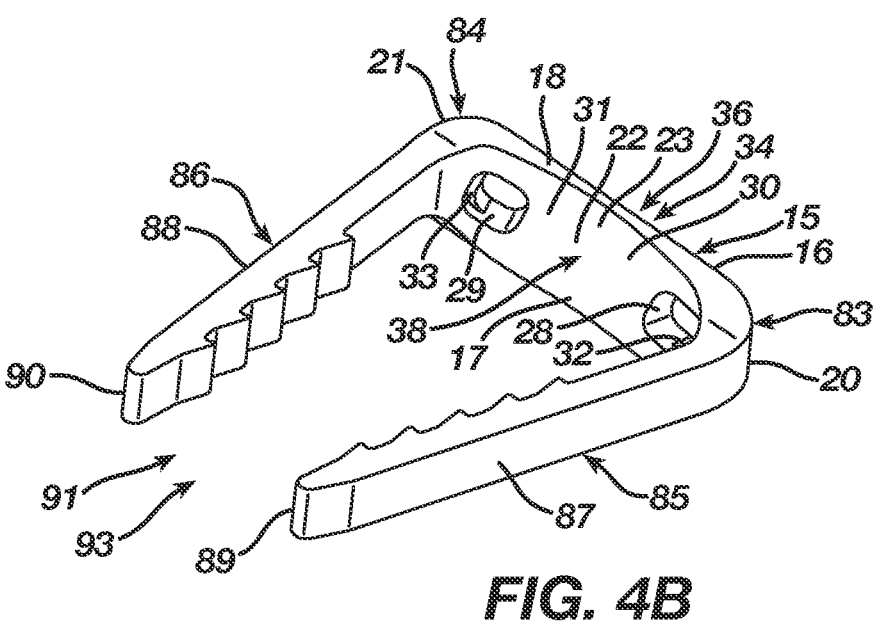
FIG. 4B is a bottom isometric view illustrating the orthopedic implant according to the fourth embodiment in the natural shape.
Figure 4C:
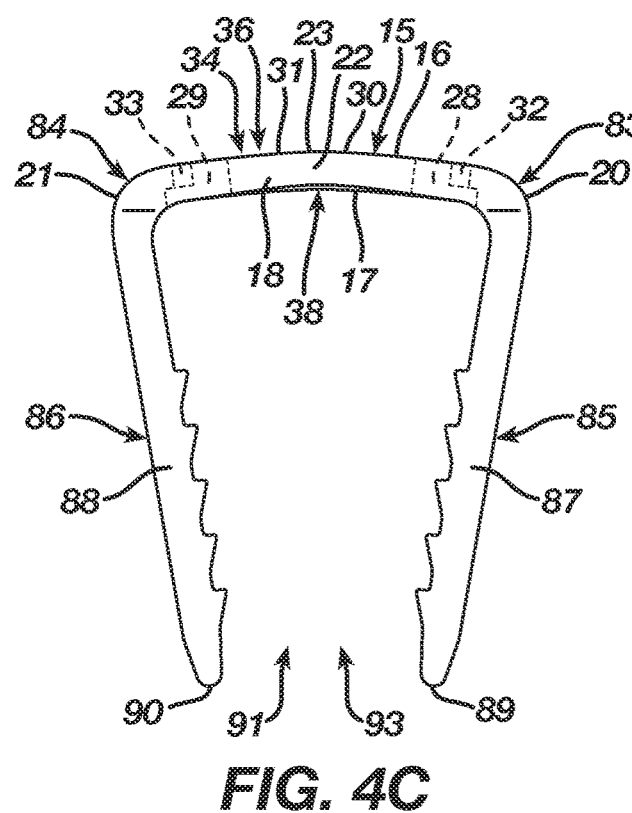
FIG. 4C is a front view illustrating an orthopedic implant according to the fourth embodiment in the natural shape.
Figure 4D:
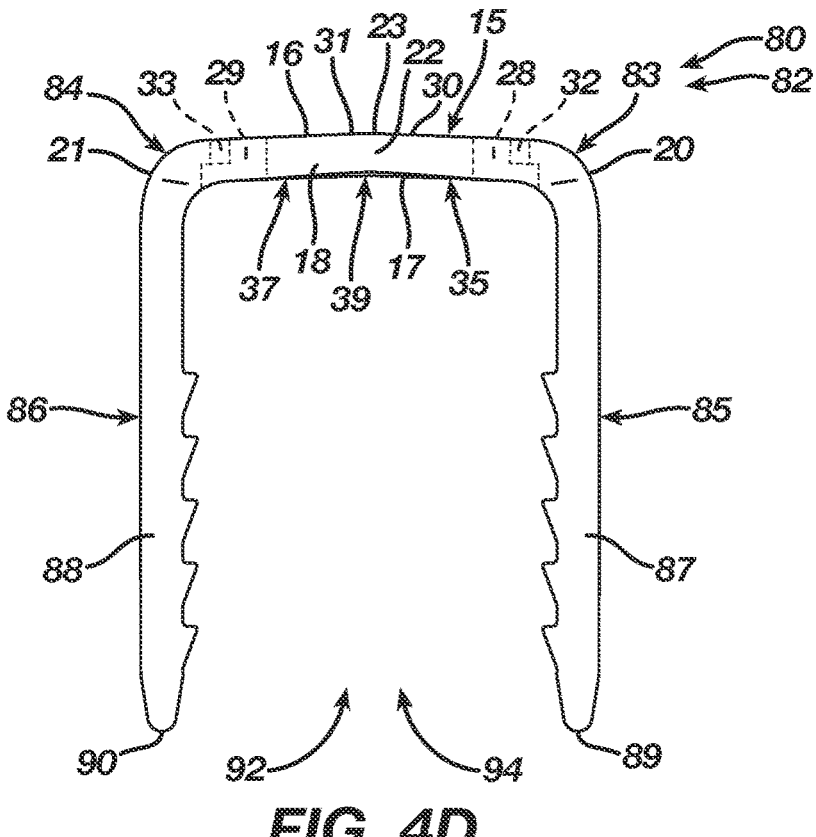
FIG. 4D is a front view illustrating the orthopedic implant according to the fourth embodiment in the insertion shape.
Figure 4E:
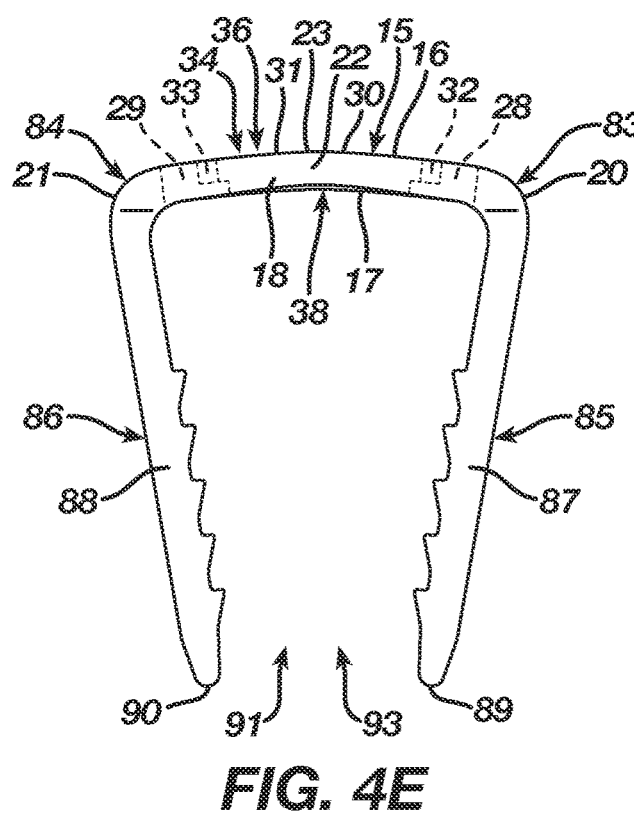
FIG. 4E is a front view illustrating an alternative of the orthopedic implant according to the fourth embodiment in a natural shape.
Figure 4F:
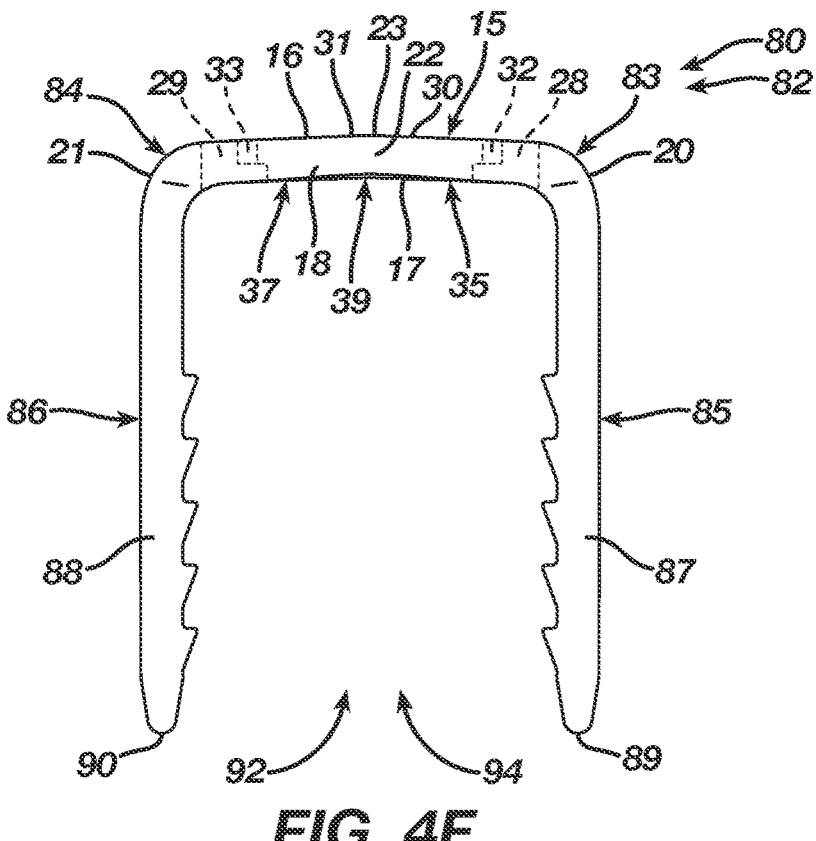
FIG. 4F is a front view illustrating the alternative of the orthopedic implant according to the fourth embodiment in the insertion shape.

FIGS. 4A-4C illustrate an orthopedic implant 80 according to a fourth embodiment in a natural shape 81, whereas FIG. 4D illustrates the orthopedic implant 80 in an insertion shape 82. FIG. 4E illustrates an alternative of the orthopedic implant 80 according to the fourth embodiment in the natural shape 81, whereas FIG. 4F illustrates the alternative of the orthopedic implant 80 in the insertion shape 82. The implant 80 is similar in design and operation relative to the implant 11 according to the first embodiment as illustrated in FIGS. 1A-1D and the alternative embodiment as illustrated in FIGS. 1E-1F such that, for the sake of brevity, only differences therebetween will be described herein. Moreover, one of ordinary skill in the art will recognize that like parts of the implant 80 labeled with like numerals of the implant 11 incorporate a design and function as previously set forth in the detailed description of the implant 11 according to the first embodiment. The implant 11 in the first embodiment includes first and second anchoring segments 26 and 27 with respective first and second openings 24 and 25 configured to receive therethrough anchoring members that secure the implant 11 with bone, bones, or bone pieces at the first and second anchoring segments 26 and 27. As an alternative to the first and second anchoring segments 26 and 27 of the implant 11, the implant 80 eliminates the first and second openings 24 and 25 in favor of anchoring segments 83 and 84 incorporating respective integrated anchoring members 85 and 86 that facilitate affixation of the implant 80 with bone, bones, or bone pieces. More particularly, the integrated anchoring member 85 in the fourth embodiment and the alternative thereof includes a first leg 87 extending from the first end 20 of the implant 80 and thus the bridge 15 in order to provide the implant 80 and thus the bridge 15 with the anchoring segment 83. Likewise, the integrated anchoring member 86 includes a second leg 88 extending from the second end 21 of the implant 80 and thus the bridge 15 in order to provide the implant 80 and thus the bridge 15 with the anchoring segment 84. In the fourth embodiment and the alternative thereof, the first and second legs 87 and 88 are formed integrally with the implant 80 and thus the bridge 15 at respective first and second ends 20 and 21. Each leg 87 and 88, which has a respective tip 89 and 90, may include barbs thereon that improve the pull-out resistance of the implant 80. The implant 80 includes the integrated anchoring members 85 and 86 in the form of the first and second legs 87 and 88 in order to facilitate a securing of the implant 80 with bone, bones, or bone pieces whereby the bridge 15 between the first and second legs 87 and 88 traverses a fixation zone of the bone, bones, or bone pieces such that the implant 80, after its insertion and attempted transition from the insertion shape 82 to the natural shape 81, delivers energy to the bone, bones, or bone pieces at the fixation zone.

The regular inherent shape of the implant 80, as illustrated in FIGS. 4A-4C and 4E, is the natural shape 81 where the transition section 22 locates the bridge 15 in the natural form 34 consisting of a closed or angular profile whereby the first and second ends 20 and 21 reside at the first distance 36 and the first aperture and second apertures 28 and 29 reside at the first distance 38. Locating the bridge 15 in the natural form 34 places the first leg 87 and the second leg 88 in a natural position 91 whereby the first and second legs 87 and 88 are convergent and spaced apart at a first distance 93. Nevertheless, as illustrated in FIGS. 4D and 4F, the implant 80 is deformable under the action of superelasticity or temperature dependent shape memory to the insertion shape 82 where the transition section 22 deforms to store energy while also moving the bridge 15 from the natural form 34 to the insertion form 35 which is an open or substantially linear profile whereby the first and second ends 20 and 21 reside at the second distance 37 and the first and second apertures 28 and 29 reside at the second distance 39. Moving the bridge 15 to the insertion form 35 places the first leg 87 and the second leg 88 in an insertion position 92 whereby the first and second legs 87 and 88 are substantially parallel and spaced apart at a second distance 94 that is greater than the first distance 93. Since the insertion shape 82 is not the regular inherent shape of the implant 80, the bridge 15 typically is mechanically constrained using an implant retainer whereby the implant retainer maintains the bridge 15 in the insertion form 35 and thus the first and second legs 87 and 88 in the insertion position 92. In particular, the implant retainer inserts into the first and second apertures 28 and 29 and engages the catches 32 and 33 such that the implant retainer holds the bridge 15, resulting in the implant retainer constraining the deformed transition section 22 in order to maintain the implant 80 in the insertion shape 82 with the bridge 15 in the insertion form 35 and the first and second legs 87 and 88 in the insertion position 92. After implantation into bone, bones, or bone pieces and a release of the implant retainer, including if necessary a heating of the implant 80, the implant 80 delivers the energy stored in the transition section 22 whereby the implant 80 attempts to transition from the insertion shape 82 to the natural shape 81 through an attempted transition of the bridge 15 from the insertion form 35 to the natural form 34 and an attempted transition of the first and second legs 87 and 88 from the insertion position 92 to the natural position 91 such that the implant 80 affixes the bone, bones, or bone pieces through an application of a compressive force thereto.

Figure 5A:
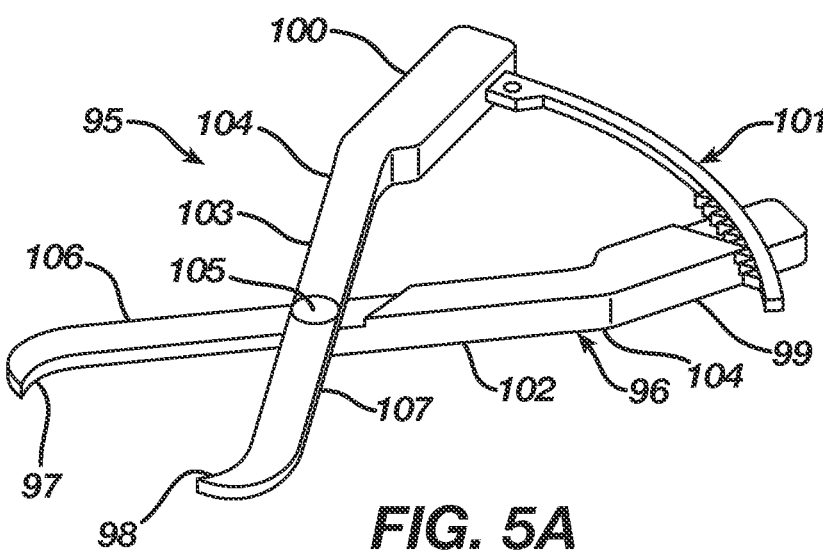
FIG. 5A is a top isometric view illustrating an implant retainer according to a first embodiment.
Figure 5B:
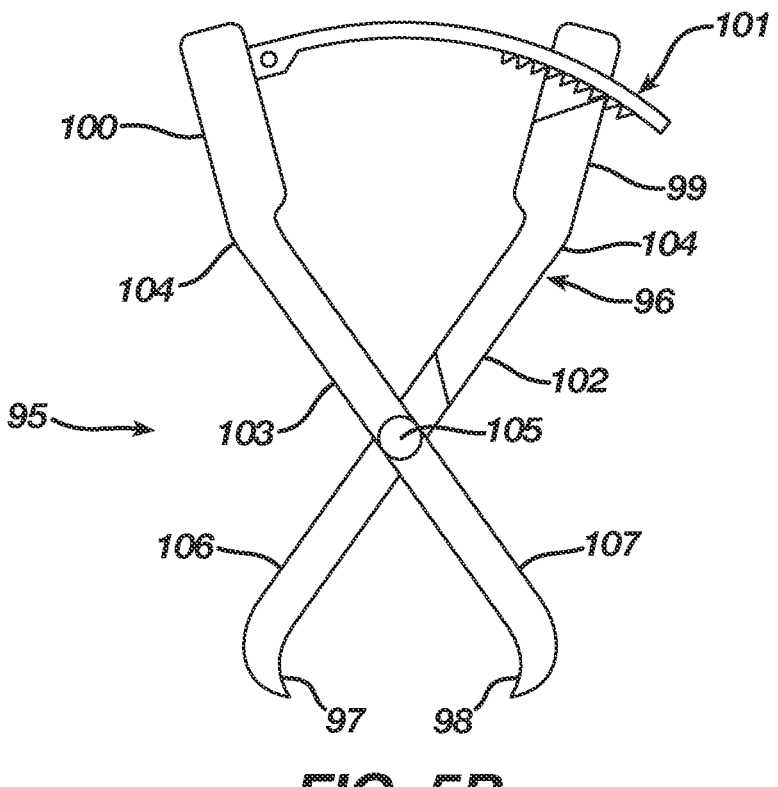
FIG. 5B is a front view illustrating the implant retainer according to the first embodiment.

FIGS. 5A-5B illustrate an implant retainer 95 according to a first embodiment. The implant retainer 95 in the first embodiment comprises forceps 96 including hooks 97 and 98, each of which is configured to engage a drill guide. The hooks 97 and 98 in the first embodiment are inward facing hooks. The forceps 96 include handles 99 and 100 and a locking ratchet 101 extending between the handles 99 and 100 whereby the locking ratchet 101 is configured to arrest the movement of the handles 99 and 100 thereby locking the forceps 96 in engagement with drill guides. The forceps 96 include shanks 102 and 103 extending respectively from handles 99 and 100 at an angle 104 that produces a convergence thereof. The shanks 102 and 103 at the convergence thereof incorporate a hinge 105 that secures the shanks 102 and 103 together and further functions as a pivot point for the forceps 96. The forceps 96 include blades 106 and 107 terminating respectively in the inward facing hooks 97 and 98. The blades 106 and 107 extend respectively from the shanks 102 and 103 along the angle 104 in a traversal of the hinge 105 such that the blade 106 locates the hook 97 positionally opposite relative to the handle 99 and the blade 107 locates the hook 98 positionally opposite relative to the handle 100. Actuation of the forceps 96, as will be described more fully herein, includes a manipulation of the handles 99 and 100 resulting in the hooks 97 and 98 each engaging a drill guide followed by a locking of the forceps 96 via the locking ratchet 101. In the first embodiment, manipulation of the handles 99 and 100 consists of closing the handles 99 and 100 and thus the forceps 96 until the hooks 97 and 98 engage drill guides.

Figures 6A, 6B:
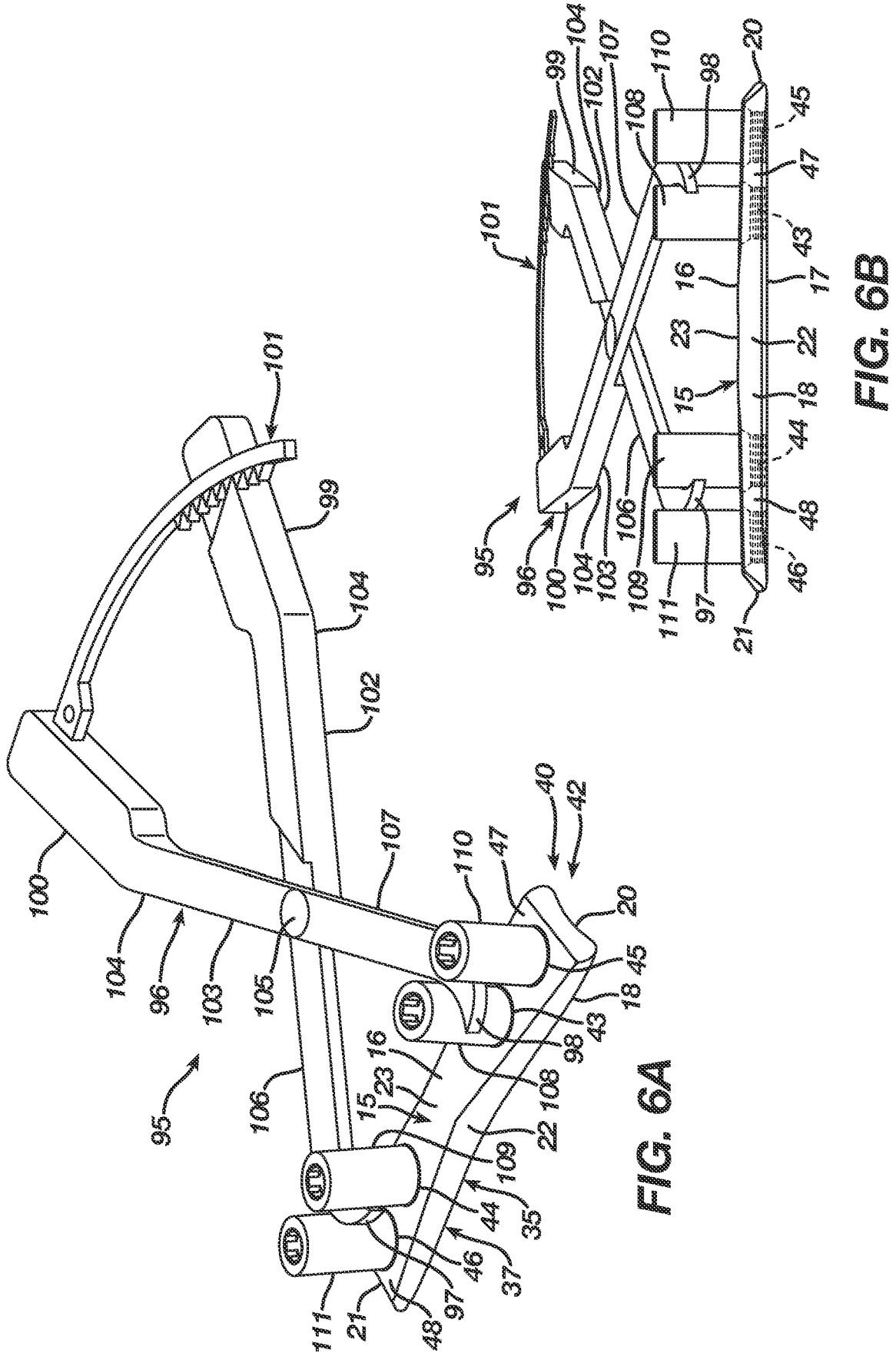
FIG. 6A is a top isometric view illustrating the implant retainer according to the first embodiment and the orthopedic implant according to the second embodiment in the insertion shape forming an orthopedic fixation system.
FIG. 6B is a front isometric view illustrating the implant retainer according to the first embodiment and the orthopedic implant according to the second embodiment in the insertion shape forming the orthopedic fixation system.

FIGS. 6A-6B illustrate the orthopedic fixation system 10 including the orthopedic implant 40 according to the second embodiment and the implant retainer 95 according to the first embodiment, which, more particularly, comprise the forceps 96. Forming the orthopedic fixation system 10 includes securing first, second, third, and fourth drill guides 108, 109, 110, and 111 respectively with the first, second, third, and fourth openings 43, 44, 45, and 46. After coupling the first, second, third, and fourth drill guides 108, 109, 110, and 111 with the implant 40, the forceps 96 using the handles 99 and 100 are positioned with the hooks 97 and 98 thereof respectively contacting the first and second drill guides 108 and 109 at exterior sides thereof. Upon an actuation of the forceps 96, which includes a manipulation of the handles 99 and 100 through a closing thereof via squeezing, the hooks 97 and 98 respectively engage the first and second drill guides 108 and 109, resulting in the forceps 96 applying a force to the implant 40 that facilitates transition of the implant 40 from the natural shape 41 to the insertion shape 42. More particularly, the implant 40 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Once the implant 40 transitions to the insertion shape 42, an engagement of the locking ratchet 101 locks the forceps 96 at the hooks 97 and 98 with the first and second drill guides 108 and 109 whereby the forceps 96 constrain the implant 40 in the insertion shape 42 thereby preventing the implant 40 from returning to the natural shape 41.

In an alternative forming of the orthopedic fixation system 10, the implant 40, after the coupling of the first, second, third, and fourth drill guides 108, 109, 110, and 111 with the implant 40, is mechanically deformed from the natural shape 41 to the insertion shape 42. More particularly, the implant 40 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Mechanical deformation of the implant 40 may include cooling of the implant 40 whereby the implant 40 transitions from its austenite phase to its martensite phase in order to facilitate an easier mechanical deformation of the implant 40 from the natural shape 41 to the insertion shape 42 prior to an engagement of the forceps 96 with the implant 40. After mechanical deformation of the implant 40 from the natural shape 41 to the insertion shape 42, the forceps 96 using the handles 99 and 100 are positioned with the hooks

97 and 98 thereof respectively contacting the first and second drill guides 108 and 109 at exterior sides thereof. Upon an actuation of the forceps 96, which includes a manipulation of the handles 99 and 100 through a closing thereof via squeezing, the hooks 97 and 98 respectively engage the first and second drill guides 108 and 109. Once the hooks 97 and 98 respectively engage the first and second drill guides 108 and 109, an engagement of the locking ratchet 101 locks the forceps 96 at the hooks 97 and 98 with the first and second drill guides 108 and 109 whereby the forceps 96 constrain the implant 40 in the insertion shape 42 thereby preventing the implant 40 from returning to the natural shape 41.

In accordance with the orthopedic fixation system 10, the implant retainer 95, when engaged with the implant 40 in that the forceps 96 are locked on the first and second drill guides 108 and 109 as previously described, retains the implant 40 in the insertion shape 42 such that the implant 40 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the forceps 96 then places the implant 40 across the first bone and the second bone with the transition section 22 of the bridge 15 located at the fixation zone. Upon placement of the implant 40, the surgeon secures the implant 40 with the first and second bones using first and second locating pins. The first locating pin inserts through the first drill guide 108 and into the first bone thereby securing the implant 40 at its anchoring segment 47 with the first bone. Likewise, the second locating pin inserts through the second drill guide 109 and into the second bone thereby securing the implant 40 at its anchoring segment 48 with the second bone. The first and second locating pins hold the implant 40 on the first and second bones with the first and second bones aligned in the orientation that promotes fixation. If desired, the surgeon may secure the first locating pin with the first drill guide 108 via a first collar coupled with the first drill guide 108 and the second locating pin with the second drill guide 109 via a second collar coupled with the second drill guide 109.

After securing the implant 40 with the first and second bones using the first and second locating pins, the surgeon creates drill holes in the first and second bones using the third and fourth drill guides 110 and 111. The surgeon inserts a drill bit through the third drill guide 110 and the third opening 45 and then utilizes the drill bit to form a drill hole in the first bone at the third opening 45. Likewise, the surgeon inserts a drill bit through the fourth drill guide 111 and the fourth opening 46 and then utilizes the drill bit to form a drill hole in the second bone at the fourth opening 46.

With a drill hole formed in the first bone at the third opening 45 and the second bone at the fourth opening 46, the surgeon removes the third drill guide 110 from the third opening 45 and inserts, via an insertion tool such as a screwdriver, an anchoring member in the form of a screw through the third opening 45 and into the first bone until the screw at a head thereof resides substantially, completely within the third opening 45, whereby the screw affixes the implant 40 at the anchoring segment 47 with the first bone. Likewise, the surgeon removes the fourth drill guide 111 from the fourth opening 46 and inserts, via an insertion tool such as a screwdriver, an anchoring member in the form of a screw through the fourth opening 46 and into the second bone until the screw at a head thereof resides substantially, completely within the fourth opening 46, whereby the screw affixes the implant 40 at the anchoring segment 48 with the second bone.

Once the surgeon affixes the implant 40 at the anchoring segment 47 with the first bone and at the anchoring segment 48 with the second bone, the surgeon creates drill holes in the first and second bones using the first and second drill guides 108 and 109. The surgeon inserts a drill bit through the first drill guide 108 and the first opening 43 and then utilizes the drill bit to form a drill hole in the first bone at the first opening 43. Likewise, the surgeon inserts a drill bit through the second drill guide 109 and the second opening 44 and then utilizes the drill bit to form a drill hole in the second bone at the second opening 44.

With drill holes formed in the first bone at the first opening 43 and the second bone at the second opening 44, the surgeon releases the locking ratchet 101 and removes the forceps 96 at the hooks 97 and 98 from the first and second drill guides 108 and 109. The surgeon further removes the first drill guide 108 from the first opening 43 and inserts, via an insertion tool such as a screwdriver, an anchoring member in the form of a screw through the first opening 43 and into the first bone until the screw at a head thereof resides substantially, completely within the first opening 43, whereby the screw affixes the implant 40 at the anchoring segment 47 with the first bone. Likewise, the surgeon removes the second drill guide 109 from the second opening 44 and inserts, via an insertion tool such as a screwdriver, an anchoring member in the form of a screw through the second opening 44 and into the second bone until the screw at a head thereof resides substantially, completely within the second opening 44, whereby the screw affixes the implant 40 at the anchoring segment 48 with the second bone.

In light of the affixation of the implant 40 with the first and second bones across the fixation zone and the removal of the forceps 96 from the first and second drill guides 108 and 109, the implant 40 attempts transition from the insertion shape 42 to the natural shape 41 whereby the implant 40 delivers the energy stored in the transition section 22 to the first bone and the second bone, resulting in the implant 40 affixing the first bone and the second bone through an application of a compressive force to the fixation zone. The implant retainer 95 accordingly improves insertion of the implant 40 because the implant retainer 95 does not release its constraint of the implant 40 until the implant 40 is affixed to the first and second bones with its transition section 22 located across the fixation zone thereof such that the implant retainer 95 prevents the implant 40 from prematurely delivering the energy stored therein to the first and second bones at the fixation zone thereof. While the implant 40 may attempt transition from the insertion shape 42 to the natural shape 41 before a surgeon completes insertion of screws through the first and second openings 43 and 44, one of ordinary skill in the art will recognize the prior securing of the implant 40 with the first and second bones via the third and fourth openings 45 and 46 thereof ensures the first bone and the second bone at the fixation zone remain in the orientation that promotes their fixation proper healing.

Figure 7:
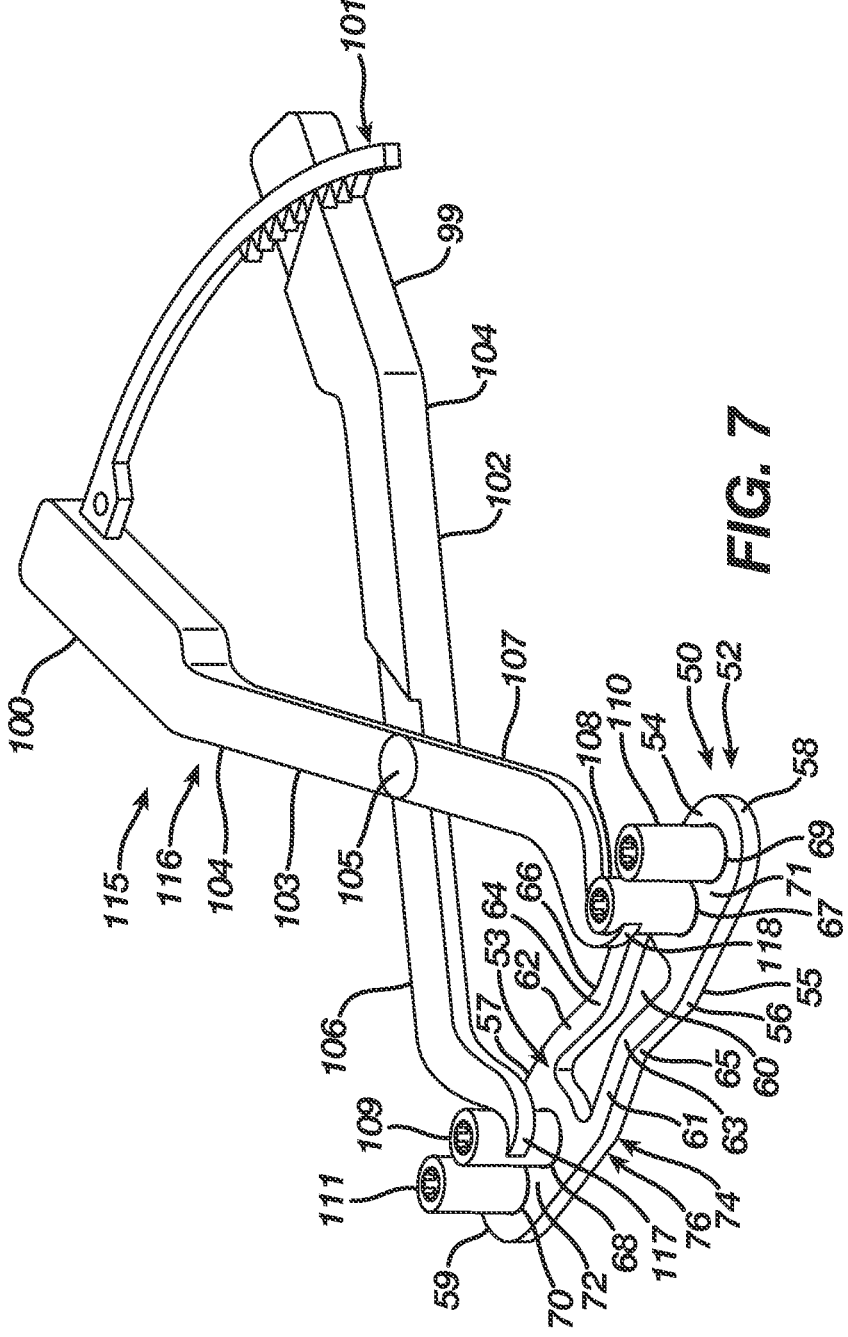
FIG. 7 is a top isometric view illustrating an implant retainer alternative to the implant retainer according to the first embodiment and the orthopedic implant according to the third embodiment in the insertion shape forming the orthopedic fixation system.
Figure 8A:
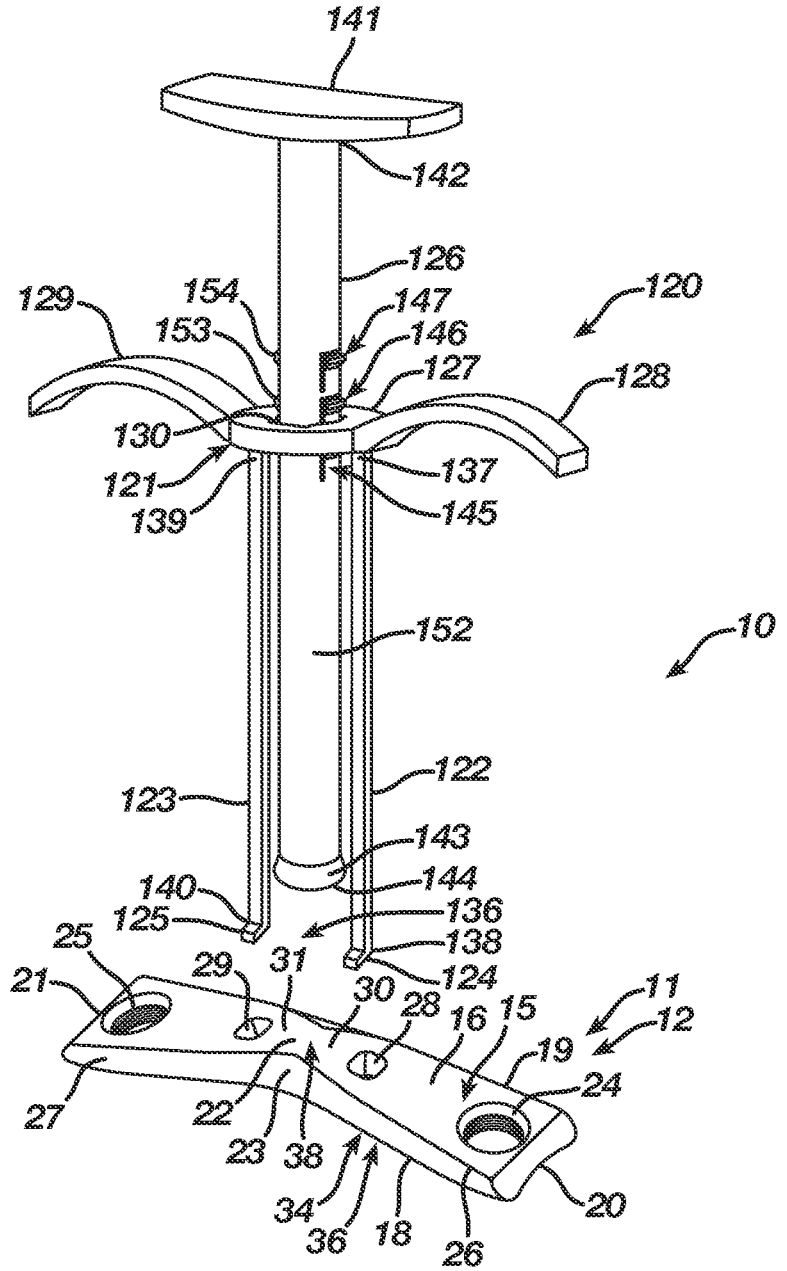
FIG. 8A is a top isometric view illustrating an implant retainer according to a second embodiment and the orthopedic implant according to the first embodiment in the natural shape.
Figure 8B:
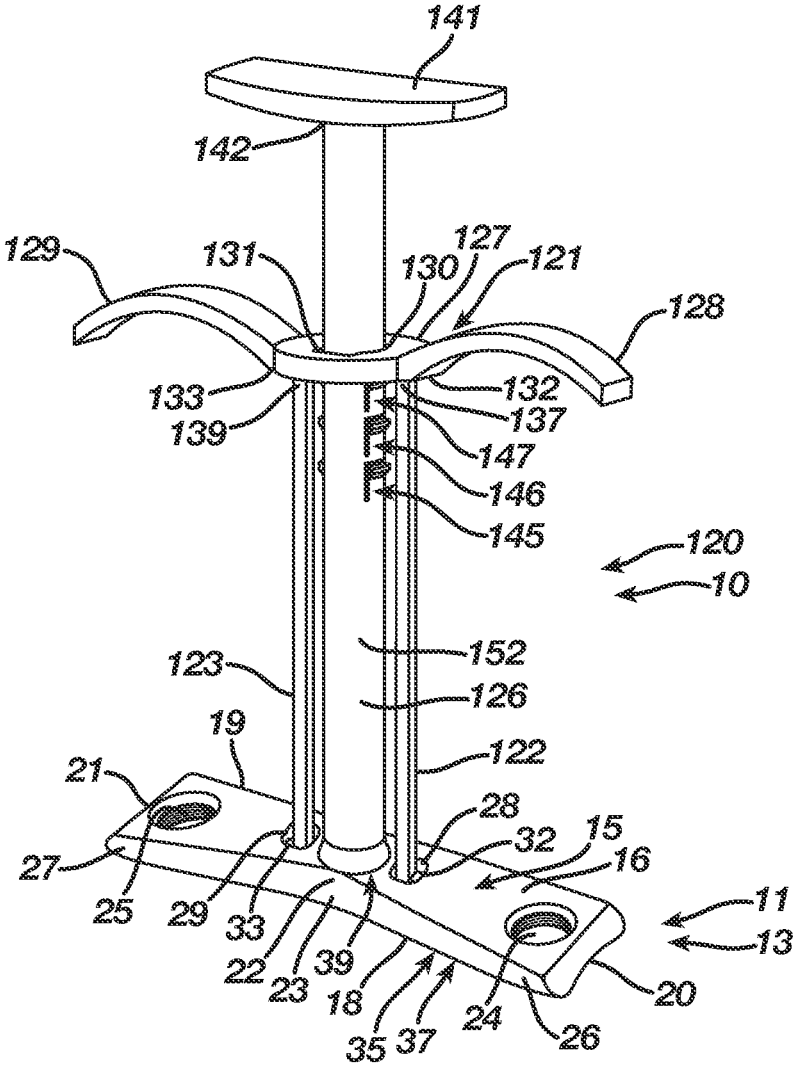
FIG. 8B is a top isometric view illustrating the implant retainer according to the second embodiment and the orthopedic implant according to the first embodiment in the insertion shape forming the orthopedic fixation system.
Figure 8C:
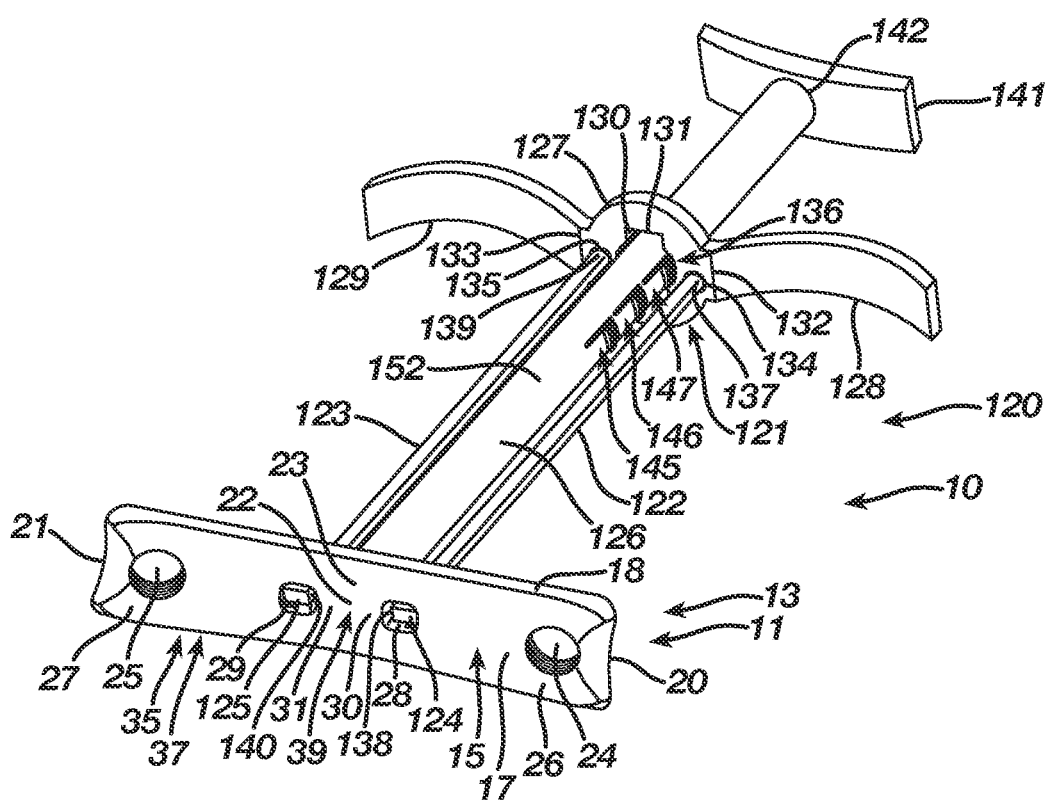
FIG. 8C is a bottom isometric view illustrating the implant retainer according to the second embodiment and the orthopedic implant according to the first embodiment in the insertion shape forming the orthopedic fixation system.
Figure 8D:
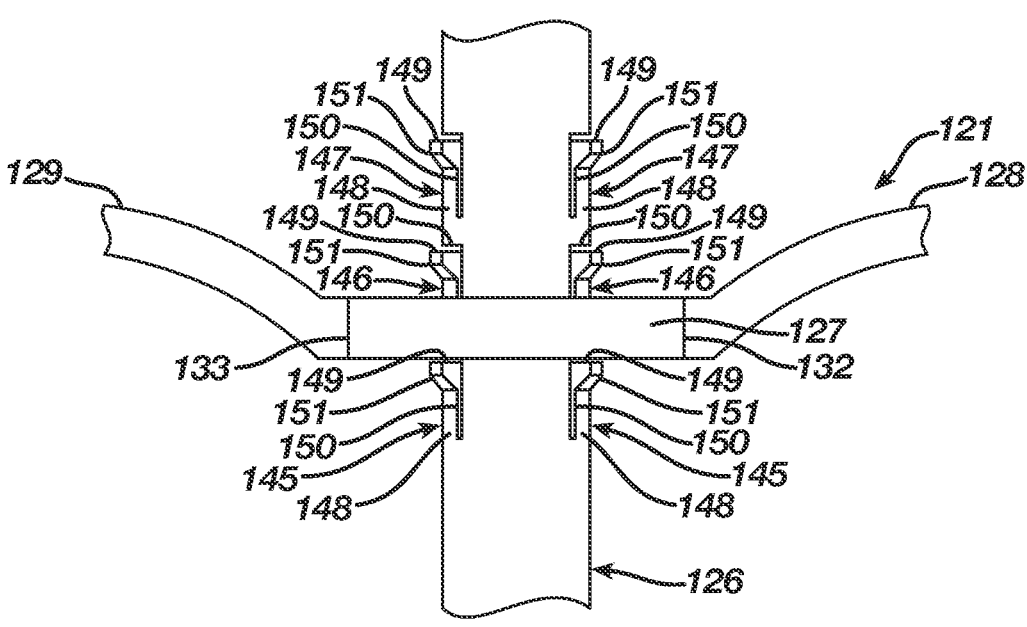
FIG. 8D is a partial front view illustrating the implant retainer according to the second embodiment.
Figure 8E:
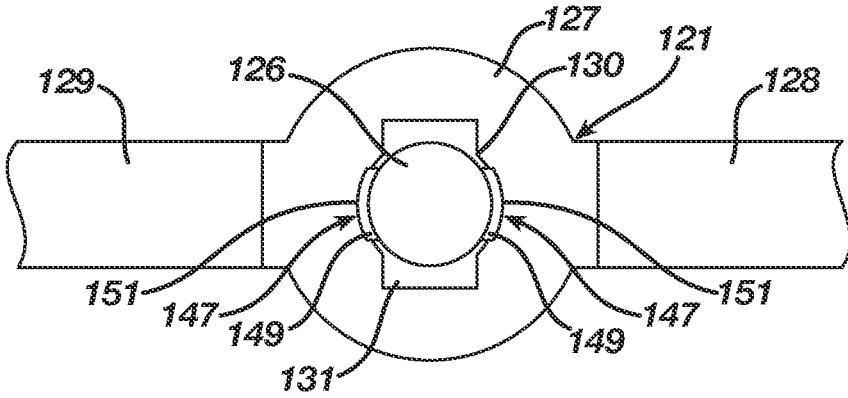
FIG. 8E is a partial top view illustrating the implant retainer according to the second embodiment.
Figure 9A:
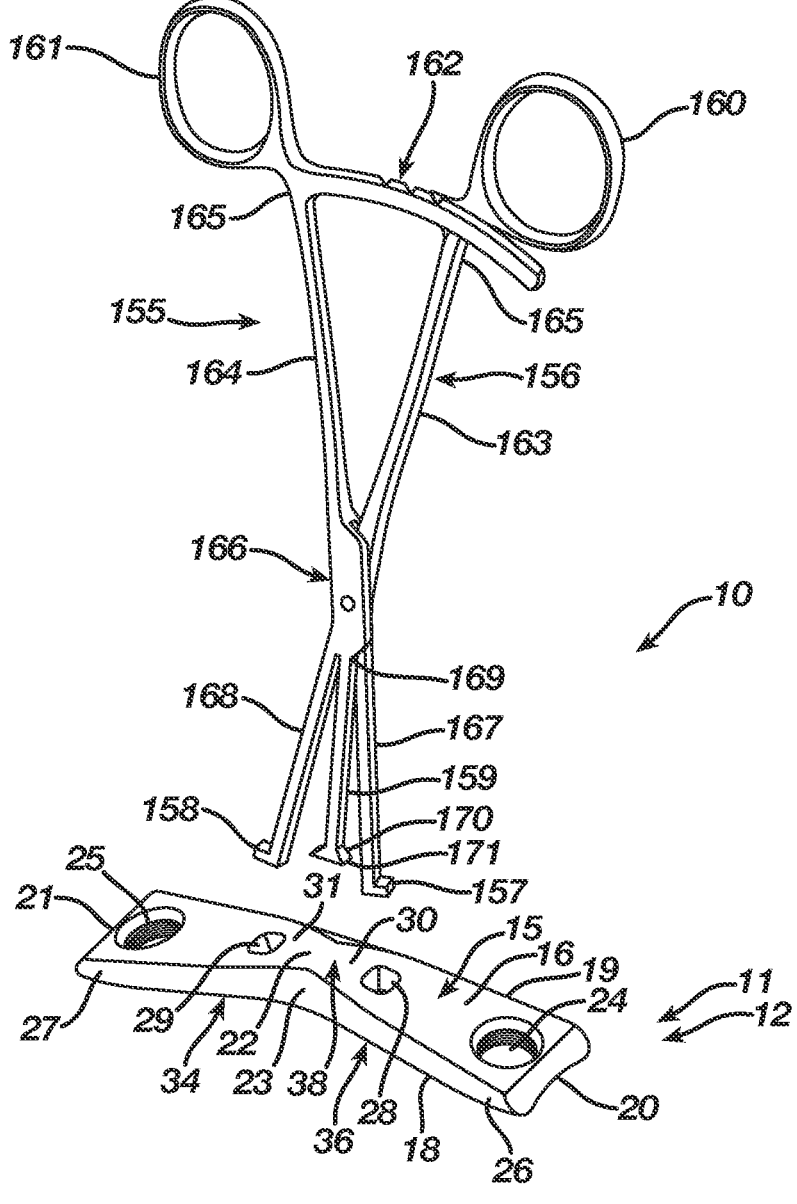
FIG. 9A is a top isometric view illustrating an implant retainer according to a third embodiment and the orthopedic implant according to the first embodiment in the natural shape.
Figure 9B:
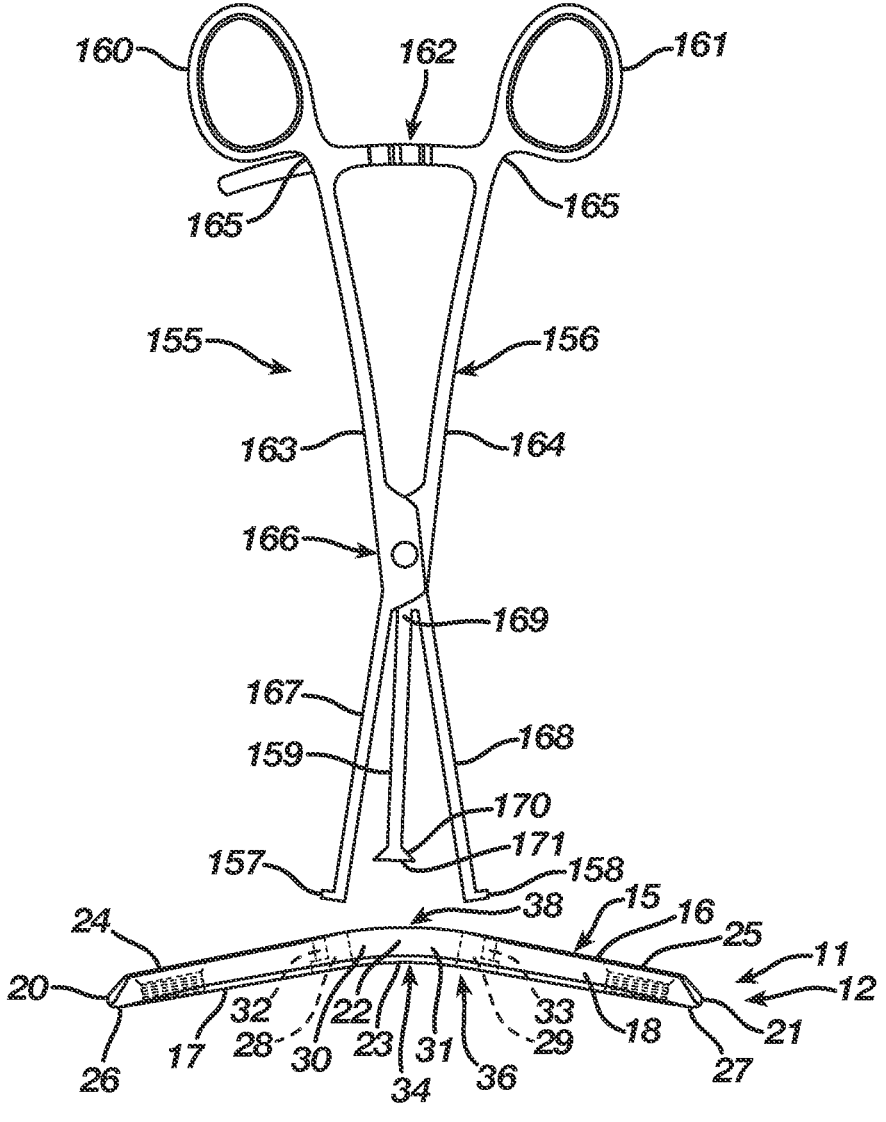
FIG. 9B is a rear view illustrating the implant retainer according to the third embodiment and the orthopedic implant according to the first embodiment in the natural shape.
Figure 9C:
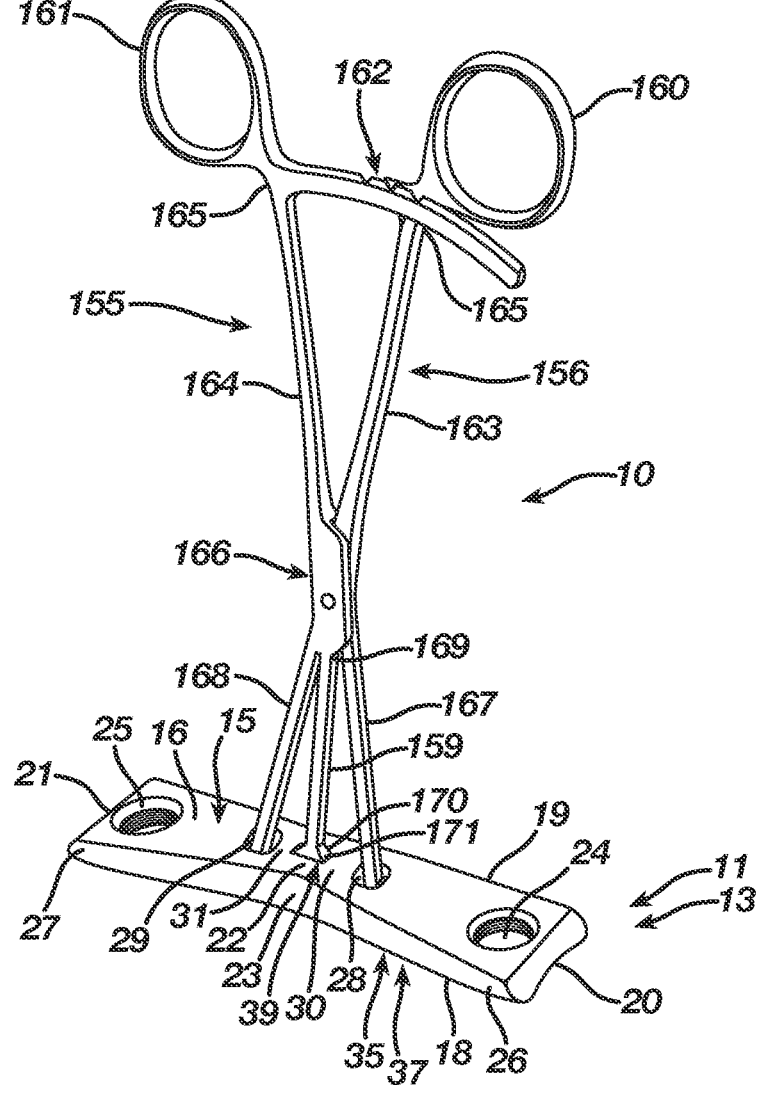
FIG. 9C is a top isometric view illustrating the implant retainer according to the third embodiment and the orthopedic implant according to the first embodiment in the insertion shape forming the orthopedic fixation system.
Figure 9D:
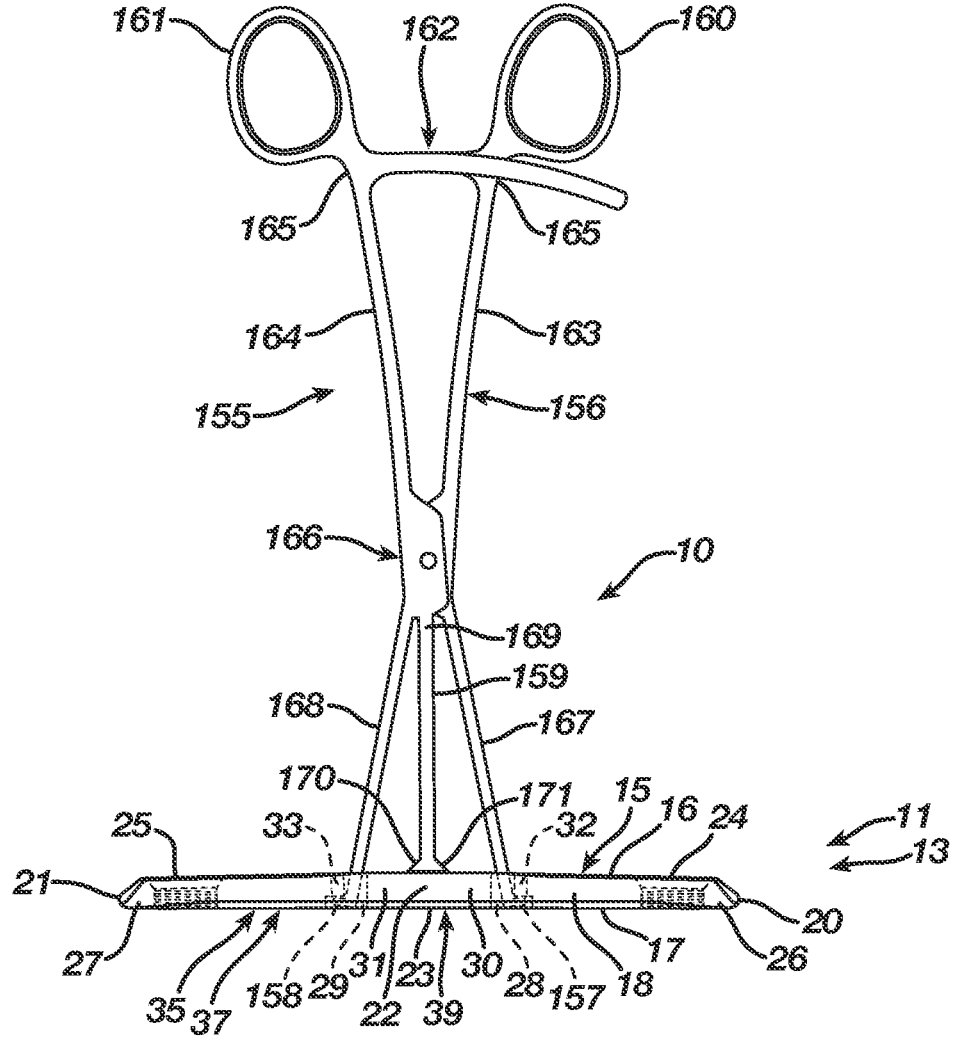
FIG. 9D is a front view illustrating the implant retainer according to the third embodiment and the orthopedic implant according to the first embodiment in the insertion shape forming the orthopedic fixation system.
Figure 10A:
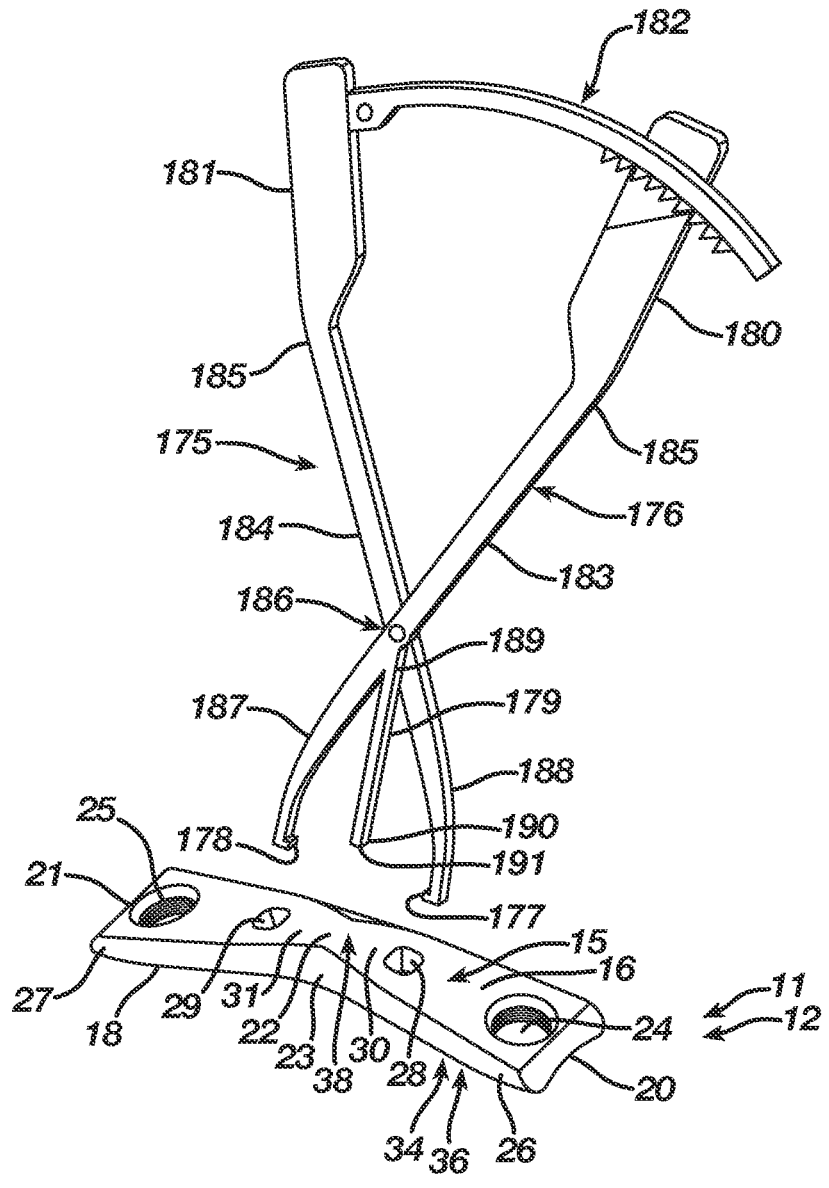
FIG. 10A is a top isometric view illustrating an implant retainer according to a fourth embodiment and the alternative of the orthopedic implant according to the first embodiment in the natural shape.
Figure 10B:
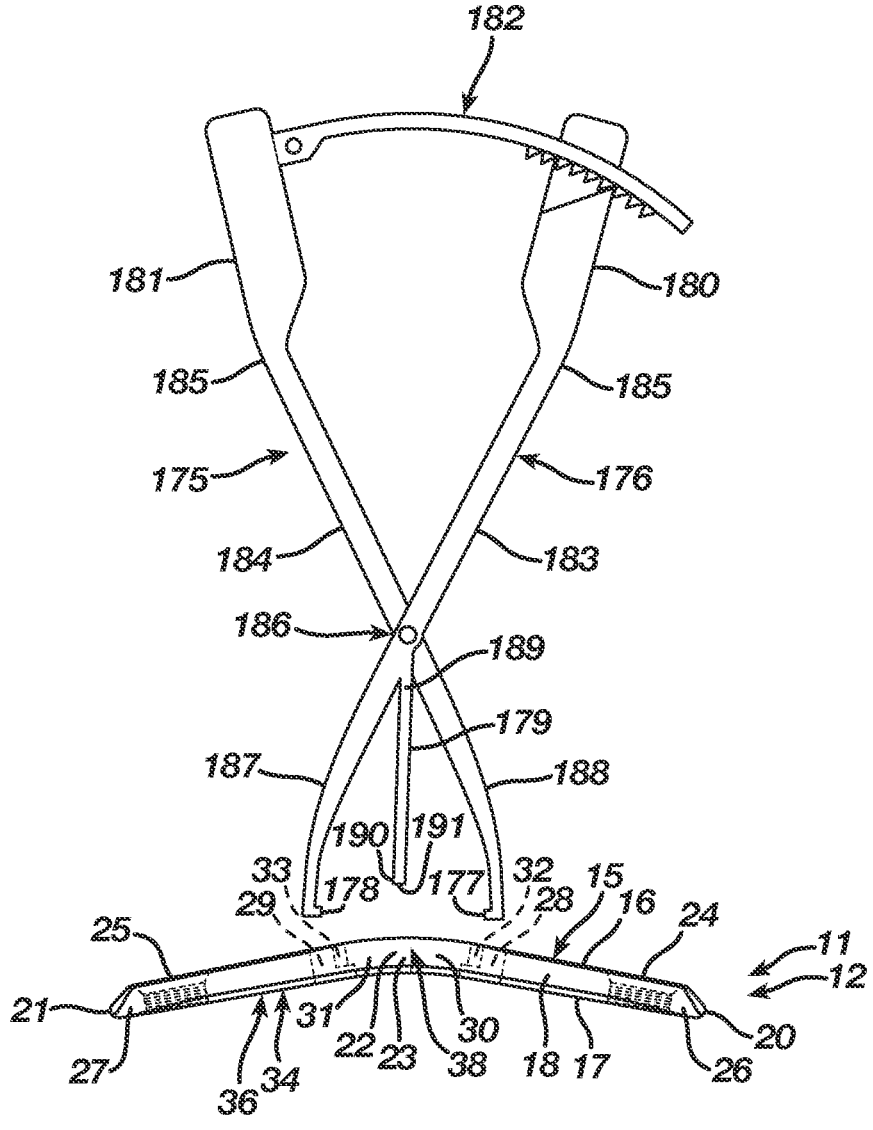
FIG. 10B is a front view illustrating the implant retainer according to the fourth embodiment and the alternative of the orthopedic implant according to the first embodiment in the natural shape.
Figure 10C:
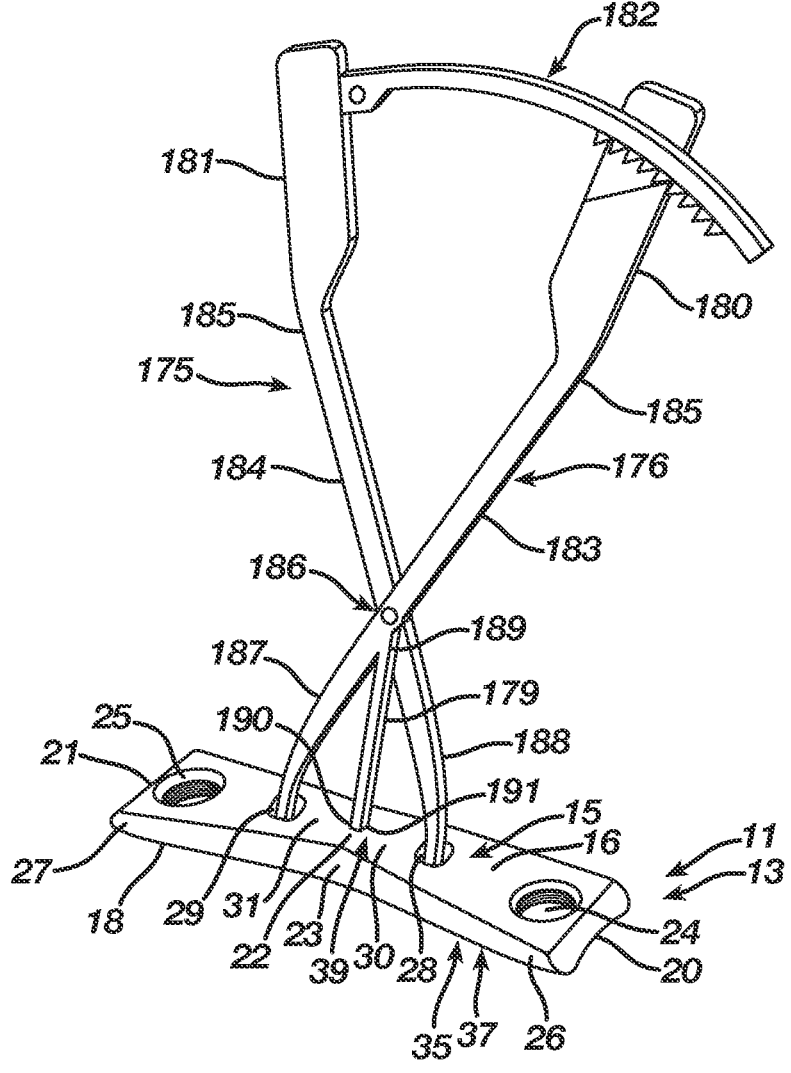
FIG. 10C is a top isometric view illustrating the implant retainer according to the fourth embodiment and the alternative of the orthopedic implant according to the first embodiment in the insertion shape forming the orthopedic fixation system.
Figure 10D:
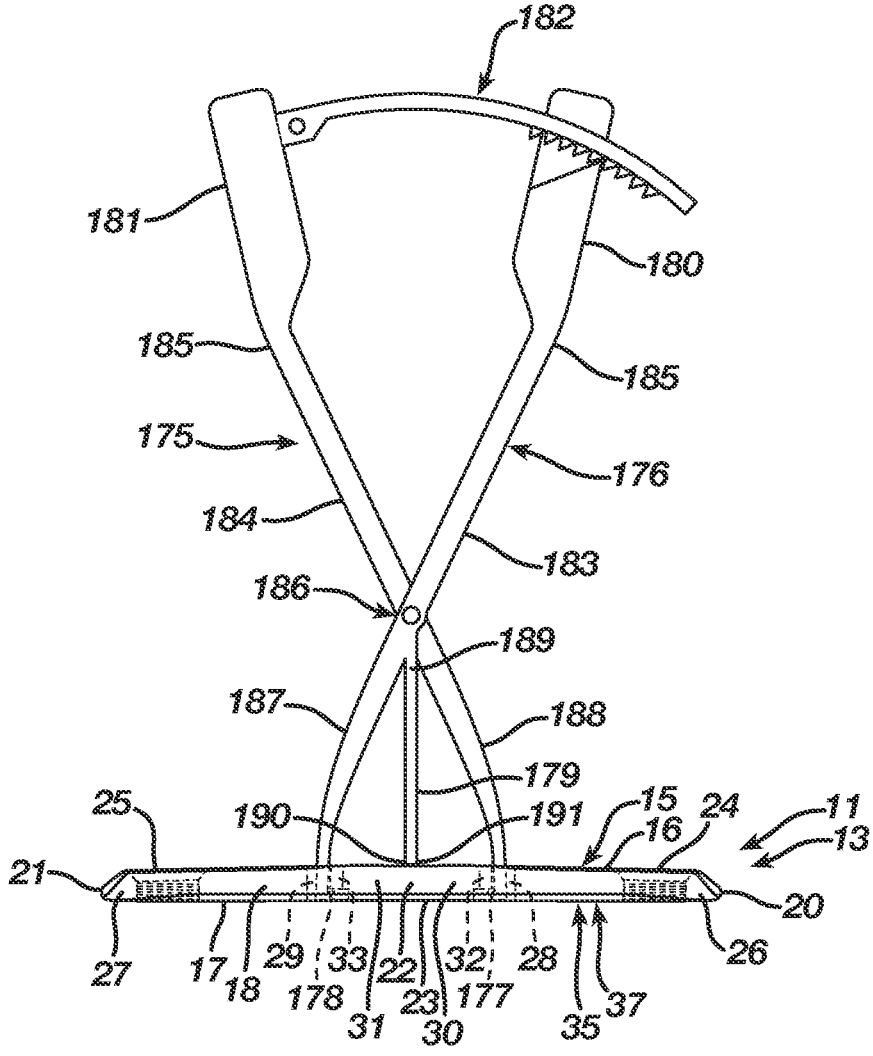
FIG. 10D is a front view illustrating the implant retainer according to the fourth embodiment and the alternative of the orthopedic implant according to the first embodiment in the insertion shape forming the orthopedic fixation system.

FIG. 7 illustrates the orthopedic fixation system 10 including the orthopedic implant 50 according to the third embodiment and an implant retainer 115 alternative to the implant retainer 95 according to the first embodiment, which, more particularly, comprise forceps 116 alternative to the forceps 96. The forceps 116 are substantially similar in design and operation relative to the forceps 96 according to the first embodiment such that, for the sake of brevity, only differences therebetween will be described herein. Moreover, one of ordinary skill in the art will recognize that like parts of the forceps 116 labeled with like numerals of the forceps 96 incorporate a design and function as previously set forth in the detailed description of the forceps 96. The forceps 96 include the hooks 97 and 98, which in the first embodiment are inward facing hooks, whereas the forceps 116 include hooks 117 and 118, which in the alternative embodiment are outward facing hooks. In light of the hooks 117 and 118, actuation of the forceps 116 and manipulation of the handles 99 and 100 consists of opening the handles 99 and 100 and thus the forceps 116 until the hooks 117 and 118 engage drill guides. While the forceps 116 operate through an opening of the handles 99 and 100, one of ordinary skill in the art will recognize that the forceps 116 in an alternative may operate through a closing of the handles 99 and 100 based upon a modification of the forceps 116 to operate based on a manipulation illustrated by a lamina spreader.

Forming the orthopedic fixation system 10 includes securing first, second, third, and fourth drill guides 108, 109, 110, and 111 respectively with the first, second, third, and fourth openings 67, 68, 69, and 70. After coupling the first, second, third, and fourth drill guides 108, 109, 110, and 111 with the implant 50, the forceps 116 using the handles 99 and 100 are positioned with the hooks 117 and 118 thereof respectively contacting the first and second drill guides 108 and 109 at interior sides thereof. Upon an actuation of the forceps 96, which includes a manipulation of the handles 99 and 100 through an opening thereof, the hooks 117 and 118 respectively engage the first and second drill guides 108 and 109, resulting in the forceps 116 applying a force to the implant 50 that facilitates transition of the implant 50 from the natural shape 51 to the insertion shape 52. More particularly, the implant 50 via the transition sections 63 and 64 mechanically deforms to store energy while also moving the bridge 53 from the natural form 73 where the first and second ends 58 and 59 reside at the first distance 75 to the insertion form 74 where the first and second ends 58 and 59 reside at the second distance 76. Once the implant 50 transitions to the insertion shape 52, an engagement of the locking ratchet 101 locks the forceps 116 at the hooks 117 and 118 with the first and second drill guides 108 and 109 whereby the forceps 116 constrain the implant 50 in the insertion shape 52 thereby preventing the implant 50 from returning to the natural shape 51.

In an alternative forming of the orthopedic fixation system 10, the implant 50, after the coupling of the first, second, third, and fourth drill guides 108, 109, 110, and 111 with the implant 50, is mechanically deformed from the natural shape 51 to the insertion shape 52. More particularly, the implant 50 via the transition sections 63 and 64 mechanically deforms to store energy while also moving the bridge 53 from the natural form 74 where the first and second ends 58 and 59 reside at the first distance 75 to the insertion form 74 where the first and second ends 58 and 59 reside at the second distance 76. Mechanical deformation of the implant 50 may include cooling of the implant 50 whereby the implant 50 transitions from its austenite phase to its martensite phase in order to facilitate an easier mechanical deformation of the implant 50 from the natural shape 51 to the insertion shape 52 prior to an engagement of the forceps 116 with the implant 50. After mechanical deformation of the implant 50 from the natural shape 51 to the insertion shape 52, the forceps 116 using the handles 99 and 100 are positioned with the hooks 117 and 118 thereof respectively contacting the first and second drill guides 108 and 109 at interior sides thereof. Upon an actuation of the forceps 116, which includes a manipulation of the handles 99 and 100 through an opening thereof, the hooks 117 and 118 respectively engage the first and second drill guides 108 and 109. Once the hooks 117 and 118 respectively engage the first and second drill guides 108 and 109, an engagement of the locking ratchet 101 locks the forceps 116 at the hooks 117 and 118 with the first and second drill guides 108 and 109 whereby the forceps 116 constrain the implant 50 in the insertion shape 52 thereby preventing the implant 50 from returning to the natural shape 51.

In accordance with the orthopedic fixation system 10, the implant retainer 115, when engaged with the implant 50 in that the forceps 116 are locked on the first and second drill guides 108 and 109 as previously described, retains the implant 50 in the insertion shape 52 such that the implant 50 is ready for securing with bone, bones, or bone pieces. The implant 50 using the forceps 116 secures with bone, bones, or bone pieces employing the procedure previously set forth with respect to the implant 40 and the forceps 96, except release of the forceps 116 from the first and second drill guides 108 and 109 includes a closing of the handles 99 and 100 and thus the forceps 116 until the hooks 117 and 118 disengage from the first and second drill guides 108 and 109.

FIGS. 8A-8D illustrate an implant retainer 120 according to a second embodiment and the orthopedic implant 11 according to the first embodiment utilized in forming the orthopedic fixation system 10. The implant retainer 120 includes a handle 121, a first arm 122 extending from the handle 121 and terminating in a fastener 124, a second arm 123 extending from the handle 121 and terminating in a fastener 125, and a plunger 126 integrated with the handle 121.

The handle 121 includes a center section 127 and a first handgrip 128 and a second handgrip 129 extending from the center section 127 that facilitate a grasping of the handle 121. The handle 121 in the center section 127 includes an aperture 130 that receives the plunger 126 therethrough in order to integrate the plunger 126 with the handle 121. The aperture 130 is sized and includes a configuration that allows an insertion of the plunger 126 relative to the handle 121 while preventing a retraction of the plunger 126 relative to the handle 121. Nevertheless, the aperture 130 includes an elongation 131 that permits the retraction of the plunger 126 relative to the handle 121. The handle 121 in the center section 127 adjacent a first end 132 thereof includes a first bore 134 sized and including a configuration for receipt therein of the first arm 122. Likewise, the handle 121 in the center section 127 adjacent a second end 133 thereof includes a second bore 135 directly opposite from the first bore 134 sized and including a configuration for receipt therein of the second arm 122. The first bore 134 and the second bore 135 are spaced apart across the aperture 130 a distance 136 that facilitates an insertion of the first arm 122 in the first aperture 28 of the implant 11 and an insertion of the second arm 123 in the second aperture 29 of the implant 11. Illustratively, the distance 136 between the first bore 134 and the second bore 135 substantially equals the second distance 39 of the first aperture 28 and the second aperture 29 such that the first arm 122 and the second arm 123, which also reside at the distance 136, respectively insert into the first aperture 28 and the second aperture 29 for engagement with the implant 11 when the implant 11 resides in the insertion shape 13 with the bridge 15 in the insertion form 35. In the alternative, when the implant 11 resides in the natural shape 12 with the bridge 15 in the natural form 34 whereby the first aperture 28 and the second aperture 29 are spaced apart at the first distance 38, the first aperture 28 and the second aperture 29 may be sized sufficiently to receive respectively therein the first arm 122 and the second arm 123 for engagement with the implant 11.

The first arm 122 includes a first end 137 and a second end 138 with the fastener 124 extending therefrom substantially perpendicular in the second embodiment. The first arm 122 at the first end 137 inserts into the first bore 134 while remaining movable within the first bore 134. In accordance therewith, a movement of the first arm 122 within the first bore 134 via a rotation thereof locates the fastener 124 in a bypass position whereby, during an insertion of the first arm 122 at the second end 138 into the first aperture 28, the fastener 124 bypasses the catch 32 protruding into the first aperture 28. Once the fastener 124 bypasses the catch 32, a movement of the first arm 122 within the first bore 134 via a rotation thereof locates the fastener 124 in an interlock position whereby the fastener 124 engages the catch 32 in order to maintain the first arm 122 secured with the implant 11. The fastener 124 of the first arm 122 is sized to reside below and engage the catch 32 without extending past the lower surface 17 of the bridge 15 for the implant 11. The first arm 122 inserts into the first bore 134 while remaining movable therein using any suitable interlock mechanism, such as, for example, a friction fit, threads, a tab on the first arm 122 at the first end 137 and a corresponding groove in the first bore 134. Although the first arm 122 rotates the fastener 124 facing outward in the interlock position for engagement with the implant 11 according to the first embodiment, one of ordinary skill in the art will recognize the first arm 122 may rotate the fastener 124 facing inward in the interlock position for engagement with the implant 11 according to the alternative of the first embodiment.

Similar to the first arm 122, the second arm 123 includes a first end 139 and a second end 140 with fastener 125 extending therefrom substantially perpendicular in the second embodiment. The second arm 123 at the first end 139 inserts into the second bore 135 while remaining movable within the second bore 135. In accordance therewith, a movement of the second arm 123 within the second bore 135 via a rotation thereof locates the fastener 125 in a bypass position whereby, during an insertion of the second arm 123 at the second end 140 into the second aperture 29, the fastener 125 bypasses the catch 33 protruding into the second aperture 33. Once the fastener 125 bypasses the catch 33, a movement of the second arm 123 within the second bore 135 via a rotation thereof locates the fastener 125 in an interlock position whereby the fastener 125 engages the catch 33 in order to maintain the second arm 123 secured with the implant 11. The fastener 125 of the second arm 123 is sized to reside below and engage the catch 33 without extending past the lower surface 17 of the bridge 15 for the implant 11. The second arm 123 inserts into the second bore 135 while remaining movable therein using any suitable interlock mechanism, such as, for example, a friction fit, threads, a tab on the second arm 123 at the first end 139 and a corresponding groove in the second bore 135. Although the second arm 123 rotates the fastener 125 facing outward in the interlock position for engagement with the implant 11 according to the first embodiment, one of ordinary skill in the art will recognize the second arm 123 may rotate the fastener 125 facing inward in the interlock position for engagement with the implant 11 according to the alternative of the first embodiment.

The plunger 126 includes a head 141 atop a first or top end 142 configured to permit manipulation of the plunger 126. The plunger 126 includes a protrusion 143 at a second or bottom end 144 configured to seat the plunger 126 atop the implant 11. The plunger 126 includes one or more stops and in the second embodiment a first or lower stop 145, a second or intermediate stop 146, and a third or upper stop 147 that permit an insertion of the plunger 126 relative to the handle 121 and prevent a retraction of the plunger 126 relative to the handle 121. Each of the lower, intermediate, and upper stops 145-147 connects with the plunger 126 at a proximal end 148 while remaining separated therefrom between the proximal end 148 and a distal end 149 by a pocket 150 in the plunger 126 adjacent the lower, intermediate, and upper stops 145-147. The connection of each of the lower, inter- mediate, and upper stops 145-147 with the plunger 126 at the proximal end 146 in combination with the pocket 150 makes each of the lower, intermediate, and upper stops 145-147 resilient in that each of the lower, intermediate, and upper stops 145-147 enters the pocket 150 in a bypass position to permit insertion of the plunger 126 and exits the pocket 150 in a lock position to prevent retraction of the plunger 126. Each of the lower, intermediate, and upper stops 145-147 includes a ramp 151 incorporating the distal end 149 configured to facilitate entrance of each of the lower, intermediate, and upper stops 145-147 into the pocket 148 while further functioning to prevent retraction of the plunger 126. Although only a single lower, intermediate, and upper stop 145-147 is necessary on the plunger 126, each of the lower, intermediate, and upper stops 145-147 in the second embodiment includes a respective additional stop 145-147 located on the plunger 126 directly opposite there- from in order to produce a more secure engagement of the plunger 126 with the handle 121.

Insertion of the plunger 126 relative to the handle 121 includes pushing on the head 141 of the plunger 126 while grasping the first and second handgrips 128 and 129 of the handle 121 such that the plunger 126 progresses through the center section 127 via the aperture 130. The center section 127 at the aperture 130 contacts one of the lower, interme- diate, and upper stops 145-147 and traverses the lower, intermediate, or upper stop 145-147 including the ramp 151 thereof. The contact of the center section 127 with the ramp 151 during the progression of the plunger 126 depresses the lower, intermediate, or upper stop 145-147 into the pocket 150 resulting in the center section 127 bypassing the lower, intermediate, or upper stop 145-147. Upon the bypassing of the lower, intermediate, or upper stop 145-147 and a ceasing of the pushing on the plunger 126, the handle 121 resides above the lower, intermediate, or upper stop 145-147 such that the plunger 126 inserts relative to the handle 121 with the protrusion 143 thereof residing nearer to the fastener 124 of the first arm 122 and the fastener 125 of the second arm 122. Moreover, the lower, intermediate, or upper stop 145- 147, due to the resiliency thereof, exits the pocket 150 with the ramp 151 at the distal end 149 positioned exterior of the aperture 130 whereby the ramp 151 through contact with the center section 127 prevents a pulling on the head 141 of the plunger 126 from retracting the plunger 126 relative to the handle 121. The plunger 126 includes a length 152 whereby, during insertion of the plunger 126 relative to the handle 121, the plunger 126 will seat atop the implant 11 when the center section 127 of the handle 121 resides above one of the lower, intermediate, or upper stops 145-147.

Retraction of the plunger 126 relative to the handle 121 includes rotating the plunger 126 relative to the handle 121 until the ramps 150 of the lower, intermediate, and upper stops 145-147 align with the elongation 131 of the aperture 131. Upon alignment of the lower, intermediate, and upper stops 145-147 align with the elongation 131, a pulling on the head 141 of the plunger 126 draws the plunger 126 back relative to the handle 121 on the basis the elongation 131, which is larger than the ramps 151, allows the ramps 151 to pass through the aperture 130 such that the plunger 126 retracts relative to the handle 121 with the protrusion 143 thereof residing farther from the fastener 124 of the first arm 122 and the fastener 125 of the second arm 122. One of ordinary skill in the art will recognize that an elastic device such as a spring inserted between the handle 121 and the head 141 of the plunger will assist in the retraction of the plunger 126 relative to the handle 121.

Forming the orthopedic fixation system 10 includes the implant retainer 120 manipulated whereby the plunger 126 is retracted relative to the handle 121 with the protrusion 143 thereof spaced apart from the fastener 124 of the first arm 122 and the fastener 125 of the second arm 122. Addition- ally, the first arm 122 and the second arm 123 are moved respectively within the first bore 134 and the second bore 135 via rotations thereof to locate the fasteners 124 and 125 in the bypass position. The implant 11 then is mechanically deformed from the natural shape 12 to the insertion shape 13. More particularly, the implant 11 via the transition section 22 mechanically deforms to store energy while also moving the bridge 15 from the natural form 34 where the first and second ends 20 and 21 reside at the first distance 36 and the first and second apertures 28 and 29 reside at the first distance 38 to the insertion form 35 where the first and second ends 20 and 21 reside at the second distance 37 and the first and second apertures 28 and 29 reside at the second distance 39. Mechanical deformation of the implant 11 may include cooling of the implant 11 whereby the implant 11 transitions from its austenite phase to its martensite phase in order to facilitate an easier mechanical deformation of the implant 11 from the natural shape 12 to the insertion shape 13 prior to an engagement of the implant retainer 120 with the implant 11.

After mechanical deformation of the implant 11 from the natural shape 12 to the insertion shape 13, the implant retainer 120 using the handle 121 and the head 141 of the plunger 126 is positioned over the implant 11 with the first arm 122 aligned with the first aperture 28 and the second arm 123 aligned with the second aperture 29. The first arm 122 and the second arm 123 respectively align with the first aperture 28 and the second aperture 29 on the basis the first bore 134 and the second bore 135 and thus the first arm 122 and the second arm 123 reside at the distance 136 which substantially equals the second distance 39. The first arm 122 and the second arm 123 respectively insert into the first aperture 28 and the second aperture 29 until the fasteners 124 and 125 thereof bypass and then reside below the catches 32 and 33 of the first and second apertures 28 and 29. Once the fasteners 124 and 125 respectively reside below the catches 32 and 33, movements of the first and second arms 122 and 123 via rotations thereof locate the fasteners 124 and 125 in the interlock position whereby the fasteners 124 and 125 respectively align with the catches 32 and 33 for engagement therewith.

A pushing upon the head 141 of the plunger 126 while grasping the first and second handgrips 128 and 129 of the handle 121 inserts the plunger 126 relative to the handle 121. The plunger 126 progresses through the center section 127 of the handle 121 via the aperture 130, resulting in the plunger 126 at the second or bottom end 144 and thus the protrusion 143 seating atop the transition section 22 of the implant 11 between the first aperture 28 and the second aperture 29. Holding the handle 121 and pushing upon the plunger 126, which is seated atop the transition section 22 of the implant 11, continues until the fasteners 124 and 125 respectively abut and then tighten against the catches 32 and 33. The plunger 126 during the insertion thereof sequentially bypasses the lower stop 145, the intermediate stop 146, and the upper stop 147 until the fasteners 124 and 125 respectively abut and then tighten against the catches 32 and 33. Consequently, one of the lower, intermediate, or upper stops 145-147 resides below the center section 127 of the handle 121 such that the ramp 151 thereof prevents the plunger 126 from retracting relative to the handle 121, thereby maintaining the fasteners 124 and 125 respectively tightened against the catches 32 and 33. In accordance therewith, holding the handle 121 and inserting the plunger 126 until the fasteners 124 and 125 respectively tighten against the catches 32 and 33 in combination with one of the lower, intermediate, or upper stops 145-147 preventing a retraction of the plunger 126 secures the implant retainer 120 with the implant 11 whereby the implant retainer 120 constrains the implant 11 in the insertion shape 13 and precludes the implant 11 from returning to the natural shape 12. After constraining the implant 11 in the insertion shape 13, drill guides may be secured with the implant 11 using the first and second openings 24 and 25 thereof in order to assist in the drilling of holes into bone, bones, or bone pieces.

In an alternative forming of the orthopedic fixation system 10, the implant retainer 120 may be utilized to mechanically deform the implant 11 from the natural shape 12 to the insertion shape 13. The first arm 122 and the second arm 123 with the fasteners 124 and 125 thereof in the bypass position respectively insert into the first aperture 28 and the second aperture 29 of the implant 11 until the fasteners 124 and 125 bypass and then reside below the catches 32 and 33 of the first and second apertures 28 and 29. Although the implant 11 resides in the natural shape 12, the first aperture 28 and the second aperture 29 are sized to ensure receipt therein respectively of the fasteners 124 and 125. Once the fasteners 124 and 125 respectively reside below the catches 32 and 33, movements of the first and second arms 122 and 123 via rotations thereof locate the fasteners 124 and 125 in the interlock position whereby the fasteners 124 and 125 respectively align with the catches 32 and 33 for engagement therewith.

Holding the handle 121 and pushing upon the plunger 126, which seats atop the transition section 22 of the implant 11, positions the fasteners 124 and 125 respectively in abutting relationship with the catches 32 and 33. Continued pushing upon the plunger 126, which remains seated atop the transition section 22 of the implant 11, tightens the fasteners 124 and 125 against the catches 32 and 33. Moreover, the plunger 126 and the fasteners 124 and 125, due to the engagements thereof with the implant 11, apply a force to the implant 11 that facilitates transition of the implant 11 from the natural shape 12 to the insertion shape 13. More particularly, the implant 11 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Once the implant 11 transitions to the insertion shape 13, one of the lower, intermediate, or upper stops 145-147 residing below the center section 127 of the handle 121 prevents the plunger 126 from retracting relative to the handle 121 whereby the implant retainer 120, which is secured with the implant 11, constrains the implant 11 in the insertion shape 13 and precludes the implant 11 from returning to the natural shape 12. After constraining the implant 11 in the insertion shape 13, drill guides may be secured with the implant 11 using the first and second openings 24 and 25 thereof in order to assist in the drilling of holes into bone, bones, or bone pieces.

In accordance with the orthopedic fixation system 10, the implant retainer 120, when engaged with the implant 11 as previously described, retains the implant 11 in the insertion shape 13 such that the implant 11 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the implant retainer 120 then places the implant 11 across the first bone and the second bone with the transition section 22 of the bridge 15 located at the fixation zone. Upon placement of the implant 11 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 11. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 11 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 11 at the anchoring segment 27 with the second bone.

In light of the affixation of the implant 11 with the first and second bones across the fixation zone, the surgeon removes the implant retainer 120 from the implant 11. The surgeon rotates the plunger 126 relative to the handle 121 until the ramps 150 of the lower, intermediate, and upper stops 145-147 align with the elongation 131 of the aperture 131 and then draws the plunger 126 back relative to the handle 121. The surgeon further rotates the fasteners 124 and 125 from the interlock position to the bypass position in order to disengage the fasteners 124 and 125 respectively from the catches 32 and 33. The surgeon finally removes the first and second arms 122 and 123 respectively from the first and second apertures 28 and 29 thereby separating the implant retainer 120 from the implant 11. Upon the separation of the implant retainer 120 from the implant 11, the implant 11 attempts transition from the insertion shape 13 to the natural shape 12 whereby the implant 11 delivers the energy stored in the transition section 22 to the first bone and the second bone, resulting in the implant 11 affixing the first bone and the second bone through an application of a compressive force to the fixation zone. The implant retainer 120 accordingly improves insertion of the implant 11 because the implant retainer 120 does not release its constraint of the implant 11 until the implant 11 is affixed to the first and second bones with its transition section 22 located across the fixation zone thereof such that the implant retainer 120 prevents the implant 11 from prematurely delivering the energy stored therein to the first and second bones at the fixation zone thereof.

The implant retainer 120 according to the second embodiment may be utilized with the orthopedic implant 80 according to the fourth embodiment and the alternative of the fourth embodiment to form the orthopedic fixation system 10. The implant 80 includes the bridge 15 and the first and second apertures 28 and 29 and the catches 32 and 33 thereof substantially, completely identical to the implant 11. In accordance therewith, the implant retainer 120 engages with and disengages from the implant 80 as previously set forth with respect to the implant 11. When securing the implant 80 with bone, bones, or bone pieces, and, in particular, with a first bone and a second bone, the drill holes formed in the first and second bones respectively receive therein the first and second legs 87 and 88 of the implant 80 located in the insertion position 92 prior to the implant retainer 120 releasing the implant 80 for attempted transition from the insertion shape 82 to the natural shape 81 whereby the implant 80 delivers the energy stored in the transition section 22 to the first bone and the second bone, resulting in the implant 80 affixing the first bone and the second bone through an application of a compressive force thereto. The inclusion of the first and second apertures 28 and 29 and the catches 32 and 33 thereof in the implant 80 improves implantation of the implant 80 because the engagement of the implant retainer 120 with the implant 80 at the first and second apertures 28 and 29 and the catches 32 and 33 thereof permits implanting of the implant 80 in the insertion position 82 into bone, bones, or bone pieces using the implant retainer 120 without having to tamp the implant 80 after removal of the implant retainer 120.

FIGS. 9A-9D illustrate an implant retainer 155 according to a third embodiment and the orthopedic implant 11 according to the first embodiment utilized in forming the orthopedic fixation system 10. The implant retainer 155 in the third embodiment comprises forceps 156 including fasteners 157 and 158, each of which is configured to engage the implant 11. The fasteners 157 and 158 in the third embodiment face outward relative to the forceps 156. The fasteners 157 and 158 and the first aperture 28 and the second aperture 29 of the implant 11 are correspondingly sized such that the fasteners 157 and 158 insert into one of the first aperture 28 and the second aperture 29 while bypassing the respective catch 32 or 33 thereof. Once the fasteners 157 and 158 respectively bypass the catches 32 and 33, actuation of the forceps 156, as will be described more fully herein, locates the fasteners 157 and 158 in an interlock position whereby the fasteners 157 and 158 respectively engage the catches 32 and 33 in order to maintain the forceps 156 secured with the implant 11. The fasteners 157 and 158 are sized to reside below and respectively engage the catches 32 and 33 without extending past the lower surface 17 of the bridge 15 for the implant 11. Although the fasteners 157 and 158 face outward in the third embodiment for engagement with the implant 11 according to the first embodiment, one of ordinary skill in the art will recognize the fasteners 157 and 158 in an alternative embodiment may face inward for engagement with the implant 11 according to the alternative of the first embodiment. The forceps 156 include a stabilizer 159 extending therefrom between the fasteners 157 and 158 whereby, the stabilizer 159, when the fasteners 157 and 158 engage with the implant 11, seats atop the transition section 22 of the implant 11 between the first aperture 28 and the second aperture 29. The stabilizer 159 stabilizes the forceps 156 seated atop the transition section 22 of the implant 11 and further tightens the fasteners 157 and 158 respectively against the catches 32 and 33 such that the forceps 156 remain secured with the implant 11.

The forceps 156 include handles 160 and 161, which, in the third embodiment comprise ring handles, and a locking ratchet 162 extending between the handles 160 and 161 whereby the locking ratchet 162 is configured to arrest the movement of the handles 160 and 161 thereby locking the forceps 156 in engagement with the implant 11. The forceps 156 include shanks 163 and 164 extending respectively from the handles 160 and 161 at an angle 165 that produces a convergence thereof. The shanks 163 and 164 at the convergence thereof incorporate a hinge 166 that secures the shanks 163 and 164 together and further functions as a pivot point for the forceps 156. The forceps 156 include blades 167 and 168 terminating respectively in the fasteners 157 and 158, which, in the third embodiment, extend respectively outward substantially perpendicular from the blades 167 and 168. The blades 167 and 168 extend respectively from the shanks 163 and 168 while diverging therefrom such that the blade 167 locates the fastener 157 in a position corresponding with the handle 160 and the blade 168 locates the fastener 158 in a position corresponding with the handle 161. The blades 167 and 168 respectively diverge from the shanks 163 and 168 in order to locate the fasteners 157 and 158 spaced apart such that the fasteners 157 and 158 insert into one of the first and second apertures 28 and 29. The stabilizer 159 at a proximal end 169 extends between the blades 167 and 168 from the shank 164 at the segment of the shank 164 incorporating the hinge 166 to a distal end 170 including a foot 171. In the third embodiment, the stabilizer 159 resides above the fasteners 157 and 158 in order for the fasteners 157 and 158 to insert into one of the first aperture 28 and the second aperture 29. Moreover, the stabilizer 159 includes an offset toward the blade 167 such that, upon movement of the fasteners 157 and 158 respectively in engagement with the catches 32 and 33, the foot 171 at the distal end 170 of the stabilizer 159 seats flush atop the transition section 22 of the implant 11 between the first aperture 28 and the second aperture 29. Actuation of the forceps 156, as will be described more fully herein, includes a manipulation of the handles 160 and 161 resulting in the stabilizer 159 seating atop the implant 11 and the fasteners 157 and 158 respectively engaging the catches 32 and 33 followed by a locking of the forceps 156 via the locking ratchet 162. In the third embodiment, manipulation of the handles 160 and 161 consists of closing the handles 160 and 161 and thus the forceps 156 until the fasteners 157 and 158 respectively engaging the catches 32 and 33.

Forming the orthopedic fixation system 10 includes mechanically deforming the implant 11 from the natural shape 12 to the insertion shape 13. More particularly, the implant 11 via the transition section 22 mechanically deforms to store energy while also moving the bridge 15 from the natural form 34 where the first and second ends 20 and 21 reside at the first distance 36 and the first and second apertures 28 and 29 reside at the first distance 38 to the insertion form 35 where the first and second ends 20 and 21 reside at the second distance 37 and the first and second apertures 28 and 29 reside at the second distance 39. Mechanical deformation of the implant 11 may include cooling of the implant 11 whereby the implant 11 transitions from its austenite phase to its martensite phase in order to facilitate an easier mechanical deformation of the implant 11 from the natural shape 12 to the insertion shape 13 prior to an engagement of the implant retainer 155 with the implant 11.

After mechanical deformation of the implant 11 from the natural shape 12 to the insertion shape 13, the forceps 156 through a manipulation of the handles 160 and 161 locate the fasteners 157 and 158 spaced apart substantially equal to the second distance 39. The fasteners 157 and 158 respectively insert into the first aperture 28 and the second aperture 29 until the fasteners 157 and 158 thereof bypass and then reside below the catches 32 and 33 of the first and second apertures 28 and 29. Once the fasteners 157 and 158 respectively reside below the catches 32 and 33, an actuation of the forceps 156, which includes a manipulation of the handles 160 and 161 through a closing thereof via squeezing, pivots the fasteners 157 and 158 outward in the third embodiment and respectively into an abutting relationship with the catches 32 and 33. Squeezing of the forceps 156 continues until the stabilizer 159 at the foot 171 pivots to seat atop the transition section 22 of the implant 11 between the first aperture 28 and the second aperture 29 such that the fasteners 157 and 158 respectively tighten against the catches 32 and 33 for engagement therewith. Upon the seating of the stabilizer 159 and the tightening of the fasteners 157 and 158 respectively against the catches 32 and 33, an engagement of the locking ratchet 162 locks the forceps 156 and prevents a release thereof from the implant 11. The locking of the forceps 156 at the stabilizer 159 and the fasteners 157 and 158 thereof with the implant 11 secures the forceps 156 with the implant 11 whereby the forceps 156 constrain the implant 11 in the insertion shape 13 and preclude the implant 11 from returning to the natural shape 12. After constraining the implant 11 in the insertion shape 13, drill guides may be secured with the implant 11 using the first and second openings 24 and 25 thereof in order to assist in the drilling of holes into bone, bones, or bone pieces.

In an alternative forming of the orthopedic fixation system 10, the forceps 156 may be utilized to mechanically deform the implant 11 from the natural shape 12 to the insertion shape 13. The forceps 156 through a manipulation of the handles 160 and 161 locate the fasteners 157 and 158 spaced apart whereby the fasteners 157 and 158 respectively insert into the first aperture 28 and the second aperture 29 of the implant 11 until the fasteners 157 and 158 bypass and then reside below the catches 32 and 33 of the first and second apertures 28 and 29. Although the implant 11 resides in the natural shape 12, the first aperture 28 and the second aperture 29 are sized to ensure receipt therein respectively of the fasteners 157 and 158. Once the fasteners 157 and 158 respectively reside below the catches 32 and 33, an actuation of the forceps 156, which includes a manipulation of the handles 160 and 161 through a closing thereof via squeezing, pivots the fasteners 157 and 158 outward in the third embodiment and respectively into an abutting relationship with the catches 32 and 33. Squeezing of the forceps 156 continues until the stabilizer 159 at the foot 171 pivots to seat atop the transition section 22 of the implant 11 between the first aperture 28 and the second aperture 29 such that the fasteners 157 and 158 respectively tighten against the catches 32 and 33 for engagement therewith. Continued squeezing of the forceps 156 applies a force to the implant 11 that facilitates transition of the implant 11 from the natural shape 12 to the insertion shape 13. More particularly, the implant 11 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Once the implant 11 transitions to the insertion shape 13, an engagement of the locking ratchet 162 locks the forceps 156 and prevents a release thereof from the implant 11. The locking of the forceps 156 at the stabilizer 159 and the fasteners 157 and 158 thereof with the implant 11 secures the forceps 156 with the implant 11 whereby the forceps 156 constrain the implant 11 in the insertion shape 13 and preclude the implant 11 from returning to the natural shape 12. After constraining the implant 11 in the insertion shape 13, drill guides may be secured with the implant 11 using the first and second openings 24 and 25 thereof in order to assist in the drilling of holes into bone, bones, or bone pieces.

In accordance with the orthopedic fixation system 10, the forceps 156, when engaged with the implant 11 as previously described, retains the implant 11 in the insertion shape 13 such that the implant 11 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the forceps 156 then places the implant 11 across the first bone and the second bone with the transition section 22 of the bridge 15 located at the fixation zone. Upon placement of the implant 11 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 11. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 11 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 11 at the anchoring segment 27 with the second bone.

In light of the affixation of the implant 11 with the first and second bones across the fixation zone, the surgeon removes the forceps 156 from the implant 11. The surgeon releases the locking ratchet 162 and manipulates the handles 160 and 161 through an opening thereof, causing the fasteners 157 and 158 to pivot inward in the third embodiment and respectively out of abutting relationship with the catches 32 and 33. After release respectively from the catches 32 and 33, the surgeon via the handles 160 and 161 withdraws the fasteners 157 and 158 respectively from the first and second apertures 28 and 29 and the stabilizer 159 from atop the transition section 22 of the implant 11, thereby separating the forceps 156 from the implant 11. Upon the separation of the forceps 156 from the implant 11, the implant 11 attempts transition from the insertion shape 13 to the natural shape 12 whereby the implant 11 delivers the energy stored in the transition section 22 to the first bone and the second bone, resulting in the implant 11 affixing the first bone and the second bone through an application of a compressive force to the fixation zone. The forceps 156 accordingly improve insertion of the implant 11 because the forceps 156 do not release constraint of the implant 11 until the implant 11 is affixed to the first and second bones with its transition section 22 located across the fixation zone thereof such that the forceps 156 prevent the implant 11 from prematurely delivering the energy stored therein to the first and second bones at the fixation zone thereof.

The implant retainer 155 according to the third embodiment, which comprises the forceps 156, may be utilized with the orthopedic implant 80 according to the fourth embodiment and the alternative of the fourth embodiment to form the orthopedic fixation system 10. The implant 80 includes the bridge 15 and the first and second apertures 28 and 29 and the catches 32 and 33 thereof substantially, completely identical to the implant 11. In accordance therewith, the forceps 156 engage with and disengage from the implant 80 as previously set forth with respect to the implant 11. When securing the implant 80 with bone, bones, or bone pieces, and, in particular, with a first bone and a second bone, the drill holes formed in the first and second bones respectively receive therein the first and second legs 87 and 88 of the implant 80 located in the insertion position 92 prior to the forceps 156 releasing the implant 80 for attempted transition from the insertion shape 82 to the natural shape 81 whereby the implant 80 delivers the energy stored in the transition section 22 to the first bone and the second bone, resulting in the implant 80 affixing the first bone and the second bone through an application of a compressive force thereto. The inclusion of the first and second apertures 28 and 29 and the catches 32 and 33 thereof in the implant 80 improves implantation of the implant 80 because the engagement of the implant retainer 155 with the implant 80 at the first and second apertures 28 and 29 and the catches 32 and 33 thereof permits implanting of the implant 80 in the insertion position 82 into bone, bones, or bone pieces using the implant retainer 155 without having to tamp the implant 80 after removal of the implant retainer 155.

FIGS. 10A-10D illustrate an implant retainer 175 according to a fourth embodiment and the orthopedic implant 11 according to the alternative of the first embodiment utilized in forming the orthopedic fixation system 10. The implant retainer 175 in the fourth embodiment comprises forceps 176 including fasteners 177 and 178, each of which is configured to engage the implant 11. The fasteners 177 and 178 in the fourth embodiment face inward relative to the forceps 176. The fasteners 177 and 178 and the first aperture 28 and the second aperture 29 of the implant 11 are correspondingly sized such that the fasteners 177 and 178 insert into one of the first aperture 28 and the second aperture 29 while bypassing the respective catch 32 or 33 thereof. Once the fasteners 177 and 178 respectively bypass the catches 32 and 33, actuation of the forceps 176, as will be described more fully herein, locates the fasteners 177 and 178 in an interlock position whereby the fasteners 177 and 178 respectively engage the catches 32 and 33 in order to maintain the forceps 176 secured with the implant 11. The fasteners 177 and 178 are sized to reside below and respectively engage the catches 32 and 33 without extending past the lower surface 17 of the bridge 15 for the implant 11. Although the fasteners 177 and 178 face inward in the fourth embodiment for engagement with the implant 11 according to the alternative of the first embodiment, one of ordinary skill in the art will recognize the fasteners 177 and 178 in an alternative embodiment may face outward for engagement with the implant 11 according to the first embodiment. The forceps 176 include a stabilizer 179 extending therefrom between the fasteners 177 and 178 whereby, the stabilizer 179, when the fasteners 177 and 178 engage with the implant 11, seats atop the transition section 22 of the implant 11 between the first aperture 28 and the second aperture 29. The stabilizer 179 stabilizes the forceps 176 seated atop the transition section 22 of the implant 11 and further tightens the fasteners 177 and 178 respectively against the catches 32 and 33 such that the forceps 176 remain secured with the implant 11.

The forceps 176 include handles 180 and 181 and a locking ratchet 182 extending between the handles 180 and 181 whereby the locking ratchet 182 is configured to arrest the movement of the handles 180 and 181 thereby locking the forceps 176 in engagement with the implant 11. The forceps 176 include shanks 183 and 184 extending respectively from the handles 180 and 181 at an angle 185 that produces a convergence thereof. The shanks 183 and 184 at the convergence thereof incorporate a hinge 186 that secures the shanks 183 and 184 together and further functions as a pivot point for the forceps 176. The forceps 176 include blades 187 and 188 terminating respectively in the fasteners 178 and 177, which, in the fourth embodiment, extend respectively inward substantially perpendicular from the blades 187 and 188. The blades 187 and 188 extend respectively from the shanks 183 and 184 along the angle 185 in a traversal of the hinge 186 such that the blade 187 locates the fastener 178 positionally opposite relative to the handle 180 and the blade 188 locates the fastener 177 positionally opposite relative to the handle 181. Although the blades 187 and 188 initially extend respectively from the shanks 183 and 184 along the angle 185, the blades 187 and 188 curve inward in order to locate the fasteners 177 and 178 spaced apart such that the fasteners 177 and 178 insert into one of the first and second apertures 28 and 29. The stabilizer 179 at a proximal end 189 extends between the blades 187 and 188 from the shank 183 at the segment of the shank 183 incorporating the hinge 186 to a distal end 190 including a foot 191. In the fourth embodiment, the stabilizer 179 resides above the fasteners 177 and 178 in order for the fasteners 177 and 178 to insert into one of the first aperture 28 and the second aperture 29. Moreover, the stabilizer 179 includes an offset toward the blade 187 such that, upon movement of the fasteners 177 and 178 respectively in engagement with the catches 32 and 33, the foot 191 at the distal end 190 of the stabilizer 179 seats flush atop the transition section 22 of the implant 11 between the first aperture 28 and the second aperture 29. Actuation of the forceps 176, as will be described more fully herein, includes a manipulation of the handles 180 and 181 resulting in the stabilizer 179 seating atop the implant 11 and the fasteners 177 and 178 respectively engaging the catches 32 and 33 followed by a locking of the forceps 176 via the locking ratchet 182. In the fourth embodiment, manipulation of the handles 180 and 181 consists of closing the handles 180 and 181 and thus the forceps 176 until the fasteners 177 and 178 respectively engaging the catches 32 and 33.

Forming the orthopedic fixation system 10 includes mechanically deforming the implant 11 from the natural shape 12 to the insertion shape 13. More particularly, the implant 11 via the transition section 22 mechanically deforms to store energy while also moving the bridge 15 from the natural form 34 where the first and second ends 20 and 21 reside at the first distance 36 and the first and second apertures 28 and 29 reside at the first distance 38 to the insertion form 35 where the first and second ends 20 and 21 reside at the second distance 37 and the first and second apertures 28 and 29 reside at the second distance 39. Mechanical deformation of the implant 11 may include cooling of the implant 11 whereby the implant 11 transitions from its austenite phase to its martensite phase in order to facilitate an easier mechanical deformation of the implant 11 from the natural shape 12 to the insertion shape 13 prior to an engagement of the implant retainer 175 with the implant 11.

After mechanical deformation of the implant 11 from the natural shape 12 to the insertion shape 13, the forceps 176 through a manipulation of the handles 180 and 181 locate the fasteners 177 and 178 spaced apart substantially equal to the second distance 39. The fasteners 177 and 178 respectively insert into the first aperture 28 and the second aperture 29 until the fasteners 177 and 178 thereof bypass and then reside below the catches 32 and 33 of the first and second apertures 28 and 29. Once the fasteners 177 and 178 respectively reside below the catches 32 and 33, an actuation of the forceps 176, which includes a manipulation of the handles 180 and 181 through a closing thereof via squeezing, pivots the fasteners 177 and 178 inward in the fourth embodiment and respectively into an abutting relationship with the catches 32 and 33. Squeezing of the forceps 176 continues until the stabilizer 179 at the foot 191 pivots to seat atop the transition section 22 of the implant 11 between the first aperture 28 and the second aperture 29 such that the fasteners 177 and 178 respectively tighten against the catches 32 and 33 for engagement therewith. Upon the seating of the stabilizer 179 and the tightening of the fasteners 177 and 178 respectively against the catches 32 and 33, an engagement of the locking ratchet 182 locks the forceps 176 and prevents a release thereof from the implant 11. The locking of the forceps 176 at the stabilizer 179 and the fasteners 177 and 178 thereof with the implant 11 secures the forceps 176 with the implant 11 whereby the forceps 176 constrain the implant 11 in the insertion shape 13 and preclude the implant 11 from returning to the natural shape 12. After constraining the implant 11 in the insertion shape 13, drill guides may be secured with the implant 11 using the first and second openings 24 and 25 thereof in order to assist in the drilling of holes into bone, bones, or bone pieces.

In accordance with the orthopedic fixation system 10, the forceps 176, when engaged with the implant 11 as previously described, retains the implant 11 in the insertion shape 13 such that the implant 11 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the forceps 176 then places the implant 11 across the first bone and the second bone with the transition section 22 of the bridge 15 located at the fixation zone. Upon placement of the implant 11 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 11. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 11 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 11 at the anchoring segment 27 with the second bone.

In light of the affixation of the implant 11 with the first and second bones across the fixation zone, the surgeon removes the forceps 176 from the implant 11. The surgeon releases the locking ratchet 182 and manipulates the handles 180 and 181 through an opening thereof, causing the fasteners 177 and 178 to pivot outward in the fourth embodiment and respectively out of abutting relationship with the catches 32 and 33. After release respectively from the catches 32 and

33, the surgeon via the handles 180 and 181 withdraws the fasteners 177 and 178 respectively from the first and second apertures 28 and 29 and the stabilizer 179 from atop the transition section 22 of the implant 11, thereby separating the forceps 176 from the implant 11. Upon the separation of the forceps 176 from the implant 11, the implant 11 attempts transition from the insertion shape 13 to the natural shape 12 whereby the implant 11 delivers the energy stored in the transition section 22 to the first bone and the second bone, resulting in the implant 11 affixing the first bone and the second bone through an application of a compressive force to the fixation zone. The forceps 176 accordingly improve insertion of the implant 11 because the forceps 176 do not release constraint of the implant 11 until the implant 11 is affixed to the first and second bones with its transition section 22 located across the fixation zone thereof such that the forceps 176 prevent the implant 11 from prematurely delivering the energy stored therein to the first and second bones at the fixation zone thereof.

The implant retainer 175 according to the fourth embodiment, which comprises the forceps 176, may be utilized with the orthopedic implant 80 according to the fourth embodiment and the alternative of the fourth embodiment to form the orthopedic fixation system 10. The implant 80 includes the bridge 15 and the first and second apertures 28 and 29 and the catches 32 and 33 thereof substantially, completely identical to the implant 11. In accordance therewith, the forceps 176 engage with and disengage from the implant 80 as previously set forth with respect to the implant 11. When securing the implant 80 with bone, bones, or bone pieces, and, in particular, with a first bone and a second bone, the drill holes formed in the first and second bones respectively receive therein the first and second legs 87 and 88 of the implant 80 located in the insertion position 92 prior to the forceps 176 releasing the implant 80 for attempted transition from the insertion shape 82 to the natural shape 81 whereby the implant 80 delivers the energy stored in the transition section 22 to the first bone and the second bone, resulting in the implant 80 affixing the first bone and the second bone through an application of a compressive force thereto. The inclusion of the first and second apertures 28 and 29 and the catches 32 and 33 thereof in the implant 80 improves implantation of the implant 80 because the engagement of the implant retainer 175 with the implant 80 at the first and second apertures 28 and 29 and the catches 32 and 33 thereof permits implanting of the implant 80 in the insertion position 82 into bone, bones, or bone pieces using the implant retainer 175 without having to tamp the implant 80 after removal of the implant retainer 175.

FIG. 11 illustrates an implant retainer 195 according to a fifth embodiment. The implant retainer 195 includes a first retention block 196 configured to engage a drill guide. Similarly, the implant retainer 195 includes a second retention block 197 configured to engage a drill guide. The implant retainer 195 includes a fastener in the form of a set screw 198 having a head 199 and a shank 200 with threads whereby the set screw 198 is configured to secure the first retention block 196 with the second retention block 197 while the first retention block 196 and the second retention block 197 engage drill guides.

The first retention block 196 as illustrated in FIGS. 12A-12C preferably is three-dimensional in form including a front 201 defining a block interface 202, a rear 203, a top 204, a bottom 205, a first side 206, and a second side 207. The first retention block 196 may be manufactured from any suitable rigid material, including but not limited to biocompatible metal or metal alloy, such as, for example, titanium, stainless steel, titanium alloy, and cobalt chrome alloy. The block interface 202 in the fifth embodiment slopes from the top 204 to the bottom 205 following an angle 208, which is acute in the fifth embodiment, such that the top 204 in the fifth embodiment is longer than the bottom 205. The first retention block 196 adjacent the second end 203 includes an aperture 209 extending therethrough from the upper surface 204 to the lower surface 205. The aperture 209 is sized and includes a diameter whereby the aperture 209 receives therethrough a drill guide while maintaining a frictional engagement therewith. The first retention block 196 includes a bore 210 extending therethrough along a pathway from the top 204 to the block interface 202. The bore 210, due to the pathway thereof that angles from the top 204 to the block interface 202, is configured to engage the set screw 198 thereby securing the set screw 198 with the first retention block 196 while allowing the set screw 198 to extend from the first retention block 196 at the block interface 202 for securing with the second retention block 197. The bore 210 includes a countersink 211 configured to receive therein the head 199 of the set screw 198 such that the head 199 resides below the top 204 of the first retention block 196. The bore 210 between the countersink 211 and the block interface 202 includes threads that correspond with the threads on the shaft 200 of the set screw 198 in order for the bore 210 to engage with the set screw 198.

The second retention block 197 as illustrated in FIGS. 13A-13C preferably is three-dimensional in form including a front 211 defining a block interface 213, a rear 214, a top 215, a bottom 216, a first side 217, and a second side 218. The second retention block 197 may be manufactured from any suitable rigid material, including but not limited to biocompatible metal or metal alloy, such as, for example, titanium, stainless steel, titanium alloy, and cobalt chrome alloy. The block interface 213 in the fifth embodiment slopes from the top 215 to the bottom 216 following an angle 219, which is obtuse in the fifth embodiment, such that the top 215 in the fifth embodiment is shorter than the bottom 216. The second retention block 197 adjacent the second end 214 includes an aperture 220 extending therethrough from the upper surface 215 to the lower surface 216. The aperture 220 is sized and includes a diameter whereby the aperture 220 receives therethrough a drill guide while maintaining a frictional engagement therewith. The second retention block 197 includes a bore 221 extending along a pathway from the block interface 213 toward the bottom 216 although the bore 221 does not exit from the second retention block 197. The bore 221, due to the pathway thereof that angles from the block interface 213 toward the bottom 216 correspondingly with the pathway of the bore 210, is configured to align with the bore 210 of the first retention block 196 when the block interface 202 of the first retention block 196 aligns with the block interface 213 of the second retention block 197. In accordance therewith, the bore 221, when the set screw 198 extends from the first retention block 196 at the block interface 202, engages with the set screw 198 thereby securing the set screw 198 with the second retention block 197 and further the first retention block 196 with the second retention block 197. The bore 221 includes threads that correspond with the threads on the shaft 200 of the set screw 198 in order for the bore 221 to engage with the set screw 198.

Figure 14A:
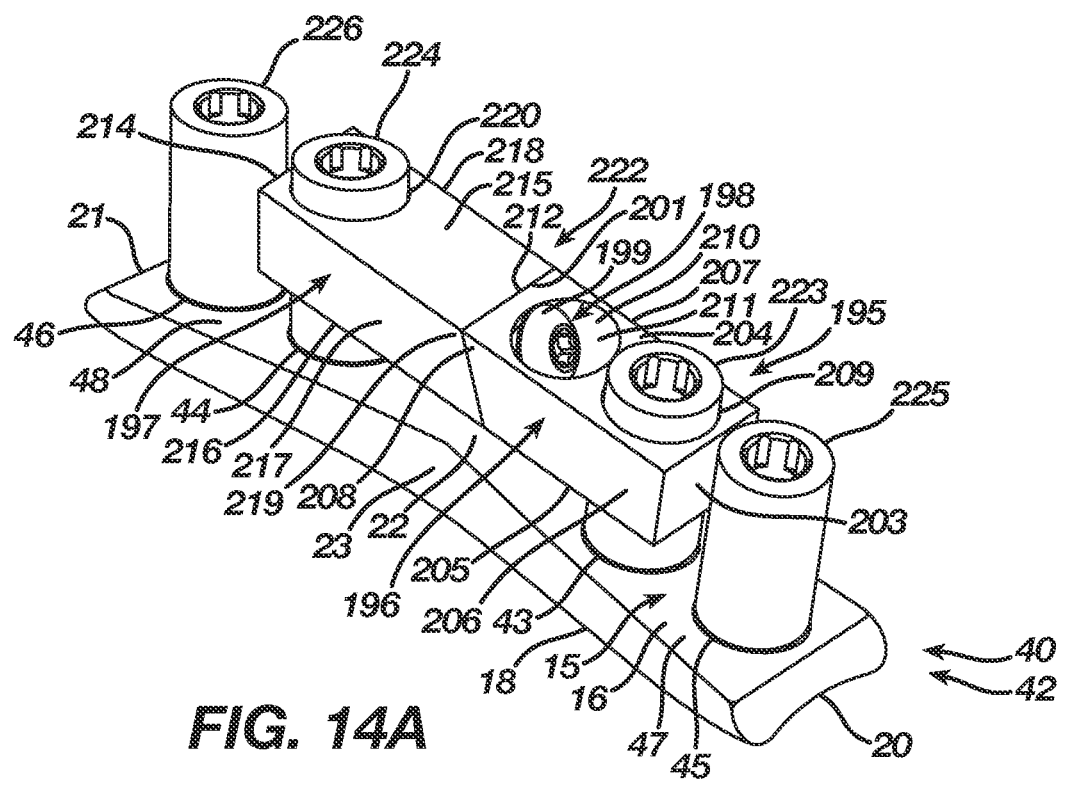
FIG. 14A is a top isometric view illustrating the implant retainer according to the fifth embodiment and the orthopedic implant according to the second embodiment in the insertion shape forming the orthopedic fixation system.
Figure 14B:
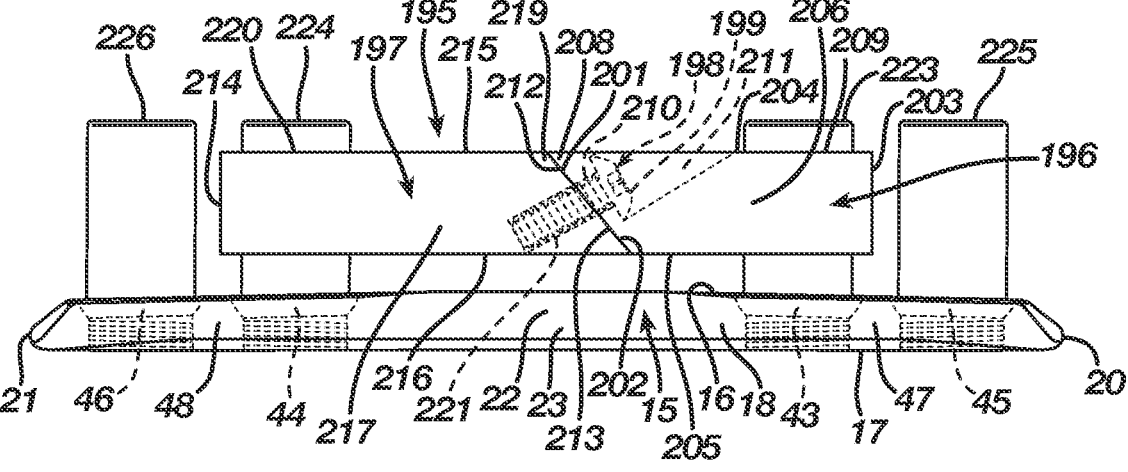
FIG. 14B is a front view illustrating the implant retainer according to the fifth embodiment and the orthopedic implant according to the second embodiment in the insertion shape forming the orthopedic fixation system.

FIGS. 14A-14B illustrate the orthopedic fixation system 10 including the implant retainer 195 according to the fifth embodiment and the orthopedic implant 40 according to the second embodiment. The first retention block 196 and the second retention block 197 according to the fifth embodiment are designed with respect to size, shape, and a distance 222 between the aperture 209 of the first retention block 196 and the aperture 220 of the second retention block 197 whereby, when the first retention block 196 is coupled with the second retention block 197 using the set screw 198, the distance 222 substantially, completely equals the distance 49 between the first and second openings 43 and 44 of the implant 40 when the implant 40 resides in the insertion shape 42. The distance 222 substantially, completely equals the distance 49 in order for the first and second retention blocks 196 and 197 respectively to receive therethrough drill guides coupled with the first and second openings 43 and 44 during an alignment of the block interface 202 and the bore 210 of the first retention block 196 with the block interface 213 and the bore 221 of the second retention block 197. Upon an alignment of the block interfaces 202 and 213 and thus the bores 210 and 221, an insertion of the set screw 198 into the bores 210 and 221 secures the first and second retention blocks 196 and 197 such that the implant retainer 195 constrains the implant 40 in the insertion shape 42 and prevents the implant 40 from returning to the natural shape 41. While the block interfaces 202 and 213 may be vertical, the block interfaces 202 and 213 in the fifth embodiment are oblique to prevent a binding thereof as the first retention block 196 fits over a drill guide and slides into place in abutting relationship with the second retention block 197.

Forming the orthopedic fixation system 10 includes securing first, second, third, and fourth drill guides 223, 224, 225, and 226 respectively with the first, second, third, and fourth openings 43, 44, 45, and 46. The implant 40 then is mechanically deformed from the natural shape 41 to the insertion shape 42. More particularly, the implant 40 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37 and the first and second openings 43 and 44 reside at the distance 49. Mechanical deformation of the implant 40 may include cooling of the implant 40 whereby the implant 40 transitions from its austenite phase to its martensite phase in order to facilitate an easier mechanical deformation of the implant 40 from the natural shape 41 to the insertion shape 42 prior to an engagement of the implant retainer 195 with the implant 40.

After mechanical deformation of the implant 40 from the natural shape 41 to the insertion shape 42, the second retention block 197 at the aperture 220 fits over the drill guide 224 with the block interface 213 thereof facing the transition section 22 of the implant 40. Similarly, the first retention block 196 at the aperture 209 fits over the drill guide 223 with the block interface 202 thereof facing the transition section 22 of the implant 40 until the first retention block 196 at the block interface 202 abuts the second retention block 197 at the block interface 213 and further the block interface 202 and the bore 210 of the first retention block 196 align with the block interface 213 and the bore 221 of the second retention block 197. The set screw 198 inserts into the bores 210 and 221 whereupon the shaft 200 extends through the bore 210 and into the bore 221 and the head 199 resides in the countersink 211 below the top 204 of the first retention block 196. The set screw 198 therefore connects the first retention block 196 and the second retention block 197 such that the first retention block 196 and the second retention blocks 197 span the transition section 22 of the implant 40 while also respectively engaging the drill guides 223 and 224. In accordance therewith, the implant retainer 195, on account of the connected first and second retention blocks 196 and 197 concurrently spanning the transition section 22 and respectively holding the drill guides 223 and 224, constrains the implant 40 in the insertion shape 42 thereby preventing the implant 40 from returning to the natural shape 41. When forming the orthopedic fixation system 10, the first retention block 196 and the second retention block 197 as illustrated in FIGS. 12A-12B may be spaced apart from the upper surface 16 of the implant 40 or alternatively the first retention block 196 and the second retention block 197 may seat atop the implant 40 at the upper surface 16 thereof. Moreover, one of ordinary skill in the art will recognize the first retention block 196 may engage the drill guide 224 and the second retention block 197 may engage the drill guide 223.

In accordance with the orthopedic fixation system 10, the implant retainer 195, when engaged with the implant 40 through a locking thereof with the first and second drill guides 223 and 224 as previously described, retains the implant 40 in the insertion shape 42 such that the implant 40 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the implant retainer 195 if appropriate then places the implant 40 across the first bone and the second bone with the transition section 22 of the bridge 15 located at the fixation zone. Upon placement of the implant 40, the surgeon secures the implant 40 with the first and second bones using first and second locating pins. The first locating pin inserts through the first drill guide 223 and into the first bone thereby securing the implant 40 at its anchoring segment 47 with the first bone. Likewise, the second locating pin inserts through the second drill guide 224 and into the second bone thereby securing the implant 40 at its anchoring segment 48 with the second bone. The first and second locating pins hold the implant 40 on the first and second bones with the first and second bones aligned in the orientation that promotes fixation. If desired, the surgeon may secure the first locating pin with the first drill guide 223 via a first collar coupled with the first drill guide 223 and the second locating pin with the second drill guide 224 via a second collar coupled with the second drill guide 224.

After securing the implant 40 with the first and second bones using the first and second locating pins, the surgeon creates drill holes in the first and second bones using the third and fourth drill guides 225 and 226. The surgeon inserts a drill bit through the third drill guide 225 and the third opening 45 and then utilizes the drill bit to form a drill hole in the first bone at the third opening 45. Likewise, the surgeon inserts a drill bit through the fourth drill guide 226 and the fourth opening 46 and then utilizes the drill bit to form a drill hole in the second bone at the fourth opening 46.

With a drill hole formed in the first bone at the third opening 45 and the second bone at the fourth opening 46, the surgeon removes the third drill guide 225 from the third opening 45 and inserts, via an insertion tool such as a screwdriver, an anchoring member in the form of a screw through the third opening 45 and into the first bone until the screw at a head thereof resides substantially, completely within the third opening 45, whereby the screw affixes the implant 40 at the anchoring segment 47 with the first bone. Likewise, the surgeon removes the fourth drill guide 226 from the fourth opening 46 and inserts, via an insertion tool such as a screwdriver, an anchoring member in the form of a screw through the fourth opening 46 and into the second bone until the screw at a head thereof resides substantially, completely within the fourth opening 46, whereby the screw affixes the implant 40 at the anchoring segment 48 with the second bone.

Once the surgeon affixes the implant 40 at the anchoring segment 47 with the first bone and at the anchoring segment 48 with the second bone, the surgeon creates drill holes in the first and second bones using the first and second drill guides 223 and 224. The surgeon inserts a drill bit through the first drill guide 223 and the first opening 43 and then utilizes the drill bit to form a drill hole in the first bone at the first opening 43. Likewise, the surgeon inserts a drill bit through the second drill guide 224 and the second opening 44 and then utilizes the drill bit to form a drill hole in the second bone at the second opening 44.

With drill holes formed in the first bone at the first opening 43 and the second bone at the second opening 44, the surgeon releases the implant retainer 195 and removes the implant retainer 195 from the first and second drill guides 223 and 224. More particularly, the surgeon removes the set screw 198 from the bores 210 and 221 of the first and second retention blocks 196 and 197 thereby disconnecting the first retention block 196 from the second retention block 197. Upon disconnection, the surgeon removes the first retention block 196 at the aperture 209 from the drill guide 223 and the second retention block 197 at the aperture 220 from the drill guide 224. The surgeon further removes the first drill guide 223 from the first opening 43 and inserts, via an insertion tool such as a screwdriver, an anchoring member in the form of a screw through the first opening 43 and into the first bone until the screw at a head thereof resides substantially, completely within the first opening 43, whereby the screw affixes the implant 40 at the anchoring segment 47 with the first bone. Likewise, the surgeon removes the second drill guide 224 from the second opening 44 and inserts, via an insertion tool such as a screwdriver, an anchoring member in the form of a screw through the second opening 44 and into the second bone until the screw at a head thereof resides substantially, completely within the second opening 44, whereby the screw affixes the implant 40 at the anchoring segment 48 with the second bone.

In light of the affixation of the implant 40 with the first and second bones across the fixation zone and the removal of the implant retainer 195 from engagement with the first and second drill guides 223 and 224, the implant 40 attempts transition from the insertion shape 42 to the natural shape 41 whereby the implant 40 delivers the energy stored in the transition section 22 to the first bone and the second bone, resulting in the implant 40 affixing the first bone and the second bone through an application of a compressive force to the fixation zone. The implant retainer 195 accordingly improves insertion of the implant 40 because the implant retainer 195 does not release its constraint of the implant 40 until the implant 40 is affixed to the first and second bones with its transition section 22 located across the fixation zone thereof such that the implant retainer 195 prevents the implant 40 from prematurely delivering the energy stored therein to the first and second bones at the fixation zone thereof. While the implant 40 may attempt transition from the insertion shape 42 to the natural shape 41 before a surgeon completes insertion of screws through the first and second openings 43 and 44, one of ordinary skill in the art will recognize the prior securing of the implant 40 with the first and second bones via the third and fourth openings 45 and 46 thereof ensures the first bone and the second bone at the fixation zone remain in the orientation that promotes their fixation proper healing.

The implant retainer 195 according to the fifth embodiment may be utilized with the orthopedic implant 50 according to the third embodiment to form the orthopedic fixation system 10. The implant 50 includes the first, second, third, and fourth openings 67, 68, 69, and 70, which, substantially similar to the first, second, third, and fourth openings 43, 44, 45, and 46 of the implant 40, are configured to receive therein respectively the first, second, third, and fourth drill guides 223, 224, 225, and 226. In accordance therewith, the implant retainer 195 and the first and second retention blocks 196 and 197 thereof engage with and disengage from the first and second drill guides 223 and 224 and thus the implant 50 as previously set forth with respect to the implant 40, except the implant retainer 195 is sized such that the distance 222 substantially, completely equals the distance 77 between the first and second openings 67 and 68 of the implant 50 when the implant 50 resides in the insertion shape 52. A surgeon secures the implant 50 with bone, bones, or bone pieces, and, in particular, with a first bone and a second bone using the implant retainer 195 substantially, completely identical as previously set forth with respect to the implant 40.

Figure 15:
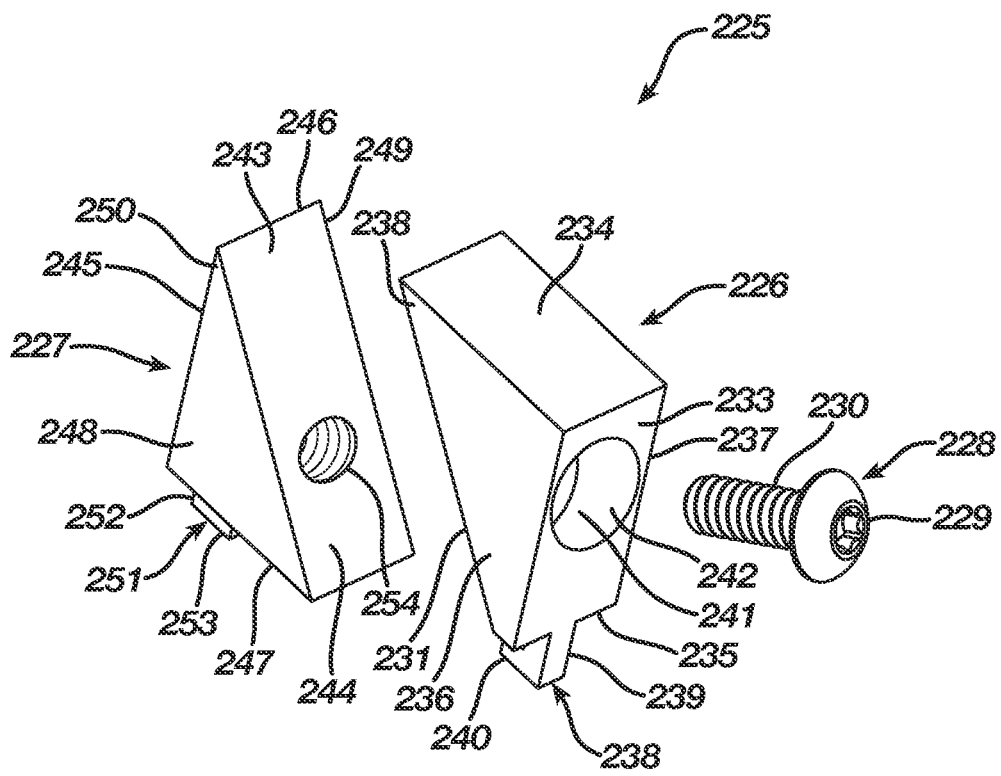
FIG. 15 is a top isometric view illustrating an implant retainer according to a sixth embodiment.

FIG. 15 illustrates an implant retainer 225 according to a sixth embodiment. The implant retainer 225 includes a first retention block 226 configured to engage the orthopedic implant 11 according to the first embodiment. Similarly, the implant retainer 225 includes a second retention block 227 configured to engage the orthopedic implant 11 according to the first embodiment. The implant retainer 225 includes a fastener in the form of a set screw 228 having a head 229 and a shank 230 with threads whereby the set screw 228 is configured to secure the first retention block 226 with the second retention block 227 while the first retention block 226 and the second retention block 227 engage the orthopedic implant 11 according to the first embodiment.

The first retention block 226 as illustrated in FIGS. 16A-16D preferably is three-dimensional in form including a front 231 defining a block interface 232, a rear 233, a top 234, a bottom 235, a first side 236, and a second side 237. The first retention block 226 may be manufactured from any suitable rigid material, including but not limited to biocompatible metal or metal alloy, such as, for example, titanium, stainless steel, titanium alloy, and cobalt chrome alloy. The block interface 232 in the sixth embodiment slopes from the top 234 to the bottom 235 following an angle 238, which is acute in the sixth embodiment, such that the top 234 in the sixth embodiment is longer than the bottom 235. The first retention block 226 includes a fastener 238 engageable with the implant 11 at one of the first aperture 28 and the second aperture 29 thereof. More particularly, the fastener 238 and the first aperture 28 and the second aperture 29 are configured and correspondingly sized whereby the fastener 238 inserts into one of the first aperture 28 and the second aperture 29 while bypassing the catches 32 or 33 thereof such that the fastener 238 resides below the catches 32 or 33 without extending past the lower surface 17 of the bridge 15 for the implant 11. The fastener 238 in the sixth embodiment extends from the bottom 235 of the first retention block 226 adjacent the rear 233 in a location central relative to the rear 233. The fastener 238 includes a post 239 extending from the bottom 235 and a detent 240 extending from the post 239 toward the block interface 232. The first retention block 226 includes a bore 241 extending therethrough along a pathway from the rear 233 to the block interface 232. The bore 241, due to the pathway thereof that angles from the rear 233 to the block interface 232, is configured to engage the set screw 228 thereby securing the set screw 228 with the first retention block 226 while allowing the set screw 228 to extend from the first retention block 226 at the block interface 232 for securing with the second retention block 227. The bore 241 includes a countersink 242 configured to receive therein the head 229 of the set screw 228 such that the head 229 resides below the rear 233 of the first retention block 226. The bore 241 between the countersink 242 and the block interface 232 includes threads that correspond with the threads on the shaft 230 of the set screw 228 in order for the bore 241 to engage with the set screw 228.

The second retention block 227 as illustrated in FIGS. 17A-17D preferably is three-dimensional in form including a front 243 defining a block interface 244, a rear 245, a top 246, a bottom 247, a first side 248, and a second side 249. The second retention block 227 may be manufactured from any suitable rigid material, including but not limited to biocompatible metal or metal alloy, such as, for example, titanium, stainless steel, titanium alloy, and cobalt chrome alloy. The block interface 244 in the sixth embodiment slopes from the top 246 to the bottom 247 following an angle 250, which is acute in the sixth embodiment, such that the top 246 in the sixth embodiment is shorter than the bottom 247. The second retention block 227 includes a fastener 251 engageable with the implant 11 at one of the first aperture 28 and the second aperture 29 thereof. More particularly, the fastener 251 and the first aperture 28 and the second aperture 29 are configured and correspondingly sized whereby the fastener 251 inserts into one of the first aperture 28 and the second aperture 29 while bypassing the catches 32 or 33 thereof such that the fastener 251 resides below the catches 32 or 33 without extending past the lower surface 17 of the bridge 15 for the implant 11. The fastener 251 in the sixth embodiment extends from the bottom 247 of the second retention block 227 adjacent the rear 245 in a location central relative to the rear 245. The fastener 251 includes a post 252 extending from the bottom 247 and a detent 253 extending from the post 252 toward the block interface 244. The second retention block 227 includes a bore 254 extending along a pathway from the block interface 244 toward the rear 245 and the bottom 247 although the bore 254 does not exit from the second retention block 227. The bore 254, due to the pathway thereof that angles from the block interface 213 toward the bottom 247 correspondingly with the pathway of the bore 241, is configured to align with the bore 241 of the first retention block 226 when the block interface 232 of the first retention block 226 aligns with the block interface 244 of the second retention block 227. In accordance therewith, the bore 254, when the set screw 228 extends from the first retention block 226 at the block interface 232, engages with the set screw 228 thereby securing the set screw 228 with the second retention block 227 and further the first retention block 226 with the second retention block 227. The bore 254 includes threads that correspond with the threads on the shaft 230 of the set screw 228 in order for the bore 254 to engage with the set screw 228.

Figure 18A:
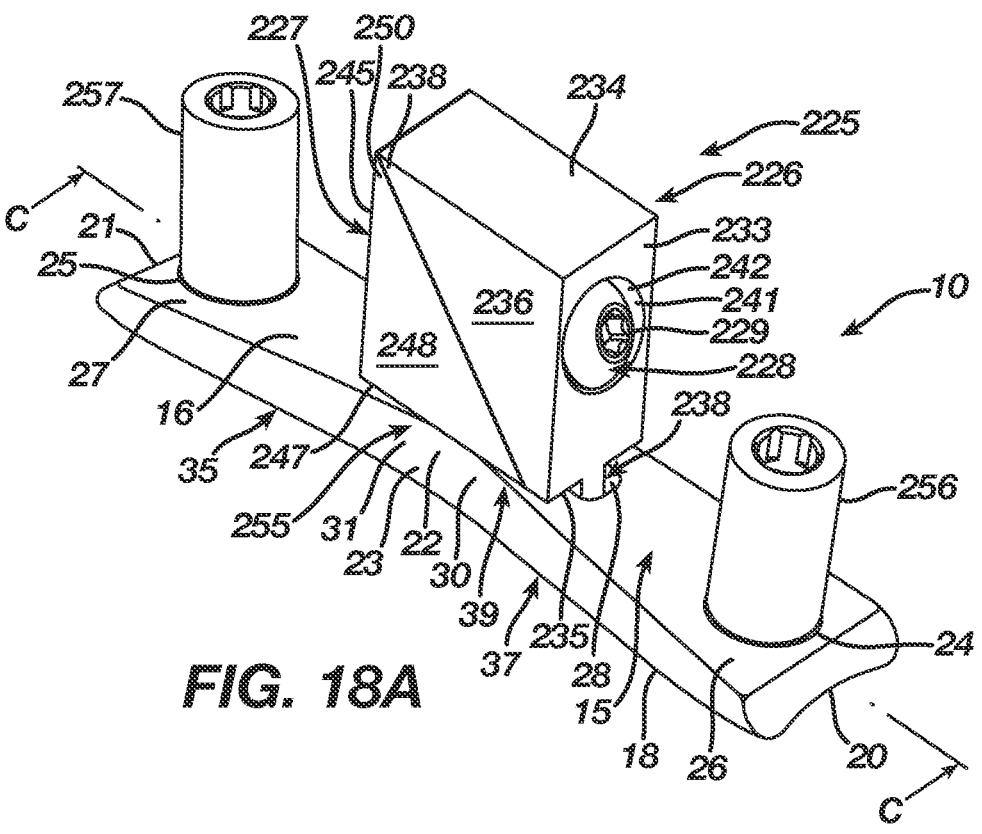
FIG. 18A is a top isometric view illustrating the implant retainer according to the sixth embodiment and the orthopedic implant according to the first embodiment in the insertion shape forming the orthopedic fixation system.
Figure 18B:
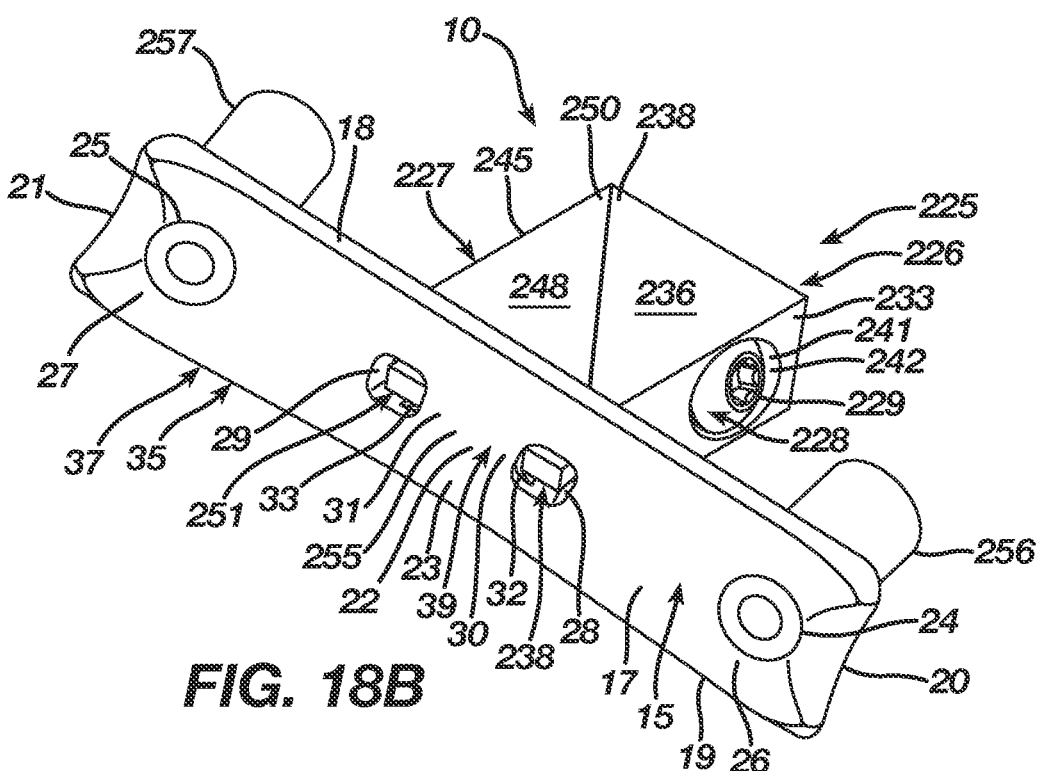
FIG. 18B is a bottom isometric view illustrating the implant retainer according to the sixth embodiment and the orthopedic implant according to the first embodiment in the insertion shape forming the orthopedic fixation system.
Figure 18C:
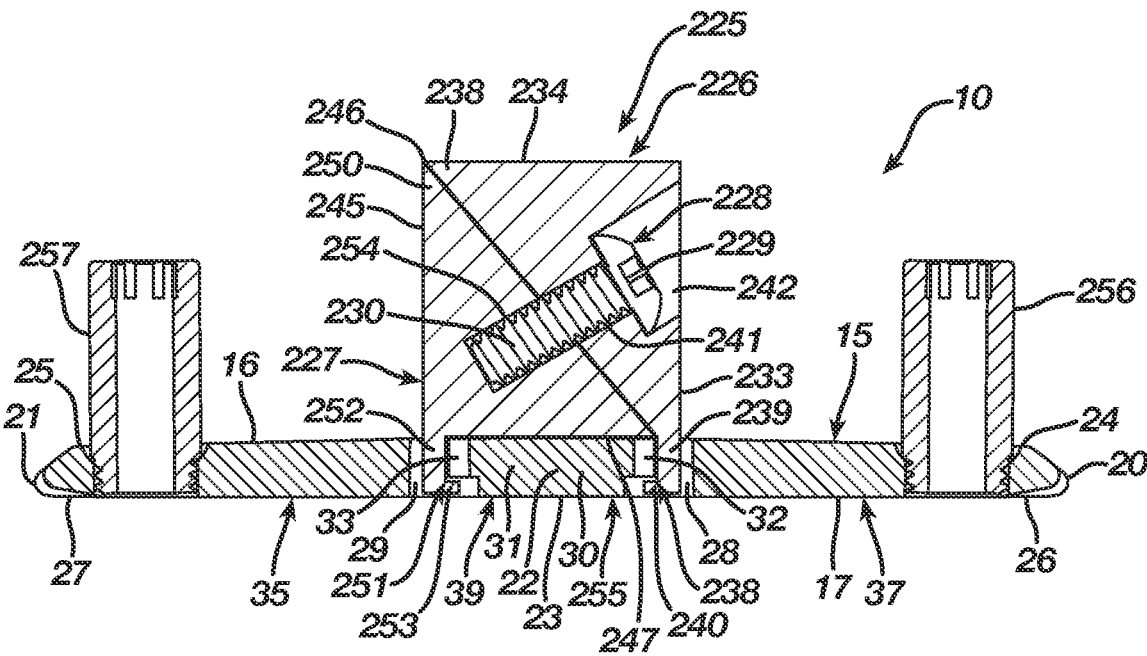
FIG. 18C is a cross-sectional view taken along line C-C of FIG. 18A illustrating the implant retainer according to the sixth embodiment and the orthopedic implant according to the first embodiment in the insertion shape forming the orthopedic fixation system.

FIGS. 18A-18B illustrate the orthopedic fixation system 10 including the implant retainer 225 according to the sixth embodiment and the orthopedic implant 11 according to the alternative of the first embodiment. The first retention block 226 and the second retention block 227 according to the sixth embodiment are designed with respect to size, shape, and a distance 255 between the fastener 238 of the first retention block 226 and the fastener 251 of the second retention block 227 whereby, when the first retention block 226 is coupled with the second retention block 227 using the set screw 228, the distance 255 substantially, completely equals the second distance 39 between the first aperture 28 and the second aperture 29 of the implant 11 when the implant 11 resides in the insertion shape 13. The distance 255 substantially, completely equals the second distance 39 in order for the fasteners 238 and 251 to fit in one of the first and second apertures 28 and 29 while concurrently abutting the respective catches 32 and 33 thereof at the respective detents 240 and 253. Moreover, the angles 238 and 250 in the sixth embodiment are complementary angles such that the first retention block 226 and the second retention block 227 are complementary at the block interfaces 232 and 244 thereof. Upon placement of the first retention block 226 in abutting relationship with the second retention block 227 at the block interfaces 232 and 244 thereof including an alignment of the block interfaces 232 and 244 and thus the bores 241 and 254, an insertion of the set screw 228 into the bores 241 and 254 secures the first and second retention blocks 226 and 227 whereby the implant retainer 225 constrains the implant 11 in the insertion shape 13 and prevents the implant 11 from returning to the natural shape 12. While the block interfaces 232 and 244 may be vertical, the block interfaces 232 and 244 in the sixth embodiment are oblique to prevent a binding thereof as the first retention block 226 slides into place in abutting relationship with the second retention block 227.

Forming the orthopedic fixation system 10 includes mechanically deforming the implant 11 from the natural shape 12 to the insertion shape 13. More particularly, the implant 11 via the transition section 22 mechanically deforms to store energy while also moving the bridge 15 from the natural form 34 where the first and second ends 20 and 21 reside at the first distance 36 and the first and second apertures 28 and 29 reside at the first distance 38 to the insertion form 35 where the first and second ends 20 and 21 reside at the second distance 37 and the first and second apertures 28 and 29 reside at the second distance 39. Mechanical deformation of the implant 11 may include cooling of the implant 11 whereby the implant 11 transitions from its austenite phase to its martensite phase in order to facilitate an easier mechanical deformation of the implant 11 from the natural shape 12 to the insertion shape 13 prior to an engagement of the implant retainer 120 with the implant 11.

After mechanical deformation of the implant 11 from the natural shape 12 to the insertion shape 13, the second retention block 227 is oriented relative to the implant 11 with the block interface 244 facing the transition section 22 and the fastener 251 aligned with the second aperture 29 in a bypass position where the fastener 251 upon insertion into the second aperture 29 will bypass the catch 33 thereof. The second retention block 227 then is placed on the implant 11 until the bottom 247 seats atop the upper surface 16 of the implant 11, resulting in the fastener 251 inserting into the second aperture 29 and bypassing the catch 33 such that the fastener 251 and thus the detent 253 thereof reside below the catch 33 while being spaced apart therefrom. Similarly, the first retention block 226 is oriented relative to the implant 11 with the block interface 232 facing the transition section 22 and the fastener 238 aligned with the first aperture 28 in a bypass position where the fastener 238 upon insertion into the first aperture 28 will bypass the catch 32 thereof. The first retention block 226 then is placed on the implant 11 until the bottom 235 seats atop the upper surface 16 of the implant 11, resulting in the fastener 238 inserting into the first aperture 28 and bypassing the catch 32 such that the fastener 238 and thus the detent 240 thereof reside below the catch 32 while being spaced apart therefrom. The insertion of the fasteners 238 and 251 in the bypass position respectively into the first and second apertures 28 and 29 locates the first retention block 226 separated from the second retention block 227 at the block interfaces 232 and 244 thereof.

Once the first and second retention blocks 226 and 227 are seated atop the implant 11, the first retention block 226 and the second retention block 227 are pushed together until the first retention block 226 at the block interface 232 abuts the second retention block 227 at the block interface 244 and further the block interface 232 and the bore 241 of the first retention block 226 align with the block interface 244 and the bore 254 of the second retention block 227. The pushing together of the first and second retention blocks 226 and 227 at the block interfaces 232 and 244 moves the fasteners 238 and 251 into an interlock position whereby the fasteners 238 and 251, which now reside at the distance 255, respectively abut the catches 32 and 33 at the detents 240 and 253 thereof. The set screw 228 inserts into the bores 241 and 254 whereupon the shaft 230 extends through the bore 241 and into the bore 254 and the head 229 resides in the countersink 242 below the rear 237 of the first retention block 226. The set screw 228 therefore connects the first retention block 226 and the second retention block 227 such that the first retention block 226 and the second retention blocks 227 span the transition section 22 of the implant 11 while also respectively engaging the catches 32 and 33 with the fasteners 238 and 251 thereof. In accordance therewith, the implant retainer 225, on account of the connected first and second retention blocks 226 and 227 concurrently spanning the transition section 22 and respectively holding the implant 11 at the catches 32 and 33 with the fasteners 238 and 254 thereof, constrains the implant 11 in the insertion shape 13 thereby preventing the implant 11 from returning to the natural shape 12. After constraining the implant 11 in the insertion shape 13, drill guides 256 and 257 may be secured respectively with the implant 11 using the first and second openings 24 and 25 thereof in order to assist in the drilling of holes into bone, bones, or bone pieces. One of ordinary skill in the art will recognize the first retention block 226 and the second retention block 227 may be reversed whereby the first retention block 226 engages the implant 11 at the catch 33 and the second retention block 227 engages the implant 11 at the catch 32.

In accordance with the orthopedic fixation system 10, the implant retainer 225, when engaged with the implant 11 as previously described, retains the implant 11 in the insertion shape 13 such that the implant 11 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the implant retainer 225 if appropriate then places the implant 11 across the first bone and the second bone with the transition section 22 of the bridge 15 located at the fixation zone. Upon placement of the implant 11 with the first opening 24 thereof at the first bone and the second opening 25 thereof at the second bone, the surgeon forms a drill hole in the first bone at the first opening 24 and a drill hole in the second bone at the second opening 25. The surgeon, if the drill guides 256 and 257 were used, removes the drill guides 256 and 257 from the first and second openings 24 and 25 of the implant 11. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 11 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 11 at the anchoring segment 27 with the second bone.

In light of the affixation of the implant 11 with the first and second bones across the fixation zone, the surgeon removes the implant retainer 225 from the implant 11. More particularly, the surgeon removes the set screw 228 from the bores 241 and 254 of the first and second retention blocks 226 and 227 thereby disconnecting the first retention block 226 from the second retention block 227. Upon disconnection, the surgeon separates the first and second retention blocks 226 and 227, resulting in the fasteners 238 and 251, respectively, at the detents 240 and 253 thereof moving out of abutting relationship with the catches 32 and 33. The surgeon removes the first retention block 226 from atop the implant 11 and thus the fastener 238 from within the first aperture 28. Likewise, the surgeon removes the second retention block 227 from atop the implant 11 and thus the fastener 253 from within the second aperture 29. Upon the removal of the implant retainer 225 from the implant 11, the implant 11 attempts transition from the insertion shape 13 to the natural shape 12 whereby the implant 11 delivers the energy stored in the transition section 22 to the first bone and the second bone, resulting in the implant 11 affixing the first bone and the second bone through an application of a compressive force to the fixation zone. The implant retainer 225 accordingly improves insertion of the implant 11 because the implant retainer 225 does not release its constraint of the implant 11 until the implant 11 is affixed to the first and second bones with its transition section 22 located across the fixation zone thereof such that the implant retainer 225 prevents the implant 11 from prematurely delivering the energy stored therein to the first and second bones at the fixation zone thereof.

The implant retainer 225 according to the sixth embodiment may be utilized with the orthopedic implant 80 according to the alternative of the fourth embodiment to form the orthopedic fixation system 10. The implant 80 includes the bridge 15 and the first and second apertures 28 and 29 and the catches 32 and 33 thereof substantially, completely identical to the implant 11 according to the alternative of the first embodiment. In accordance therewith, the implant retainer 225 engages with and disengages from the implant 80 as previously set forth with respect to the implant 11 according to the alternative of the first embodiment. When securing the implant 80 with bone, bones, or bone pieces, and, in particular, with a first bone and a second bone, the drill holes formed in the first and second bones respectively receive therein the first and second legs 87 and 88 of the implant 80 located in the insertion position 92 prior to the implant retainer 225 releasing the implant 80 for attempted transition from the insertion shape 82 to the natural shape 81 whereby the implant 80 delivers the energy stored in the transition section 22 to the first bone and the second bone, resulting in the implant 80 affixing the first bone and the second bone through an application of a compressive force thereto. The inclusion of the first and second apertures 28 and 29 and the catches 32 and 33 thereof in the implant 80 improves implantation of the implant 80 because the engagement of the implant retainer 225 with the implant 80 at the first and second apertures 28 and 29 and the catches 32 and 33 thereof permits implanting of the implant 80 in the insertion position 82 into bone, bones, or bone pieces using the implant retainer 225 without having to tamp the implant 80 after removal of the implant retainer 225.

Figure 19A:
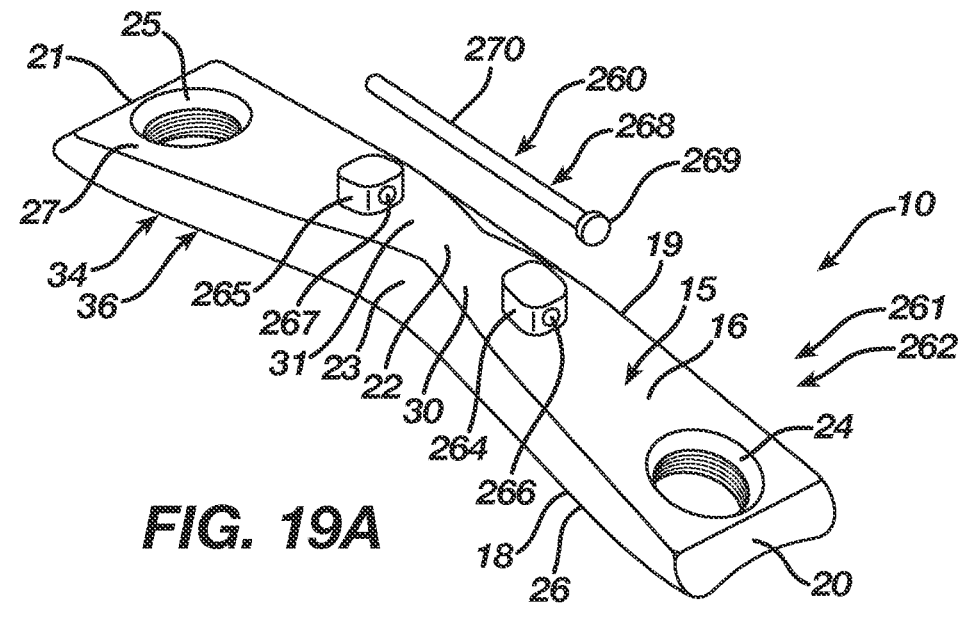
FIG. 19A is a top isometric view illustrating an implant retainer according to a seventh embodiment and an orthopedic implant according to a fifth embodiment in a natural shape.
Figure 19B:
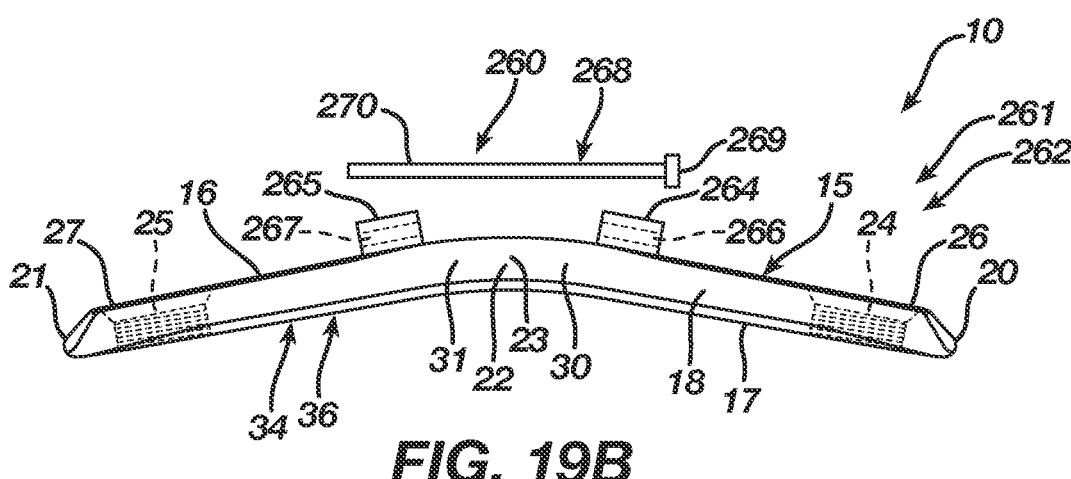
FIG. 19B is a side view illustrating the implant retainer according to the seventh embodiment and the orthopedic implant according to the fifth embodiment in the natural shape.
Figure 19C:
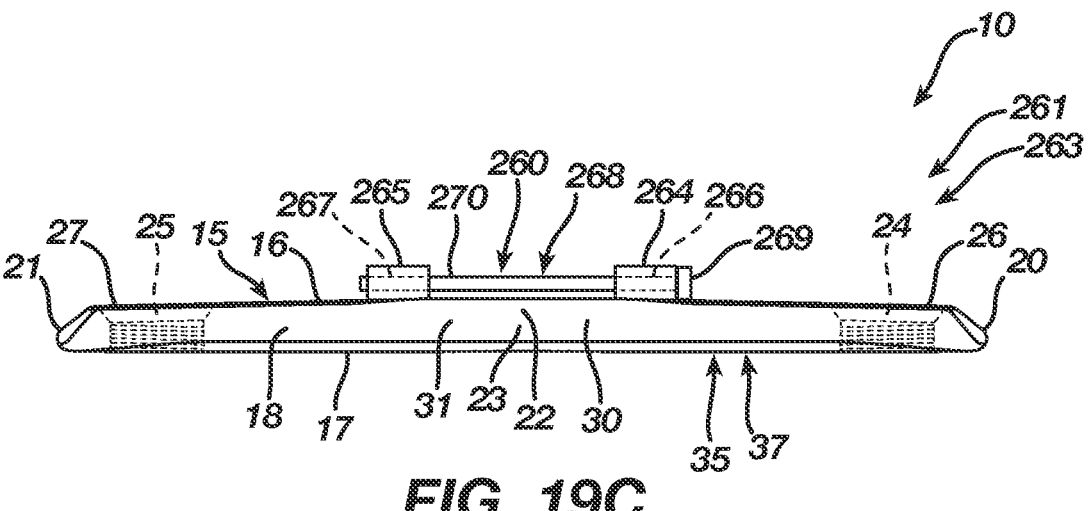
FIG. 19C is side view illustrating the implant retainer according to the seventh embodiment and the orthopedic implant according to the fifth embodiment in the insertion shape forming the orthopedic fixation system.

FIGS. 19A-19D illustrate an implant retainer 260 according to a seventh embodiment and an orthopedic implant 261 according to a fifth embodiment utilized in forming the orthopedic fixation system 10. The orthopedic implant 261 according to the fifth embodiment includes a natural shape 262 as illustrated FIGS. 19A-19B and an insertion shape 263 as illustrated in FIG. 19C. The implant 261 is substantially similar in design and operation relative to the implant 11 according to the first embodiment such that, for the sake of brevity, only differences therebetween will be described herein. Moreover, one of ordinary skill in the art will recognize that like parts of the implant 261 labeled with like numerals of the implant 11 incorporate a design and function as previously set forth in the detailed description of the implant 11 according to the first embodiment. While the implant 11 includes the first and second apertures 28 and 29 and the catches 32 and 33 thereof in order to facilitate a securing of the implant 11 with an implant retainer, the implant 261 eliminates the first and second apertures 28 and 29 and the catches 32 and 33 in favor of securing features in the form of first and second posts 264 and 265 configured to engage with the implant retainer 260. The first post 264 protrudes from the upper surface 16 of the bridge 15 adjacent the transition section 22 at the first side 30 thereof. The first post 264 includes an opening 266 therethrough that traverses the first post 264 such that the axis of the opening 266 lies transverse relative to the transition section 22. The second post 265 protrudes from the upper surface 16 of the bridge 15 adjacent the transition section 22 at the second side 31 thereof. The second post 265 includes an opening 267 therethrough that traverses the second post 265 such that the axis of the opening 267 lies transverse relative to the transition section 22. The first post 264 and the second post 265 are positioned atop the bridge 15 such that, when the implant 261 resides in the insertion shape 263, the openings 266 and 267 align at the axes thereof across the transition section 22. The first post 264 and the second post 265 accordingly provide points of engagement for the implant 261 with the implant retainer 260. While the first and second posts 264 and 265 protrude from the upper surface 16 of the bridge 15, the first and second posts 264 and 265 may protrude from either the first side 18 or the second side 19 of the bridge 15.

The implant retainer 260 in the seventh embodiment is a fastener in the form of a pin 268 including a head 269 and a shaft 270 extending therefrom. The shaft 270 secures frictionally with the first and second posts 264 and 265 at the openings 266 and 267 or alternatively may include threads for a screw fit with corresponding threads at the openings 266 and 267 of the first and second posts 264 and 265. The pin 268 in the seventh embodiment is designed with respect to size, shape, and length whereby, when the implant 261 resides in the insertion shape 263, the pin 268 inserts into the openings 266 and 267 while spanning the first and second posts 264 and 265. While the fastener in the form of a pin 268 is illustrated as cylindrical, the pin 268 may be any suitable cross-sectional shape, such as, for example, triangular, quadrilateral, and the like. The pin 268 at the shaft 270 may protrude from either the first post 264 or the second post 265 such that a cap or nut may be employed to secure the pin 268 with the first and second posts 264 and 265. Although the pin 268 includes the head 269, the pin 268 may include only the shaft 270 whereby the shaft 270 inserts into the openings 266 and 267 while spanning the first and second posts 264 and 265.

The first and second posts 264 and 265 may be formed integrally with the bridge 15, or preferably the first and second posts 264 and 265 may be removable from the bridge 15 in order to reduce the profile of the implant 261 after affixation of the implant 261 with bone, bones, or bone pieces. Removability of the first and second posts 264 and 265 from the bridge 15 includes the first and second posts 264 and 265 each having a shaft extending from a bottom thereof and a corresponding opening in the bridge 15 at the upper surface thereof. The shafts of the first and second posts 264 and 265 insert into a corresponding opening in the bridge 15 and are maintained therein via a friction fit. Alternatively, the shafts of the first and second posts 264 and 265 may include external threads while the corresponding openings in the bridge 15 include internal threads for a threaded fastening of the first and second posts 264 and 265 with the bridge 15.

Although the opening 266 in the first post 264 and the opening 267 in the second post 265 preferably are bores, one or both of the first and second posts 264 and 265 may include a slot substituted for the bores. Illustratively, the opening 266 of the first post 264 includes a bore, whereas the opening 267 of the second post 265 includes a slot open at the side of the second post 265 facing the first side 18 of the bridge 15. The inclusion of the slot in the second post 265 permits a removal of the pin 268 from the slot through a rotation of the first post 264 when the first and second posts 264 and 265 are removable from the bridge 15. When both the openings 266 and 267 of the first and second posts 264 and 265 include a slot substituted for the bores, the slots may be on the same sides of the first and second posts 264 and 265 or alternatively on opposite sides of the first and second posts 264 and 265.

Forming the orthopedic fixation system 10 when the first and second posts 264 and 265 are removable includes inserting the shafts of the first and second posts 264 and 265 respectively into the corresponding opening in the bridge 15 whereby the openings 266 and 267 of the first and second posts 264 and 265 align across the transition section 22. Regardless of whether the first and second posts 264 and 265 are removable, forming the orthopedic fixation system 10 includes mechanically deforming the implant 261 from the natural shape 262 to the insertion shape 263. More particularly, the implant 261 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Moreover, the movement of the bridge 15 aligns the first post 264 with the second post 265 such that the opening 266 and the opening 267 align at the axes thereof across the transition section 22. Mechanical deformation of the implant 261 may include cooling of the implant 261 whereby the implant 261 transitions from its austenite phase to its martensite phase in order to facilitate an easier mechanical deformation of the implant 261 from the natural shape 262 to the insertion shape 263 prior to an engagement of the implant retainer 260 with the implant 261.

After mechanical deformation of the implant 261 from the natural shape 262 to the insertion shape 263, the pin 268 at the shaft 270 inserts into and through the opening 266 of the first post 264, traverses the transition section 22, and then inserts into and through the opening 267 of the second post 265 until the head 269 thereof abuts the first post 264. One of ordinary skill in the art will recognize the pin 268 at the shaft 270 may insert first into and through the opening 267 of the second post 265. The pin 268 therefore interconnects the first post 264 and the second post 265 such that the pin 268 spans the transition section 22 of the implant 261. In accordance therewith, the implant retainer 260, on account of the pin 268 interconnecting the first and second posts 264 and 265 while spanning the transition section 22, constrains the implant 261 in the insertion shape 263 thereby preventing the implant 261 from returning to the natural shape 262. After constraining the implant 261 in the insertion shape 263, drill guides may be secured respectively with the implant 261 using the first and second openings 24 and 25 thereof in order to assist in the drilling of holes into bone, bones, or bone pieces.

In accordance with the orthopedic fixation system 10, the implant retainer 260, when engaged with the implant 261 as previously described, retains the implant 261 in the insertion shape 263 such that the implant 261 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the implant retainer 260 if appropriate then places the implant 261 across the first bone and the second bone with the transition section 22 of the bridge 15 located at the fixation zone. Upon placement of the implant 261 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 261. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 261 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 261 at the anchoring segment 27 with the second bone.

In light of the affixation of the implant 261 with the first and second bones across the fixation zone, the surgeon removes the implant retainer 260 from the implant 261. More particularly, the surgeon pulls upon the pin 268 at the head 269 resulting in the shaft 270 exiting the opening 267 of the second post 265, traversing the transition section 22, and then exiting the opening 266 of the first post 264. In the alternative, when the opening 266 in a removable first post 264 includes a bore and the opening 267 in a removable second post 265 includes a slot, a rotation of the first post 264 pivots the pin 268 at the shaft 270 from the slot of the removable second post 265 such that a pulling upon the pin 268 at the head 269 removes the pin 268 from the bore of the removable first post 264. Further in the alternative, the surgeon between the first and second posts 264 and 265 cuts the shaft 270 of the pin 268 thereby allowing a pulling of the cut shaft 270 of the pin 268 from the first post 264 using the head 269 and a pulling of the cut shaft 270 of the pin 268 from the second post 265. When cutting is employed in release of the implant 261, a cable secured between the first and second posts 264 and 265 may be used in place of the pin 268. Upon the removal of the implant retainer 260 from one of the first post 264 or the second post 265 and ultimately the implant 261, the implant 261 attempts transition from the insertion shape 263 to the natural shape 262 whereby the implant 261 delivers the energy stored in the transition section 22 to the first bone and the second bone, resulting in the implant 261 affixing the first bone and the second bone through an application of a compressive force to the fixation zone. When the first and second posts 264 and 265 are removable from the bridge 15, the shafts of the first and second posts 264 and 265 respectively are pulled or unthreaded from the corresponding openings in the bridge 15 in order to reduce the profile of the implant 261 after affixation of the implant 261 with the first and second bones across the fixation zone. The implant retainer 260 accordingly improves insertion of the implant 261 because the implant retainer 260 does not release its constraint of the implant 261 until the implant 261 is affixed to the first and second bones with its transition section 22 located across the fixation zone thereof such that the implant retainer 260 prevents the implant 261 from prematurely delivering the energy stored therein to the first and second bones at the fixation zone thereof.

FIGS. 20A-20D illustrate the implant retainer 260 according to the seventh embodiment and an orthopedic implant 275 according to a sixth embodiment utilized in forming the orthopedic fixation system 10. The orthopedic implant 275 according to the sixth embodiment includes a natural shape 276 as illustrated FIGS. 20A-20B and an insertion shape 277 as illustrated in FIG. 20C. The implant 275 is substantially similar in design and operation relative to the orthopedic implant 80 according to the fourth embodiment such that, for the sake of brevity, only differences therebetween will be described herein. Moreover, one of ordinary skill in the art will recognize that like parts of the implant 275 labeled with like numerals of the implant 80 incorporate a design and function as previously set forth in the detailed description of the implant 80 according to the fourth embodiment. While the implant 80 includes the first and second apertures 28 and 29 and the catches 32 and 33 thereof in order to facilitate a securing of the implant 80 with an implant retainer, the implant 275 eliminates the first and second apertures 28 and 29 and the catches 32 and 33 in favor of the first and second posts 264 and 265 and the respective openings 266 and 267 thereof as previously set forth with respect to the implant 261 according to the fifth embodiment. In accordance therewith, the implant retainer 260 engages with and disengages from the implant 275 as previously set forth with respect to the implant 261 according to the fifth embodiment. When securing the implant 275 with bone, bones, or bone pieces, and, in particular, with a first bone and a second bone, the drill holes formed in the first and second bones respectively receive therein the first and second legs 87 and 88 of the implant 275 located in the insertion position 92 prior to the implant retainer 260 releasing the implant 275 for attempted transition from the insertion shape 277 to the natural shape 276 whereby the implant 275 delivers the energy stored in the transition section 22 to the first bone and the second bone, resulting in the implant 275 affixing the first bone and the second bone through an application of a compressive force thereto. The inclusion of the first and second posts 264 and 265 in the implant 275 improves implantation of the implant 275 because the engagement of the implant retainer 260 with the implant 275 at the first and second posts 264 and 265 permits implanting of the implant 275 in the insertion position 277 into bone, bones, or bone pieces using the implant retainer 260 without having to tamp the implant 275 after removal of the implant retainer 260.

Figure 21A:
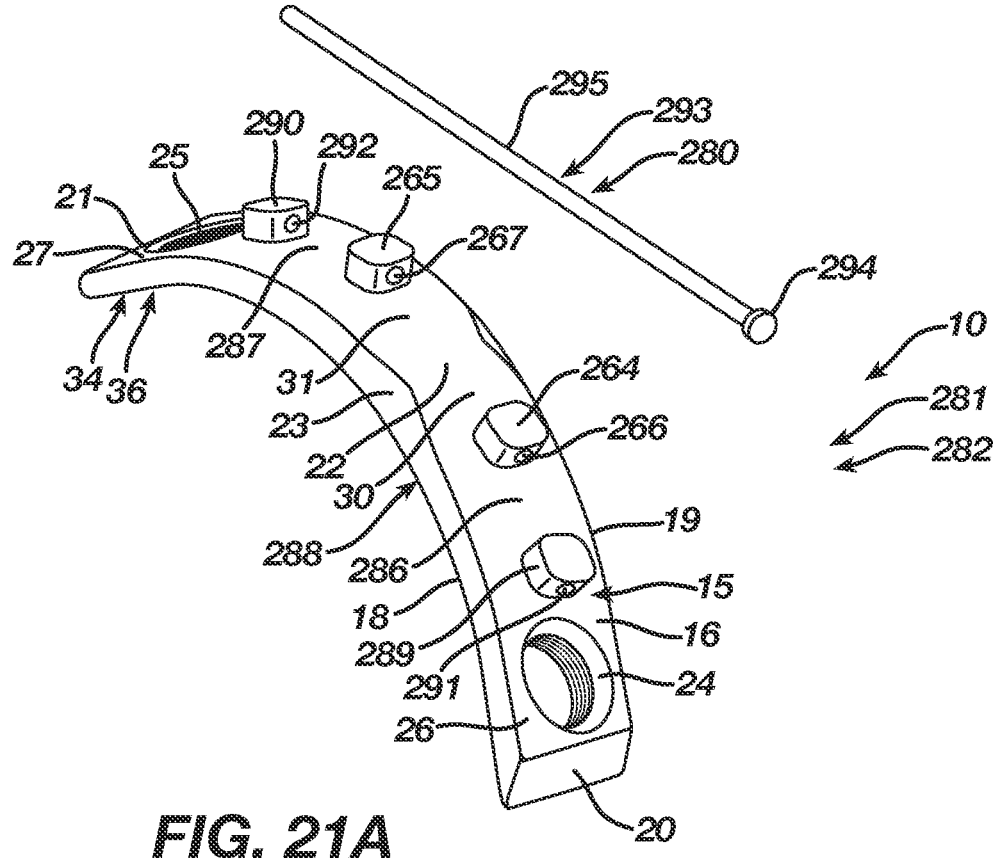
FIG. 21A is a top isometric view illustrating an implant retainer according to an alternative of the seventh embodiment and an orthopedic implant according to an alternative of the fifth embodiment in a natural shape.
Figures 21B, 21C, 21D, 21E:
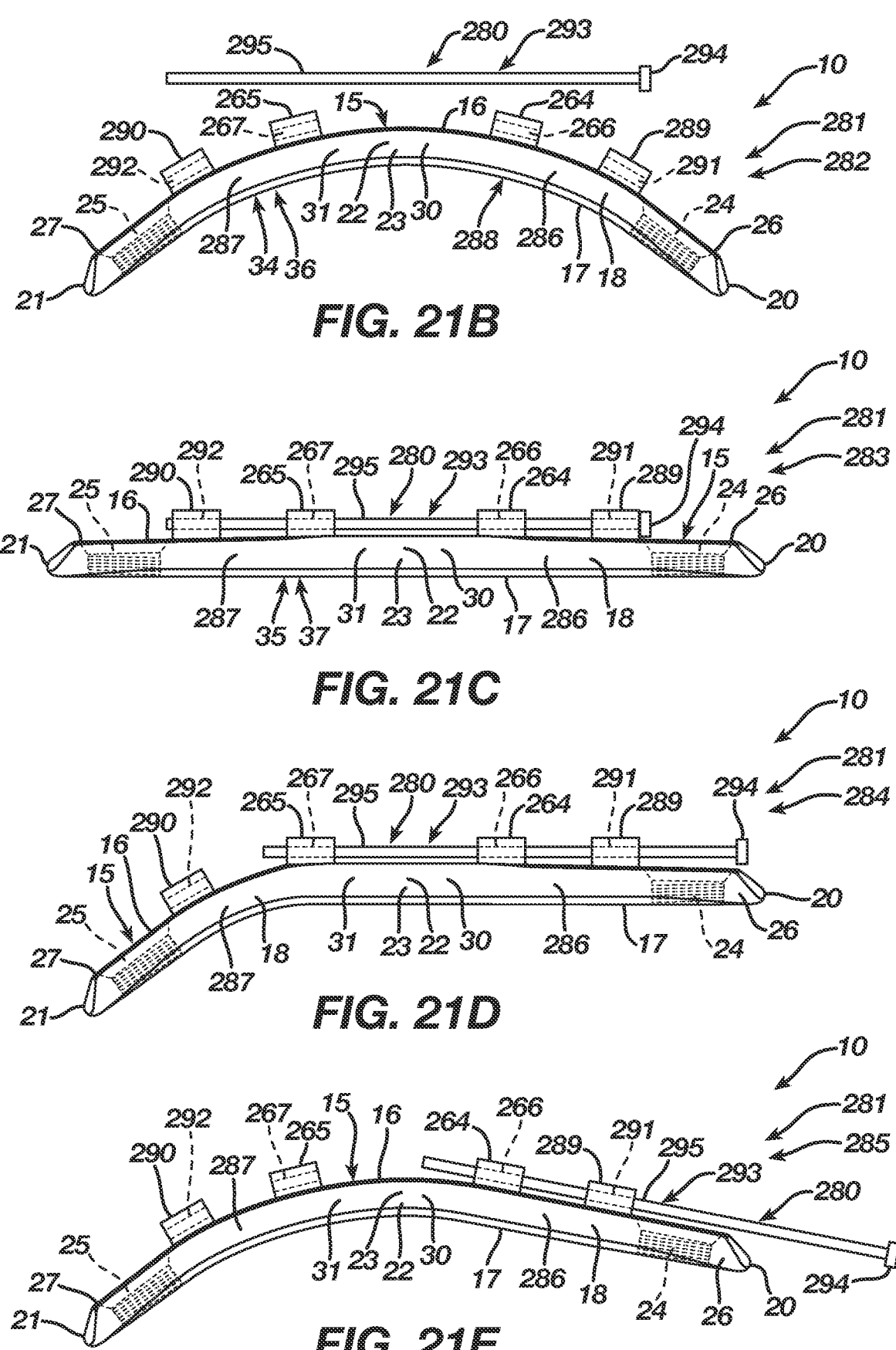
FIG. 21B is a side view illustrating the implant retainer according to the alternative of the seventh embodiment and the orthopedic implant according to the alternative of the fifth embodiment in the natural shape.
FIG. 21C is side view illustrating the implant retainer according to the alternative of the seventh embodiment and the orthopedic implant according to the alternative of the fifth embodiment in the insertion shape forming the orthopedic fixation system.
FIGS. 21D-21E are side views illustrating the orthopedic fixation system and a removal of the implant retainer according to the alternative of the seventh embodiment from engagement with the orthopedic implant according to the alternative of the fifth embodiment.

FIGS. 21A-21E illustrate an implant retainer 280 according to an alternative of the seventh embodiment and an orthopedic implant 281 according to an alternative of the fifth embodiment utilized in forming the orthopedic fixation system 10. The orthopedic implant 281 according to the alternative of the fifth embodiment includes a natural shape 282 as illustrated in FIGS. 21A-21B and an insertion shape 283 as illustrated in FIG. 21C. The orthopedic implant 281 according to the alternative of the fifth embodiment when used in combination with the implant retainer 280 further includes but is not limited to a first intermediate shape 284 as illustrated in FIG. 21D and a second intermediate shape 285 as illustrated in FIG. 21E. The implant 281 is substantially similar in design and operation relative to the implant 261 according to the fifth embodiment and the implant 11 according to the first embodiment such that, for the sake of brevity, only differences therebetween will be described herein. Moreover, one of ordinary skill in the art will recognize that like parts of the implant 281 labeled with like numerals of the implant 261 and the implant 11 incorporate a design and function as previously set forth in the detailed description of the implant 261 according to the fifth embodiment and the implant 11 according to the first embodiment. While the implant 281 and the implant 11 include the transition section 22 at the center section 23, the implant 281 comprises multiple transition sections including but not limited to the transition section 22 at the center section 23, a transition section 286 between the center section 23 and the anchoring segment 26, and a transition section 287 between the center section 23 and the anchoring segment 27 that produce a continuous curve 288 in the implant 281 when the implant 281 resides in the natural shape 282. Although the implant 11 includes the first and second apertures 28 and 29 and the catches 32 and 33 thereof in order to facilitate a securing of the implant 11 with an implant retainer, the implant 281 identical to the implant 261 eliminates the first and second apertures 28 and 29 and the catches 32 and 33 in favor of the first and second posts 264 and 265 and the respective openings 266 and 267 thereof as previously set forth with respect to the implant 261 according to the fifth embodiment. The first post 264 protrudes from the upper surface 16 of the bridge 15 between the transition section 22 at the first side 30 thereof and the transition section 286, whereas the second post 265 protrudes from the upper surface 16 of the bridge 15 between the transition section 22 at the second side 31 thereof and the transition section 287. The implant 281 further includes securing features in the form of third and fourth posts 289 and 290 configured along with the first and second posts 264 and 265 to engage with the implant retainer 280. The third post 289 protrudes from the upper surface 16 of the bridge 15 between the transition section 286 and the anchoring segment 26. The third post 289 includes an opening 291 therethrough that traverses the third post 289 such that the axis of the opening 291 lies transverse relative to the transition sections 22 and 286. The fourth post 290 protrudes from the upper surface 16 of the bridge 15 between the transition section 287 and the anchoring segment 27. The fourth post 290 includes an opening 292 therethrough that traverses the second post 265 such that the axis of the opening 292 lies transverse relative to the transition sections 22 and 287. The first post 264, the second post 265, the third post 289, and the fourth post 290 are positioned atop the bridge 15 such that, when the implant 281 resides in the insertion shape 283, the openings 266, 267, 291, and 292 align at the axes thereof across the transition sections 22, 286, and 287. The first post 264, the second post 265, the third post 289, and the fourth post 290 accordingly provide points of engagement for the implant 281 with the implant retainer 280. Similar to the first and second posts 254 and 265 of the implant 261 according to the fifth embodiment, the first post 264, the second post 265, the third post 289, and the fourth post 290 may be formed integrally with the bridge 15, or preferably the first post 264, the second post 265, the third post 289, and the fourth post 290 may be removable from the bridge 15 in order to reduce the profile of the implant 281 after affixation of the implant 281 with bone, bones, or bone pieces. The respective openings 266, 267, 291, and 292 of the first post 264, the second post 265, the third post 289, and the fourth post 290, similar to the first and second posts 264 and 265 of the implant 261 according to the fifth embodiment, preferably include bores but may include a slot substituted for the bores. While the first, second, third, and fourth posts 264, 265, 289, and 290 protrude from the upper surface 16 of the bridge 15, the first, second, third, and fourth posts 264, 265, 289, and 290 may protrude from either the first side 18 or the second side 19 of the bridge 15.

The implant retainer 280 in the alternative of the seventh embodiment is a fastener in the form of a pin 293 including a head 294 and a shaft 295 extending therefrom. The shaft 295 secures frictionally with the first, second, third, and fourth posts 264, 265, 289 and 290 at the openings 266, 267, 291, and 292 or alternatively may include threads for a screw fit with corresponding threads at the openings 266, 267, 291, and 292 of the first, second, third, and fourth posts 264, 265, 289 and 290. The pin 293 in the alternative of the seventh embodiment is designed with respect to size, shape, and length whereby, when the implant 281 resides in the insertion shape 283, the pin 293 inserts into the openings 266, 267, 291, and 292 while spanning the first, second, third, and fourth posts 264, 265, 289 and 290. The pin 293 at the shaft 295 may protrude from either the third post 289 or the fourth post 290 such that a cap or nut may be employed to secure the pin 293 with the first, second, third, and fourth posts 264, 265, 289 and 290.

Forming the orthopedic fixation system 10 when the first, second, third, and fourth posts 264, 265, 289, and 290 are removable includes inserting shafts of the first, second, third, and fourth posts 264, 265, 289, and 290 respectively into corresponding openings in the bridge 15 whereby the openings 266, 267, 291, and 292 align across the transition sections 22, 286, and 287. Regardless of whether the first, second, third, and fourth posts 264, 265, 289, and 290 are removable, forming the orthopedic fixation system 10 includes mechanically deforming the implant 281 from the natural shape 282 to the insertion shape 283. More particularly, the implant 281 via the transition sections 22, 286, and 287 mechanically deforms to store energy while also moving the bridge 15 from the natural form 34 where the first and second ends 20 and 21 reside at the first distance 36 to the insertion form 35 where the first and second ends 20 and 21 reside at the second distance 37. Moreover, the movement of the bridge 15 aligns the first post 264 with the third post 289 such that the opening 266 and the opening 291 align at the axes thereof across the transition section 286, the first post 264 with the second post 265 such that the opening 266 and the opening 267 align at the axes thereof across the transition section 22, and the second post 265 with the fourth post 290 such that the opening 267 and the opening 292 align at the axes thereof across the transition section 287. Mechanical deformation of the implant 281 may include cooling of the implant 281 whereby the implant 281 transitions from its austenite phase to its martensite phase in order to facilitate an easier mechanical deformation of the implant 281 from the natural shape 282 to the insertion shape 283 prior to an engagement of the implant retainer 280 with the implant 281.

After mechanical deformation of the implant 281 from the natural shape 282 to the insertion shape 283, the pin 293 at the shaft 295 inserts into and through the opening 291 of the third post 289, traverses the transition section 286, and then inserts into and through the opening 266 of the first post 264. The pin 293 at the shaft 295 further traverses the transition section 22 and then inserts into and through the opening 267 of the second post 265. The pin 293 at the shaft 295 still further traverses the transition section 287 and then inserts into and through the opening 292 of the fourth post 265 until the head 294 thereof abuts the third post 289. One of ordinary skill in the art will recognize the pin 293 at the shaft 295 may insert first into and through the opening 292 of the fourth post 290. The pin 293 therefore interconnects the first, second, third, and fourth posts 264, 265, 289 and 290 such that the pin 293 spans the transition sections 22, 286, and 287 of the implant 281. In accordance therewith, the implant retainer 280, on account of the pin 293 interconnecting the first, second, third, and fourth posts 264, 265, 289 and 290 while spanning the transition sections 22, 286, and 287, constrains the implant 281 in the insertion shape 283 thereby preventing the implant 281 from returning to the natural shape 282. After constraining the implant 281 in the insertion shape 283, drill guides may be secured respectively with the implant 281 using the first and second openings 24 and 25 thereof in order to assist in the drilling of holes into bone, bones, or bone pieces.

In accordance with the orthopedic fixation system 10, the implant retainer 280, when engaged with the implant 281 as previously described, retains the implant 281 in the insertion shape 283 such that the implant 281 is ready for securing with bone, bones, or bone pieces, and, in particular, with a first bone and a second bone, which are presented herein as an example. A surgeon aligns the first bone with the second bone at fixation zones in an orientation that promotes fixation of the first bone with the second bone and a proper healing thereof. The surgeon using the implant retainer 280 if appropriate then places the implant 281 across the first bone and the second bone with the transition sections 22, 286, and 287 of the bridge 15 located at the fixation zones. Upon placement of the implant 281 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 281. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 281 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 281 at the anchoring segment 27 with the second bone.

In light of the affixation of the implant 281 with the first and second bones across the fixation zones, the surgeon removes the implant retainer 280 from the implant 281. More particularly, the surgeon pulls upon the pin 293 at the head 294 resulting in the shaft 295 exiting the opening 292 of the fourth post 290 and traversing the transition section 287 as illustrated in FIG. 21D. Upon the removal of the implant retainer 280 from the fourth post 290, the implant 281 attempts transition from the insertion shape 283 to the first intermediate shape 284 whereby the implant 281 delivers the energy stored in the transition section 287 to the first bone and the second bone. The surgeon further pulls upon the pin 293 at the head 294 resulting in the shaft 295 exiting the opening 267 of the second post 265 and traversing the transition section 22 as illustrated in FIG. 21E. After the removal of the implant retainer 280 from the second post 290, the implant 281 attempts transition from the first intermediate shape 284 to the second intermediate shape 285 whereby the implant 281 delivers the energy stored in the transition section 22 to the first bone and the second bone. The surgeon still further pulls upon the pin 293 at the head 294 resulting in the shaft 295 exiting the opening 266 of the first post 264, traversing the transition section 286, and then exiting the opening 291 of the third post 289. Once the implant retainer 280 is removed from the first post 264, the implant 281 attempts transition from the second intermediate shape 285 to the natural shape 282 whereby the implant 281 delivers the energy stored in the transition section 286 to the first bone and the second bone, resulting in the implant 281 affixing the first bone and the second bone through an application of a compressive force to the fixation zones. When the first, second, third, and fourth posts 264, 265, 289, and 290 are removable from the bridge 15, the shafts of the first, second, third, and fourth posts 264, 265, 289, and 290 respectively are pulled or unthreaded from the corresponding openings in the bridge 15 in order to reduce the profile of the implant 281 after affixation of the implant 281 with the first and second bones across the fixation zones. It should be understood that incremental removal of the pin 293 from the first, second, third, and fourth posts 264, 265, 289 and 290 includes a cutting of the pin 293 followed by a removal of the pin 293 according to the cut pieces. When cutting is employed in release of the implant 281, a cable or cables secured between the first, second, third, and fourth posts 264, 265, 289 and 290 may be used in place of the pin 293. Moreover, while the pin 293 as previously described may be incrementally removed from the fourth post 290 and then the second post 265 or both the fourth post 290 and the second post 265 in order to vary the force the implant 281 applies to the first bone and the second bone, one or ordinary skill in the art will recognize the pin 293 may be continuously removed from the first, second, third, and fourth posts 264, 265, 289 and 290 such that the implant 281 attempts transition from the insertion shape 283 to the natural shape 282. The implant retainer 280 accordingly improves insertion of the implant 281 because the implant retainer 280 does not release its constraint of the implant 281 until the implant 281 is affixed to the first and second bones with its transition sections 22, 286, and 287 located across the fixation zones thereof such that the implant retainer 280 prevents the implant 281 from prematurely delivering the energy stored therein to the first and second bones at the fixation zones thereof.

FIGS. 22A-22B illustrate an orthopedic implant 300 according to a seventh embodiment in a natural shape 301, whereas FIGS. 22C-22D illustrates the orthopedic implant 300 in an insertion shape 302. The implant 300 is substantially similar in design and operation relative to the implant 11 according to the first embodiment such that, for the sake of brevity, only differences therebetween will be described herein. Moreover, one of ordinary skill in the art will recognize that like parts of the implant 300 labeled with like numerals of the implant 11 incorporate a design and function as previously set forth in the detailed description of the implant 11 according to the first embodiment. While the implant 11 includes the first and second apertures 28 and 29 and the catches 32 and 33 thereof in order to facilitate a securing of the implant 11 with an implant retainer, the implant 300 eliminates the first and second apertures 28 and 29 and the catches 32 and 33 in favor of securing features in the form of first and second grooves 303 and 304 configured to engage with an implant retainer. The first groove 303 is cut into the lower surface 17 of the bridge 15 along the first side 18 thereof. The first groove 303 includes a length 305 whereby the first groove 303 at a first end 306 extends beyond the first side 30 of the transition section 22 and at a second end 307 extends beyond the second side 31 of the transition section 22. Likewise, the second groove 304 is cut into the lower surface 17 of the bridge 15 along the second side 19 thereof. The second groove 304 includes a length 308, which, in the seventh embodiment, is the same as the length 305, whereby the second groove 304 at a first end 309 extends beyond the first side 30 of the transition section 22 and at a second end 310 extends beyond the second side 31 of the transition section 22. The first groove 303 and the second groove 304 are longer than the transition section 22 in order for an implant retainer to constrain the implant 300 in the insertion shape 302.

FIG. 23 illustrates an implant retainer 311 according to an eighth embodiment. The implant retainer 311 in the eighth embodiment comprises forceps 312 including a first implant grip 313 and a second implant grip 314, each of which is configured to engage an orthopedic implant. The forceps 312 include handles 315 and 316, which, in the eighth embodiment comprise ring handles, and a locking ratchet 317 extending between the handles 315 and 316 whereby the locking ratchet 317 is configured to arrest the movement of the handles 315 and 316 thereby locking the forceps 312 in engagement with the orthopedic implant 300. The forceps 312 include shanks 318 and 319 extending respectively from the handles 315 and 316 at an angle 320 that produces a convergence thereof. The shanks 318 and 319 at the convergence thereof incorporate a hinge 321 that secures the shanks 318 and 319 together and further functions as a pivot point for the forceps 312. The forceps 312 include blades 322 and 323 terminating respectively in the first implant grip 313 and the second implant grip 314. The blades 322 and 323 extend respectively from the shanks 318 and 319 along the angle 320 in a traversal of the hinge 321 such that the blade 322 locates the first implant grip 313 positionally opposite relative to the handle 315 and the blade 323 locates the second implant grip 314 positionally opposite relative to the handle 316. Actuation of the forceps 312, as will be described more fully herein, includes a manipulation of the handles 315 and 316 resulting in the first implant grip 313 and the second implant grip 314 each engaging the implant 300 followed by a locking of the forceps 312 via the locking ratchet 317. In the eighth embodiment, manipulation of the handles 315 and 316 consists of closing the handles 315 and 316 and thus the forceps 312 until the first implant grip 313 and the second implant grip 314 engage the implant 300.

The first implant grip 313 includes a plate 324 with a top 325, a bottom 326, and a front face 327. The first implant grip 313 further includes a first flange 328 extending from the plate 324 at the top 325 thereof and a second flange 329 extending from the plate 324 at the bottom 326 thereof. The first implant grip 313 secures with the blade 322 at the first flange 328 whereby the plate 324 at the front face 327, the first flange 328, and the second flange 329 face inward relative to the forceps 312. The first implant grip 313 with respect to a height 330 of the plate 324 is correspondingly sized relative to the first and second sides 18 and 19 of the bridge 15 such that an engagement of the first implant grip 313 with the implant 300 results in the front face 327 abutting either the first side 18 or the second side 19 whereby the first flange 328 extends over the upper surface 16 and the second flange 329 extends over the lower surface 17 while fitting within either the first groove 303 or the second groove 304. Moreover, the first implant grip 313 with respect to a length 331 of the plate 324 and thus the first and second flanges 328 and 329 is correspondingly sized relative to the lengths 305 and 308 of the first and second grooves 303 and 304 such that an engagement of the first implant grip 313 with the implant 300 results in the second flange 329 fitting within either the first groove 303 or the second groove 304 such that the first implant grip 313 is longer than the transition section 22 in order for the implant retainer 311 to constrain the implant 300 in the insertion shape 302.

The second implant grip 314 is substantially, completely identical in design and operation relative to the first implant grip 313 such that, for the sake of brevity, only differences therebetween will be described herein. Moreover, one of ordinary skill in the art will recognize that like parts of the second implant grip 314 labeled with like numerals of the first implant grip 313 incorporate a design and function as previously set forth in the detailed description of the first implant grip 313. During use of the implant retainer 311, the second implant grip 314 is employed substantially the same as the first implant grip 313, except the second implant grip 314, which secures with the blade 323 at the first flange 328, is reversed relative to the first implant grip 313 whereby the second implant grip 314 comprises a mirror image of the first implant grip 313. Illustratively, when the first implant grip 313 engages with the implant 300 the first side 18 thereof with the first flange 328 extending over the upper surface 16 and the second flange 329 fitting within the first groove 303, the second implant grip 314 engages with the implant 300 the second side 19 thereof with the first flange 328 extending over the upper surface 16 and the second flange 329 fitting within the second groove 304. In accordance therewith, the second implant grip 314 mirrors the first implant grip 313 whereby the forceps 312 at the first and second flanges 328 and 329 of the first and second implant grips 313 and 314 engages with the implant 300 in order to constrain the implant 300 in the insertion shape 302.

Figure 24A:
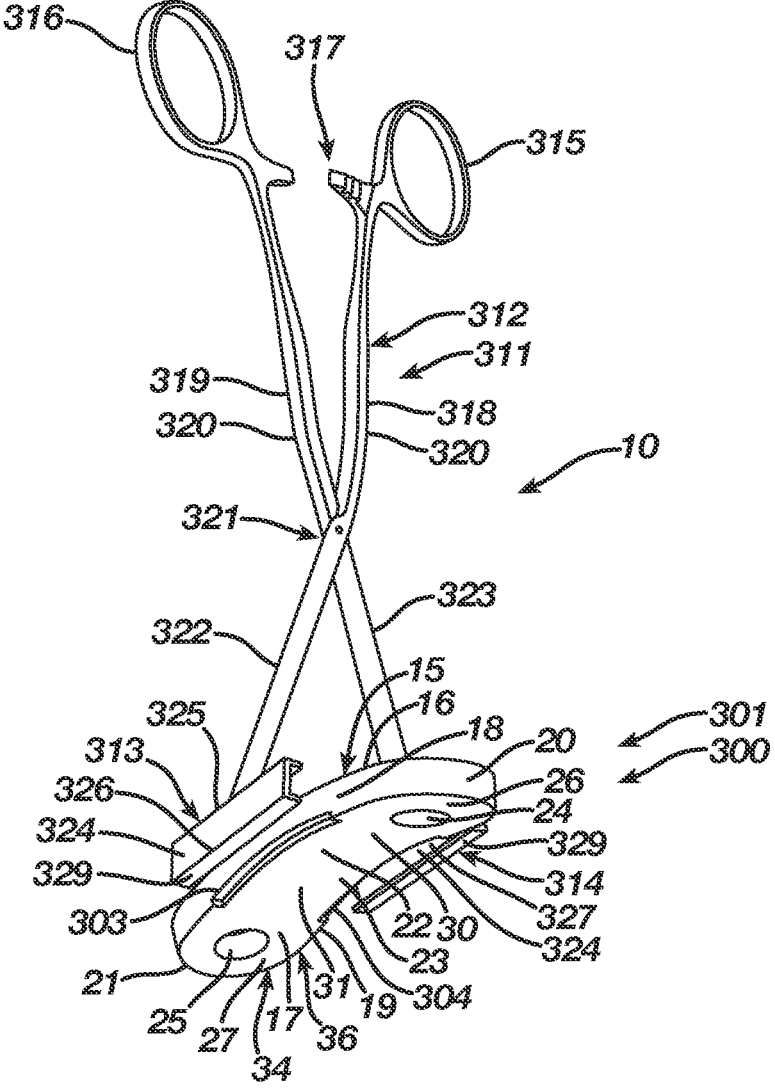
FIG. 24A is a bottom isometric view illustrating the implant retainer according to the eighth embodiment and the orthopedic implant according to the seventh embodiment in the natural shape.
Figure 24B:
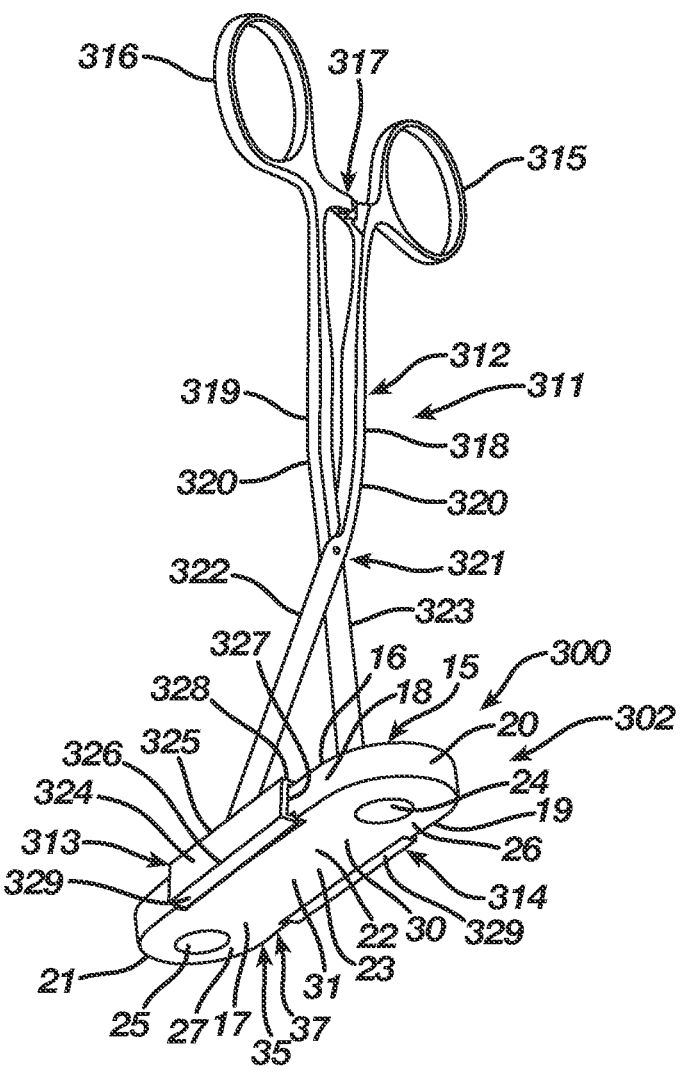
FIG. 24B is a bottom isometric view illustrating the implant retainer according to the eighth embodiment and the orthopedic implant according to the seventh embodiment in the insertion shape forming the orthopedic fixation system.

FIGS. 24A-24B illustrate the orthopedic fixation system 10 including the orthopedic implant 300 according to the seventh embodiment and the implant retainer 311 according to the eighth embodiment, which, more particularly, comprise the forceps 312. Forming the orthopedic fixation system 10 includes mechanically deforming the implant 300 from the natural shape 301 to the insertion shape 302. More particularly, the implant 300 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Moreover, the movement of the bridge 15 configures the first and second grooves 303 and 304 for receipt therein of one of the first and second implant grips 313 and 314. Mechanical deformation of the implant 300 may include cooling of the implant 300 whereby the implant 300 transitions from its austenite phase to its martensite phase in order to facilitate an easier mechanical deformation of the implant 300 from the natural shape 301 to the insertion shape 302 prior to an engagement of the implant retainer 311 with the implant 300.

After mechanical deformation of the implant 300 from the natural shape 301 to the insertion shape 302, the forceps 312 using the handles 315 and 316 are positioned with the first and second implant grips 313 and 314 at the front faces 327 of the plates 324 respectively residing adjacent the first and second sides 18 and 19 of the implant 300. In addition, the forceps 312 are positioned with the second flanges 329 of the first and second implant grips 313 and 314 aligned respectively with the first and second grooves 303 and 304 of the implant 300. Upon an actuation of the forceps 312, which includes a manipulation of the handles 315 and 316 through a closing thereof via squeezing, the first and second implant grips 313 and 314 engage with the implant 300. More particularly, the front faces 327 of the first and second implant grips 313 and 314 respectively move into abutting relationship with the first and second sides 18 and 19 such that the first flanges 328 abut the upper surface 16 of the bridge 15 and the second flanges 329 respectively insert into the first and second grooves 303 and 304. Once the first and second implant grips 313 and 314 respectively engage the implant 300, an engagement of the locking ratchet 317 locks the forceps 312 at the first and second implant grips 313 and 314 with the implant 300 whereby the forceps 312, due to the first and second flanges 328 and 329 of the first and second implant grips 313 and 314 extending past the first and second sides 30 and 31 of the transition section 22, constrain the implant 300 in the insertion shape 302 thereby preventing the implant 300 from returning to the natural shape 301. After constraining the implant 300 in the insertion shape 302, drill guides may be secured respectively with the implant 300 using the first and second openings 24 and 25 thereof in order to assist in the drilling of holes into bone, bones, or bone pieces.

In accordance with the orthopedic fixation system 10, the implant retainer 311, when engaged with the implant 300 in that the forceps 312 are locked on the implant 300 at the first and second implant grips 313 and 314 as previously described, retains the implant 300 in the insertion shape 302 such that the implant 300 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the forceps 312 then places the implant 300 across the first bone and the second bone with the transition section 22 of the bridge 15 located at the fixation zone. Upon placement of the implant 300 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 300. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 300 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 300 at the anchoring segment 27 with the second bone.

In light of the affixation of the implant 300 with the first and second bones across the fixation zone, the surgeon removes the implant retainer 311 from the implant 300. More particularly, the surgeon releases the locking ratchet 317 and removes the forceps 312 at the first and second implant grips 313 and 314 from the implant 300. Upon the removal of the implant retainer 311 from the implant 300, the implant 300 attempts transition from the insertion shape 302 to the natural shape 301 whereby the implant 300 delivers the energy stored in the transition section 22 to the first bone and the second bone, resulting in the implant 300 affixing the first bone and the second bone through an application of a compressive force to the fixation zone. The implant retainer 311 accordingly improves insertion of the implant 300 because the implant retainer 311 does not release its constraint of the implant 300 until the implant 300 is affixed to the first and second bones with its transition section 22 located across the fixation zone thereof such that the implant retainer 311 prevents the implant 300 from prematurely delivering the energy stored therein to the first and second bones at the fixation zone thereof. Moreover, the inclusion of the first and second grooves 303 and 304 in the implant 300 that receive therein one of the second flanges 329 improves implantation of the implant 300 because the insertion of the second flanges 329 into the first and second grooves 303 and 304 permits securing of the implant 300 in the insertion position 302 with bone, bones, or bone pieces and then subsequent removal of the implant retainer 311 from the implant 300 while the implant 300 sits flush atop the bone, bones, or bone pieces.

Figures 25A, 25B, 25C, 25D:
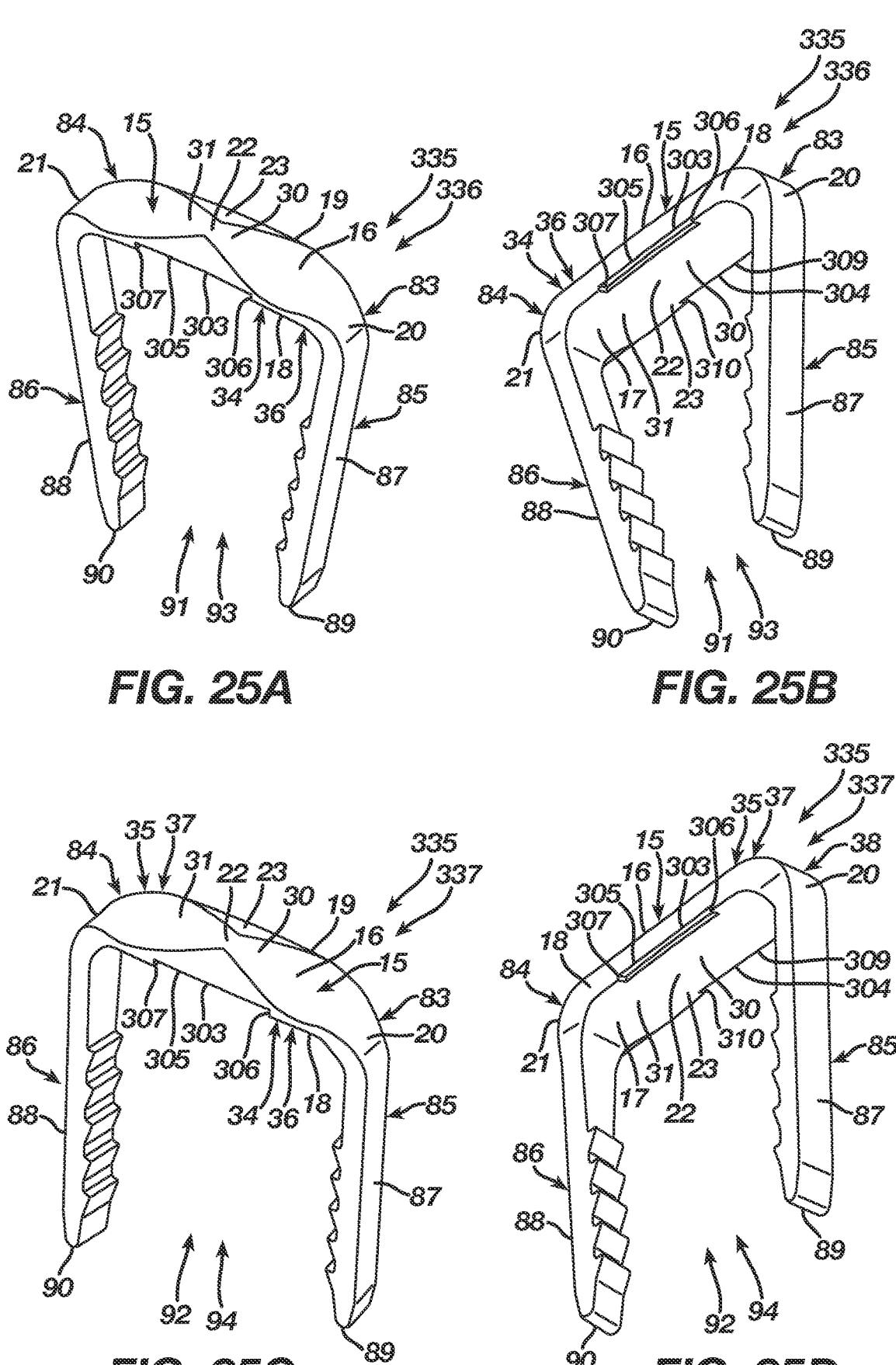
FIG. 25A is a top isometric view illustrating an orthopedic implant according to an eighth embodiment in a natural shape.
FIG. 25B is a bottom isometric view illustrating the orthopedic implant according to the eighth embodiment in the natural shape.
FIG. 25C is a top isometric view illustrating the orthopedic implant according to the eighth embodiment in an insertion shape.
FIG. 25D is a bottom isometric view illustrating the orthopedic implant according to the eighth embodiment in the insertion shape.

FIGS. 25A-25B illustrate an orthopedic implant 335 according to an eighth embodiment in a natural shape 336, whereas FIGS. 25C-25D illustrates the orthopedic implant 335 in an insertion shape 337. The implant 335 is substantially similar in design and operation relative to the orthopedic implant 80 according to the fourth embodiment such that, for the sake of brevity, only differences therebetween will be described herein. Moreover, one of ordinary skill in the art will recognize that like parts of the implant 335 labeled with like numerals of the implant 80 incorporate a design and function as previously set forth in the detailed description of the implant 80 according to the fourth embodiment. While the implant 80 includes the first and second apertures 28 and 29 and the catches 32 and 33 thereof in order to facilitate a securing of the implant 80 with an implant retainer, the implant 335 eliminates the first and second apertures 28 and 29 and the catches 32 and 33 in favor of the first and second grooves 303 and 304 as previously set forth with respect to the implant 300 according to the seventh embodiment.

Figure 26A:
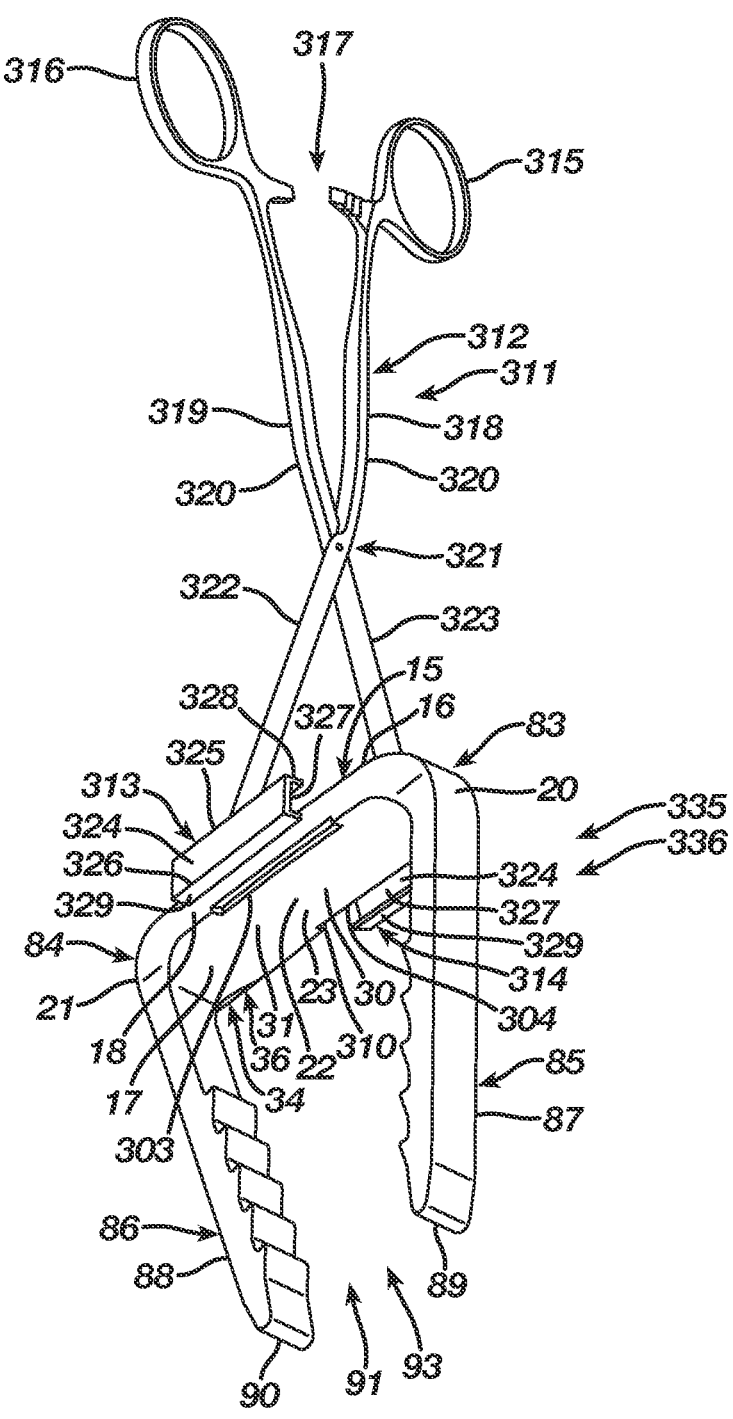
FIG. 26A is a bottom isometric view illustrating the implant retainer according to the eighth embodiment and the orthopedic implant according to the eighth embodiment in the natural shape.
Figure 26B:
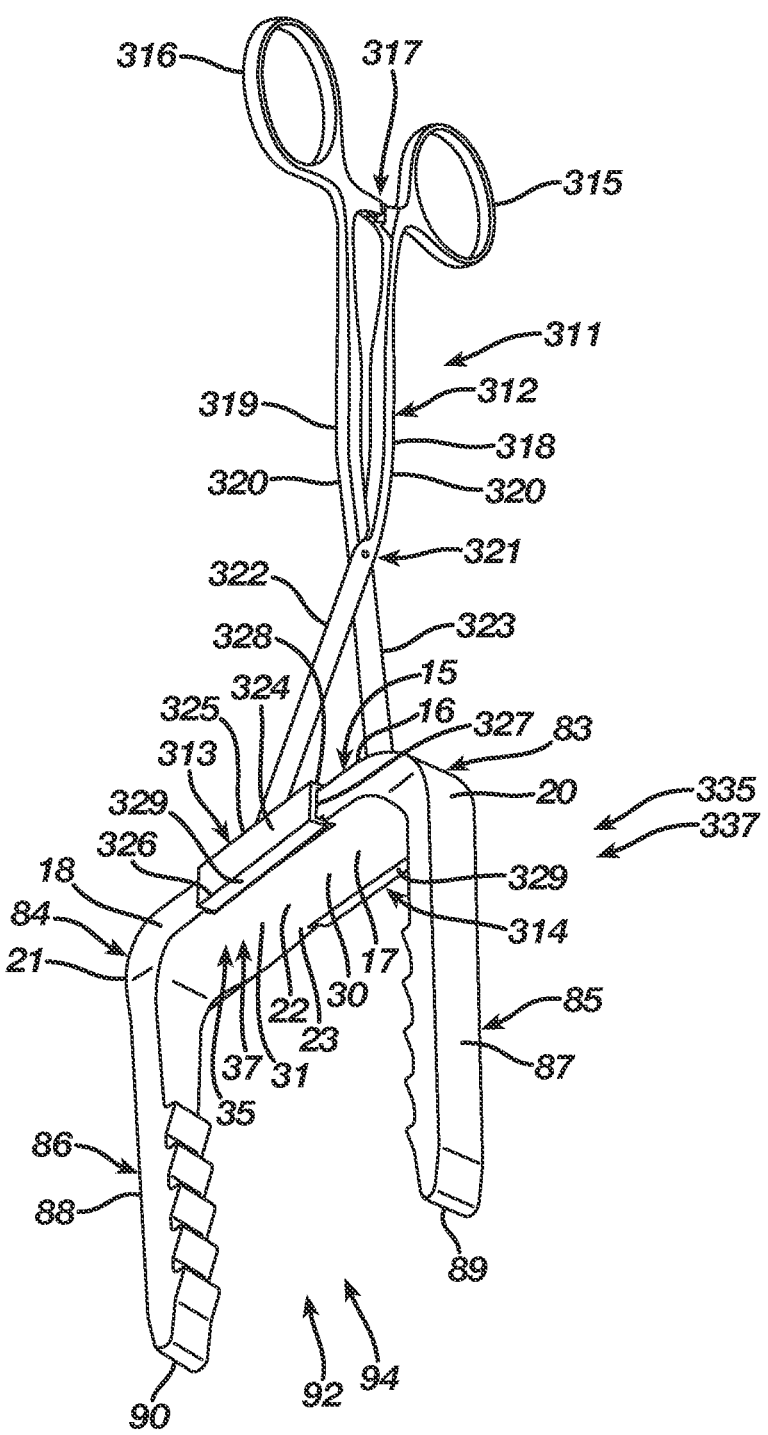
FIG. 26B is a bottom isometric view illustrating the implant retainer according to the eighth embodiment and the orthopedic implant according to the eighth embodiment in the insertion shape forming the orthopedic fixation system.

FIGS. 26A-26B illustrate the implant retainer 311 according to the eighth embodiment and the orthopedic implant 335 according to the eighth embodiment utilized in forming the orthopedic fixation system 10. In accordance therewith, the implant retainer 311, which comprises the forceps 312, engages with and disengages from the implant 335 as previously set forth with respect to the implant 300 according to the eighth embodiment. When securing the implant 335 with bone, bones, or bone pieces, and, in particular, with a first bone and a second bone, the drill holes formed in the first and second bones respectively receive therein the first and second legs 87 and 88 of the implant 335 located in the insertion position 92 prior to the implant retainer 311 releasing the implant 335 for attempted transition from the insertion shape 337 to the natural shape 336 whereby the implant 335 delivers the energy stored in the transition section 22 to the first bone and the second bone, resulting in the implant 335 affixing the first bone and the second bone through an application of a compressive force thereto. The inclusion of the first and second grooves 303 and 304 in the implant 335 that receive therein one of the second flanges 329 improves implantation of the implant 335 because the insertion of the second flanges 329 into the first and second grooves 303 and 304 permits implanting of the implant 335 in the insertion position 337 into bone, bones, or bone pieces using the implant retainer 311 without having to tamp the implant 335 after removal of the implant retainer 311.

Figures 27A, 27B, 27C, 27D, 28A, 28B, 28C:
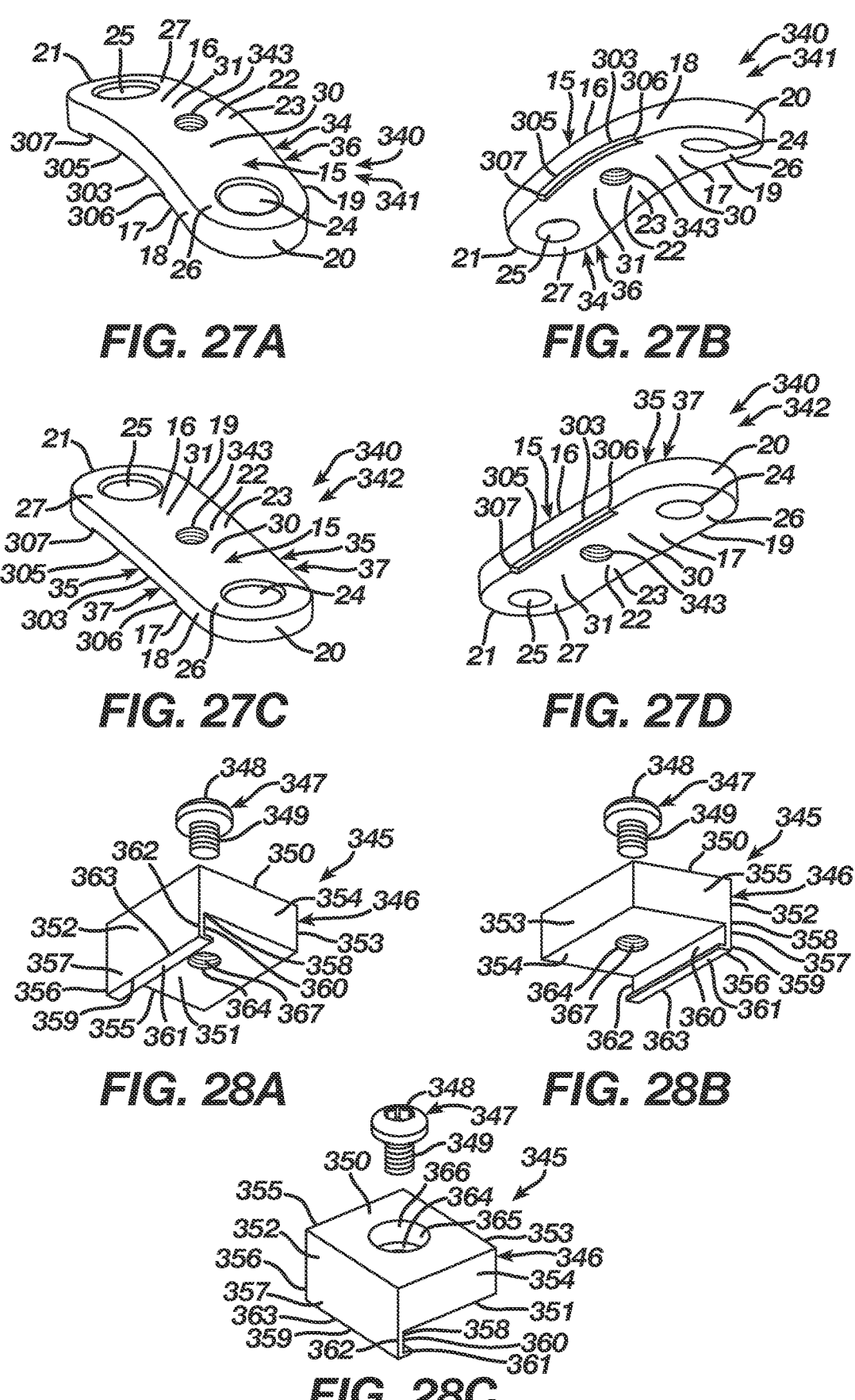
FIG. 27A is a top isometric view illustrating an orthopedic implant according to an alternative of the seventh embodiment in a natural shape.
FIG. 27B is a bottom isometric view illustrating the orthopedic implant according to the alternative of the seventh embodiment in the natural shape.
FIG. 27C is a top isometric view illustrating the orthopedic implant according to the alternative of the seventh embodiment in an insertion shape.
FIG. 27D is a bottom isometric view illustrating the orthopedic implant according to the alternative of the seventh embodiment in the insertion shape.
FIGS. 28A-28B are bottom isometric views illustrating an implant retainer according to an alternative of the eighth embodiment.
FIG. 28C is a top isometric view illustrating the implant retainer according to the alternative of the eighth embodiment.

FIGS. 27A-27B illustrate an orthopedic implant 340 according to an alternative of the seventh embodiment in a natural shape 341, whereas FIGS. 27C-27D illustrates the orthopedic implant 340 in an insertion shape 342. The implant 340 is substantially similar in design and operation relative to the orthopedic implant 300 according to the seventh embodiment such that, for the sake of brevity, only differences therebetween will be described herein. Moreover, one of ordinary skill in the art will recognize that like parts of the implant 340 labeled with like numerals of the implant 300 incorporate a design and function as previously set forth in the detailed description of the implant 300 according to the seventh embodiment. While the implant 300 includes the first and second grooves 303 and 304 in order to facilitate a securing of the implant 300 with the implant retainer 311, the implant 340 includes only the first groove 303 as previously set forth with respect to the implant 300 according to the seventh embodiment, hereinafter referred to as the groove 303, thereby eliminating the second groove 304 since the implant 340 uses only the groove 303 during a securing of the implant 340 with an implant retainer. Although the implant 340 includes only the groove 303, one of ordinary skill in the art will recognize that the implant 340 may include the groove 304 in order to provide an alternative point of securing for an implant retainer with the implant 340. In addition to the groove 303, the implant 340, and thus the bridge 15 thereof, includes a securing feature in the form of an aperture 343, which is preferably threaded, extending therethrough from the upper surface 16 to the lower surface 17. The aperture 343 preferably is located at the center section 23 of the bridge 15 in a position equidistant from the first and second sides 17 and 18 and the first and second ends 20 and 21. The aperture 343 in combination with the groove 303 provides an engagement point for an implant retainer with the implant 340. In accordance therewith, the aperture 343 is located in the bridge 15 at the transition section 22 such that the aperture 343 in combination with the groove 303 facilitates a securing of an implant retainer with the implant 340.

FIGS. 28A-28C illustrate an implant retainer 345 according to an alternative of the eighth embodiment. The implant retainer 345 includes a retention block 346 configured to receive a fastener 347, which preferably is a screw, including a head 348 and a shaft 349 with threads corresponding to the threads disposed in the aperture 343 of the bridge 15 for the implant 340. The retention block 346 preferably is three-dimensional in form including an upper surface 350 and a lower surface 351 with first and second sides 352 and 353 and first and second ends 354 and 355 therebetween. The implant retainer 345 and thus the retention block 346 includes an implant grip 356 extending from the lower surface 351 at the first side 352. The implant grip 356 includes a plate 357 with a top 358, a bottom 359, and a front face 360. The implant grip 356 further includes a flange 361 extending from the plate 357 at the bottom 359 thereof. The implant grip 356 integrates with the lower surface 351 at the top 358 of the plate 357 whereby the plate 357 at the front face 360 and the flange 361 face inward relative to the retention block 346. The implant grip 356 with respect to a height 362 of the plate 357 is correspondingly sized relative to the first side 18 of the bridge 15 such that an engagement of the implant grip 356 with the implant 340 results in the front face 360 abutting the first side 18 whereby the flange 361 extends over the lower surface 17 while fitting within the groove 303. Moreover, the implant grip 356 with respect to a length 363 of the plate 357 and thus the flange 361 as well as the retainer block 346 is correspondingly sized relative to the length 305 of the groove 303 such that an engagement of the first implant grip 356 with the implant 340 results in the flange 361 fitting within the groove 303 such that the implant grip 356 is longer than the transition section 22 in order for the implant retainer 345 to constrain the implant 340 in the insertion shape 342. The retention block 346 may be manufactured from any suitable rigid material, including but not limited to biocompatible metal or metal alloy, such as, for example, titanium, stainless steel, titanium alloy, and cobalt chrome alloy. While the retention block 346 is configured to fit atop the bridge 15 of the implant 340 with the front face 360 abutting the first side 18 and the flange 361 inserted within the groove 303, the dimensions of the retention block 346 are selected to provide the retention block 346 with a mechanical strength and rigidness sufficient to constrain the implant 340 in the insertion shape 342.

The retention block 346 includes a fastener receiving feature in the form of a hole 364 extending therethrough from the upper surface 350 to the lower surface 351. The hole 364 includes a counterbore 365 at an upper segment 366 thereof configured to receive therein the head 348 of the fastener 347 and threads at a lower segment 367 thereof that correspond to the threads on the shaft 349 of the fastener 347. The implant retainer 345 with respect to the retention block 346 and the fastener 347 and the implant 340 with respect to the aperture 343 in the bridge 15 are correspondingly designed with respect to their size, location, and distances to interact and engage such that the implant retainer 345 optimally constrains the bridge 15 in its insertion form 34 and thus the implant 340 in its insertion shape 342. In accordance therewith, when the implant 340 resides in the insertion shape 342, the retention block 346 seats atop the bridge 15 in the insertion form 34 with the hole 364 thereof aligned with the aperture 343 such that the retention block 346 spans the transition section 22 in order to facilitate an engagement of the retention block 346 with the bridge 15 across the transition section 22 using the fastener 347. Moreover, the dimensions of the retention block 346 with respect to a height thereof is selected to provide the retention block 346 with a cross-sectional thickness that facilitates the head 348 of the fastener 347 seating in the counterbore 365 while the shaft 349 extends through the lower segment 367 of the hole 364 and into the aperture 343 to a position whereby the shaft 349 resides at the lower surface 17 of the bridge 15 without protruding therefrom.

FIGS. 29A-29C illustrate the implant retainer 345 according to the alternative of the eighth embodiment and the orthopedic implant 340 according to the alternative of the seventh embodiment utilized in forming the orthopedic fixation system 10. Forming the orthopedic fixation system 10 includes mechanically deforming the implant 340 from the natural shape 341 to the insertion shape 342. More particularly, the implant 340 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Moreover, the movement of the bridge 15 configures the groove 303 for receipt therein of the implant grips 356. Mechanical deformation of the implant 340 may include cooling of the implant 340 whereby the implant 340 transitions from its austenite phase to its martensite phase in order to facilitate an easier mechanical deformation of the implant 340 from the natural shape 341 to the insertion shape 342 prior to an engagement of the implant retainer 345 with the implant 340.

After mechanical deformation of the implant 340 from the natural shape 341 to the insertion shape 342, the retention block 346 seats atop the bridge 15 at the upper surface 16 thereof in abutting relationship with bridge 15 between the first and second openings 24 and 25 such that the hole 364 aligns with the aperture 343. Moreover, the implant grip 356 at the front face 360 of the plate 357 resides adjacent the first side 18 of the implant 340 such that the flange 361 thereof aligns with the groove 303 of the implant 340. The fastener 347 via a threading therein inserts into the hole 364 until the head 348 seats in the counterbore 365 and the shaft 349 extends through the lower segment 367 and into the aperture 343 to a position whereby the shaft 349 resides at the lower surface 17 of the bridge 15 without protruding therefrom. The engagement of the fastener 347 with both the hole 364 of the retention block 346 and the aperture 343 of the bridge 15 secures the retention block 346 with the bridge 15 across the transition section 22 and the implant grip 356 with the implant 340. More particularly, the front face 327 of the implant grip 356 moves into abutting relationship with the first side 18 such that the flange 361 inserts into the groove 303. Upon engagement of the implant retainer 345 with the implant 340, the retention block 346, due to its spanning of the transition section 22 in combination with the flange 361 of the implant grip 356 extending past the first and second sides 30 and 31 of the transition section 22, constrains the implant 340 in the insertion shape 342 thereby preventing the implant 340 from returning to the natural shape 341. After constraining the implant 340 in the insertion shape 342, drill guides may be secured respectively with the implant 340 using the first and second openings 24 and 25 thereof in order to assist in the drilling of holes into bone, bones, or bone pieces.

In accordance with the orthopedic fixation system 10, the implant retainer 345, when engaged with the implant 340 as previously described, retains the implant 340 in the insertion shape 342 such that the implant 340 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the implant retainer 345 if appropriate then places the implant 340 across the first bone and the second bone with the transition section 22 of the bridge 15 located at the fixation zone. Upon placement of the implant 340 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 340. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 340 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 340 at the anchoring segment 27 with the second bone.

In light of the affixation of the implant 340 with the first and second bones across the fixation zone, the surgeon removes the implant retainer 345 from the implant 340. More particularly, the surgeon removes the fastener 347 from the aperture 343 in the bridge 15 and if desired from the hole 364 of the retention block 346. The surgeon then slides the retention block 346 along the upper surface 16 toward the first side 18 in order to disengage the flange 361 from the groove 303. The surgeon finally withdraws the retention block 346 from atop the implant 340 thereby separating the implant retainer 345 from the implant 340. Upon the removal of the implant retainer 345 from the implant 340, the implant 340 attempts transition from the insertion shape 342 to the natural shape 341 whereby the implant 340 delivers the energy stored in the transition section 22 to the first bone and the second bone, resulting in the implant 340 affixing the first bone and the second bone through an application of a compressive force to the fixation zone.

The implant retainer 345 accordingly improves insertion of the implant 340 because the implant retainer 345 does not release its constraint of the implant 340 until the implant 340 is affixed to the first and second bones with its transition section 22 located across the fixation zone thereof such that the implant retainer 345 prevents the implant 340 from prematurely delivering the energy stored therein to the first and second bones at the fixation zone thereof. Moreover, the inclusion of the groove 303 in the implant 340 that receives therein the flange 361 improves implantation of the implant 340 because the insertion of the flange 361 into the groove 303 permits securing of the implant 340 in the insertion position 342 with bone, bones, or bone pieces and then subsequent removal of the implant retainer 345 from the implant 340 while the implant 340 sits flush atop the bone, bones, or bone pieces.

It should be understood that the orthopedic implant 335 according to the eighth as illustrated in FIGS. 25A-25D may be modified to include the aperture 343 in the bridge 15 as previously described with respect to the implant 340 such that the implant retainer 345 is engageable with the implant 335 as previously described with respect to the implant 340 in order to constrain the implant 335 in the insertion shape 337. The inclusion of the aperture 343 and at least the first groove 303 in the implant 335 that receives therein the flange 361 of the implant grip 356 improves implantation of the implant 335 because the insertion of the flange 361 into the first groove 303 permits implanting of the implant 335 in the insertion position 337 into bone, bones, or bone pieces using the implant retainer 345 without having to tamp the implant 335 after removal of the implant retainer 345.

FIGS. 30A-30B illustrate an orthopedic implant 370 according to an alternative of the seventh embodiment in a natural shape 371, whereas FIGS. 30C-30D illustrates the orthopedic implant 370 in an insertion shape 372. The implant 370 is substantially similar in design and operation relative to the orthopedic implant 340 and further to the orthopedic implant 300 according to the seventh embodiment such that, for the sake of brevity, only differences therebetween will be described herein. Moreover, one of ordinary skill in the art will recognize that like parts of the implant 370 labeled with like numerals of the implant 340 and the implant 300 incorporate a design and function as previously set forth in the detailed description of the implant 340 and the implant 300 according to the seventh embodiment. While the implant 340 includes only the first groove 303 and the implant 300 includes the first and second grooves 303 and 304 in order to facilitate a securing of the implant 340 and the implant 300 respectively with the implant retainer 345 and the implant retainer 311, the implant 370 includes the first groove 303 reduced in length to produce the first groove 373 residing between the second side 31 of the transition section 22 and the second opening 25. Likewise, the implant 370 includes the second groove 304 reduced in length to produce the second groove 374 residing between the first side 30 of the transition section 22 and the first opening 24. The first groove 373 extends exterior of the second side 31 of the transition section 22 and the second groove 374 extends exterior of the first side 30 of the transition section 22 in order for an implant retainer secured with the implant 370 at the aperture 343 thereof to constrain the implant 370 in the insertion shape 372. Although the implant 370 includes the first and second grooves 373 and 374 reduced in length relative to the first and second grooves 303 and 304, one of ordinary skill in the art will recognize that an implant 370 including the first and second grooves 303 and 304 can be constrained by an implant retainer secured with the implant 370 at the aperture 343.

Figure 31A:
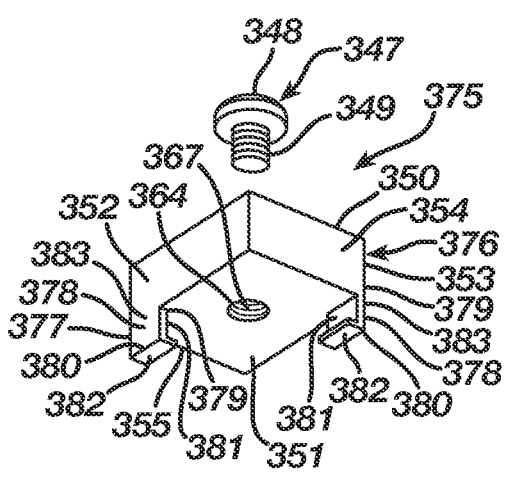
FIG. 31A is a top isometric view illustrating an implant retainer according to an alternative of the eighth embodiment.
Figure 31B:
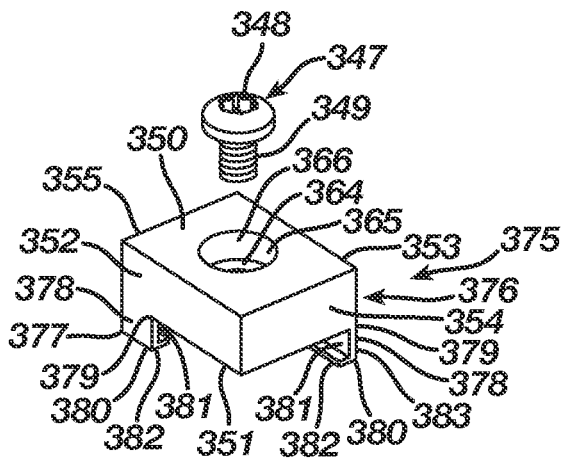
FIG. 31B is a bottom isometric view illustrating the implant retainer according to the alternative of the eighth embodiment.

FIGS. 31A-31B illustrate an implant retainer 375 according to an alternative of the eighth embodiment including a retention block 376 configured to receive the fastener 347. The implant retainer 375 and the retention block 376 are substantially similar in design and operation relative to the implant retainer 345 and the retention block 346 such that, for the sake of brevity, only differences therebetween will be described herein. Moreover, one of ordinary skill in the art will recognize that like parts of the implant retainer 375 and the retention block 376 labeled with like numerals of the implant retainer 345 and the retention block 346 incorporate a design and function as previously set forth in the detailed description of the implant retainer 345 and the retention block 346. While the implant retainer 345 and thus the retention block 346 includes the implant grip 356 in order to facilitate a securing of the implant retainer 345 with the implant 340, the implant retainer 375 and thus the retention block 376 includes first and second implant grips 377 and 383 in order to facilitate a securing of the implant retainer 375 with the implant 370.

The first implant grip 377 extends from the lower surface 351 at the first side 352 adjacent the second end 355. The first implant grip 377 includes a plate 378 with a top 379, a bottom 380, and a front face 381. The first implant grip 377 further includes a flange 382 extending from the plate 378 at the bottom 380 thereof. The first implant grip 377 integrates with the lower surface 351 adjacent the second end 355 at the top 379 of the plate 378 whereby the plate 378 at the front face 381 and the flange 328 face inward relative to the retention block 376. The first implant grip 377 with respect to a height 383 of the plate 378 is correspondingly sized relative to the first and second sides 18 and 19 of the bridge 15 such that an engagement of the first implant grip 377 with the implant 370 results in the front face 381 abutting the first side 18 or the second side 19 whereby the flange 361 extends over the lower surface 17 while fitting within one of the first groove 373 and the second groove 374.

The second implant grip 383 is substantially similar in design and operation relative to the first implant grip 377 such that, for the sake of brevity, only differences therebetween will be described herein. Moreover, one of ordinary skill in the art will recognize that like parts of the second implant grip 383 labeled with like numerals of the first implant grip 377 incorporate a design and function as previously set forth in the detailed description of the first implant grip 377. The second implant grip 383 extends from the lower surface 351 at the second side 353 adjacent the first end 354. The second implant grip 383 integrates with the lower surface 351 adjacent the first end 354 at the top 379 of the plate 378 whereby the plate 378 at the front face 381 and the flange 328 face inward relative to the retention block 376. The second implant grip 383, due to the location thereof at the second side 353 adjacent the first end 354, and the first implant grip 377, due to the location thereof at the first side 352 adjacent the second end 355, reside diagonal relative to the retention block 376. In accordance therewith, when the first implant grip 377 at the flange 382 engages one of the first groove 373 and the second groove 374 and the second implant grip 383 at the flange 382 engages the opposite one of the first groove 373 and the second groove 374, the retention block 376 and thus the implant retainer 375 constrains the implant 370 in the insertion shape 302 because the first implant grip 377 and the second implant grip 383 grasp the implant 370 at the first and second sides 18 and 19 exterior of the first and second sides 30 and 31 of the transition section 22.

Figure 32A:
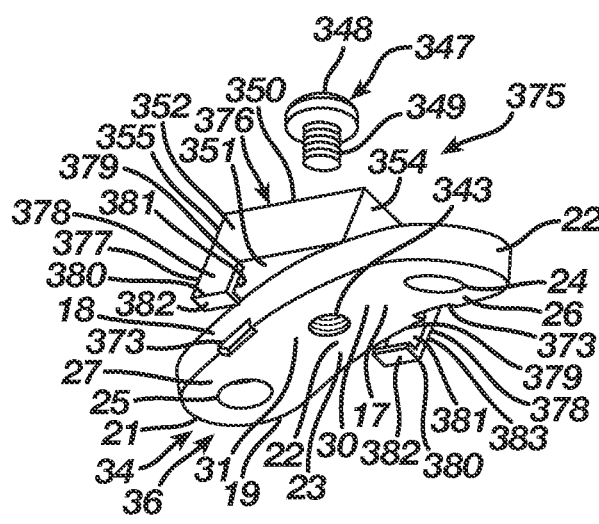
FIG. 32A is a bottom isometric view illustrating the implant retainer according to the alternative of the eighth embodiment and the orthopedic implant according to the alternative of the seventh embodiment in the natural shape forming the orthopedic fixation system.
Figure 32B:
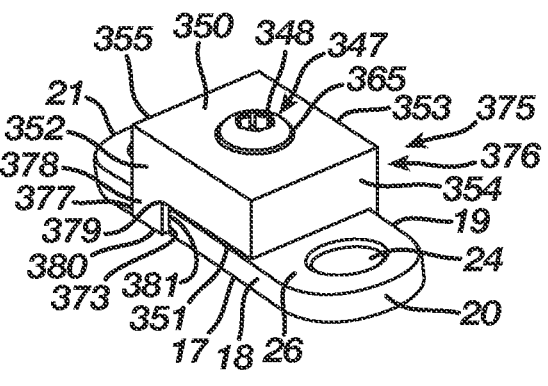
FIG. 32B is a top isometric view illustrating the implant retainer according to the alternative of the eighth embodiment and the orthopedic implant according to the alternative of the seventh embodiment in the insertion shape forming the orthopedic fixation system.
Figure 32C:
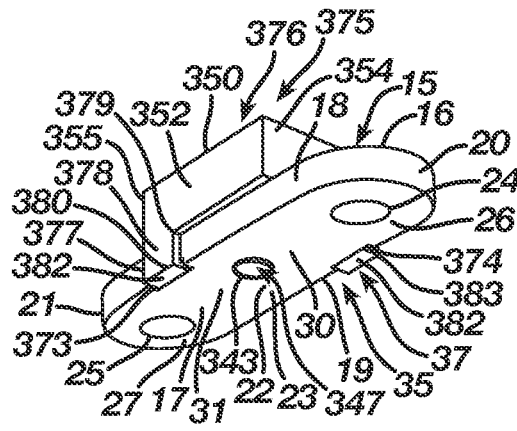
FIG. 32C is a bottom isometric view illustrating the implant retainer according to the alternative of the eighth embodiment and the orthopedic implant according to the alternative of the seventh embodiment in the insertion shape forming the orthopedic fixation system.

FIGS. 32A-32C illustrate the implant retainer 375 according to the alternative of the eighth embodiment and the orthopedic implant 370 according to the alternative of the seventh embodiment utilized in forming the orthopedic fixation system 10. Forming the orthopedic fixation system 10 includes mechanically deforming the implant 370 from the natural shape 371 to the insertion shape 372. More particularly, the implant 370 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Moreover, the movement of the bridge 15 configures the first and second grooves 373 and 374 for receipt therein of one of the first and second implant grips 377 and 383. Mechanical deformation of the implant 370 may include cooling of the implant 370 whereby the implant 370 transitions from its austenite phase to its martensite phase in order to facilitate an easier mechanical deformation of the implant 370 from the natural shape 371 to the insertion shape 372 prior to an engagement of the implant retainer 375 with the implant 370.

After mechanical deformation of the implant 370 from the natural shape 371 to the insertion shape 372, the retention block 376 seats atop the bridge 15 at the upper surface 16 thereof in abutting relationship with bridge 15 between the first and second openings 24 and 25 such that the hole 364 aligns with the aperture 343. Nevertheless, the retention block 376 is initially seated in misalignment with the bridge 15 in order for the first implant grip 377 at the flange 382 thereof to bypass the bridge 15 at the first side 18 and the second implant grip 383 at the flange 382 thereof to bypass the bridge 15 at the second side 18. The retention block 376 then pivots relative to the bridge 15 into alignment therewith such that the first implant grip 377 at the front face 381 of the plate 378 resides adjacent the first side 18 of the implant 370 while the flange 382 aligns with the first groove 373 of the implant 373. Likewise, the second implant grip 377 at the front face 381 of the plate 378 resides adjacent the second side 19 of the implant 370 while the flange 382 aligns with the second groove 374 of the implant 373. The fastener 347 via a threading therein inserts into the hole 364 until the head 348 seats in the counterbore 365 and the shaft 349 extends through the lower segment 367 and into the aperture 343 to a position whereby the shaft 349 resides at the lower surface 17 of the bridge 15 without protruding therefrom. The engagement of the fastener 347 with both the hole 364 of the retention block 376 and the aperture 343 of the bridge 15 secures the retention block 376 with the bridge 15 across the transition section 22 and the first and second implant grips 377 and 383 with the implant 370. More particularly, the front face 381 of the first implant grip 377 moves into abutting relationship with the first side 18 such that the flange 382 inserts into the first groove 373, whereas the front face 381 of the second implant grip 383 moves into abutting relationship with the second side 19 such that the flange 382 inserts into the second groove 374. Upon engagement of the implant retainer 375 with the implant 370, the retention block 376, due to its spanning of the transition section 22 in combination with the flange 382 of the first implant grip 377 inserting into the first groove 373 exterior of the second side 31 of the transition section 22 and the flange 382 of the second implant grip 383 inserting into the second groove 374 exterior of the first side 31 of the transition section 22, constrains the implant 370 in the insertion shape 372 thereby preventing the implant 370 from returning to the natural shape 371. One of ordinary skill in the art will recognize the retention block 376 may be seated atop the bridge 15 with the flange 382 of the first implant grip 377 inserted into the second groove 374 and the flange 382 of the second implant grip 383 inserted into the first groove 373. After constraining the implant 370 in the insertion shape 372, drill guides may be secured respectively with the implant 370 using the first and second openings 24 and 25 thereof in order to assist in the drilling of holes into bone, bones, or bone pieces.

In accordance with the orthopedic fixation system 10, the implant retainer 375, when engaged with the implant 370 as previously described, retains the implant 370 in the insertion shape 372 such that the implant 370 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. The surgeon using the implant retainer 375 if appropriate then places the implant 370 across the first bone and the second bone with the transition section 22 of the bridge 15 located at the fixation zone. Upon placement of the implant 370 with the first opening 24 thereof at the first bone and the second opening 25 thereof at the second bone, the surgeon forms a drill hole in the first bone at the first opening 24 and a drill hole in the second bone at the second opening 25. The surgeon, if drill guides were used, removes the drill guides from the first and second openings 24 and 25 of the implant 370. With drill holes formed in the first and second bones, the surgeon inserts, via an insertion tool such as a screwdriver, an anchoring member in the form of a screw through the first opening 25 and into the first bone until the screw at a head thereof resides substantially, completely within the first opening 25, whereby the screw affixes the implant 370 at the anchoring segment 26 with the first bone. Likewise, the surgeon inserts, via an insertion tool such as a screwdriver, an anchoring member in the form of a screw through the second opening 25 and into the second bone until the screw at a head thereof resides substantially, completely within the second opening 25, whereby the screw affixes the implant 370 at the anchoring segment 27 with the second bone.

In light of the affixation of the implant 370 with the first and second bones across the fixation zone, the surgeon removes the implant retainer 375 from the implant 370. More particularly, the surgeon removes the fastener 347 from the aperture 343 in the bridge 15 and if desired from the hole 364 of the retention block 376. The surgeon then pivots the retention block 376 about the bridge 15 in order to disengage the flange 382 of the first implant grip 377 from the first groove 373 and the flange 382 of the second implant grip 383 from the second groove 374. The surgeon finally withdraws the retention block 376 from atop the implant 370 thereby separating the implant retainer 375 from the implant 370. Upon the removal of the implant retainer 375 from the implant 370, the implant 370 attempts transition from the insertion shape 372 to the natural shape 371 whereby the implant 370 delivers the energy stored in the transition section 22 to the first bone and the second bone, resulting in the implant 370 affixing the first bone and the second bone through an application of a compressive force to the fixation zone.

The implant retainer 375 accordingly improves insertion of the implant 370 because the implant retainer 375 does not release its constraint of the implant 370 until the implant 370 is affixed to the first and second bones with its transition section 22 located across the fixation zone thereof such that the implant retainer 375 prevents the implant 370 from prematurely delivering the energy stored therein to the first and second bones at the fixation zone thereof. Moreover, the inclusion of the first and second grooves 373 and 374 in the implant 370 that receive therein one of the flanges 382 of the first and second grips 377 and 383 improves implantation of the implant 370 because the insertion of the flanges 382 into the first and second grooves 373 and 374 permits securing of the implant 370 in the insertion position 372 with bone, bones, or bone pieces and then subsequent removal of the implant retainer 375 from the implant 370 while the implant 370 sits flush atop the bone, bones, or bone pieces.

It should be understood that the orthopedic implant 335 according to the eighth as illustrated in FIGS. 25A-25D may be modified to include the aperture 343 in the bridge 15 as previously described with respect to the implant 370 such that the implant retainer 375 is engageable with the implant 335 as previously described with respect to the implant 370 in order to constrain the implant 335 in the insertion shape 337. The inclusion of the aperture 343 and the first and second grooves 373 and 374 in the implant 335 that receive therein one of the flanges 382 of the first and second implant grips 377 and 383 improves implantation of the implant 335 because the insertion of the flanges 382 into the first and second grooves 373 and 374 permits implanting of the implant 335 in the insertion position 337 into bone, bones, or bone pieces using the implant retainer 375 without having to tamp the implant 335 after removal of the implant retainer 375.

Figure 33A:
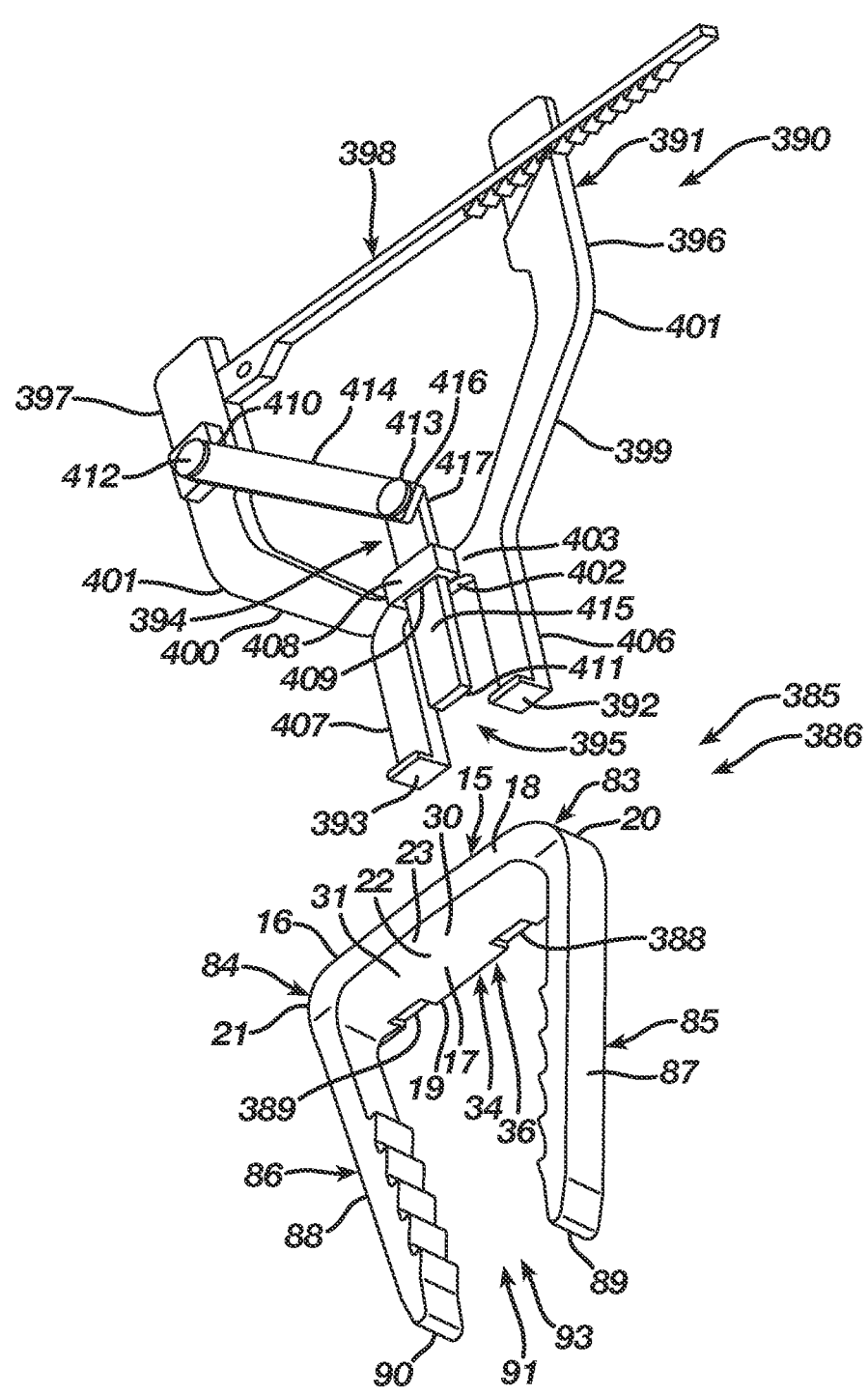
FIG. 33A is a bottom isometric view illustrating an implant retainer according to a ninth embodiment and an orthopedic implant according to a ninth embodiment in the natural shape.
Figure 33B:
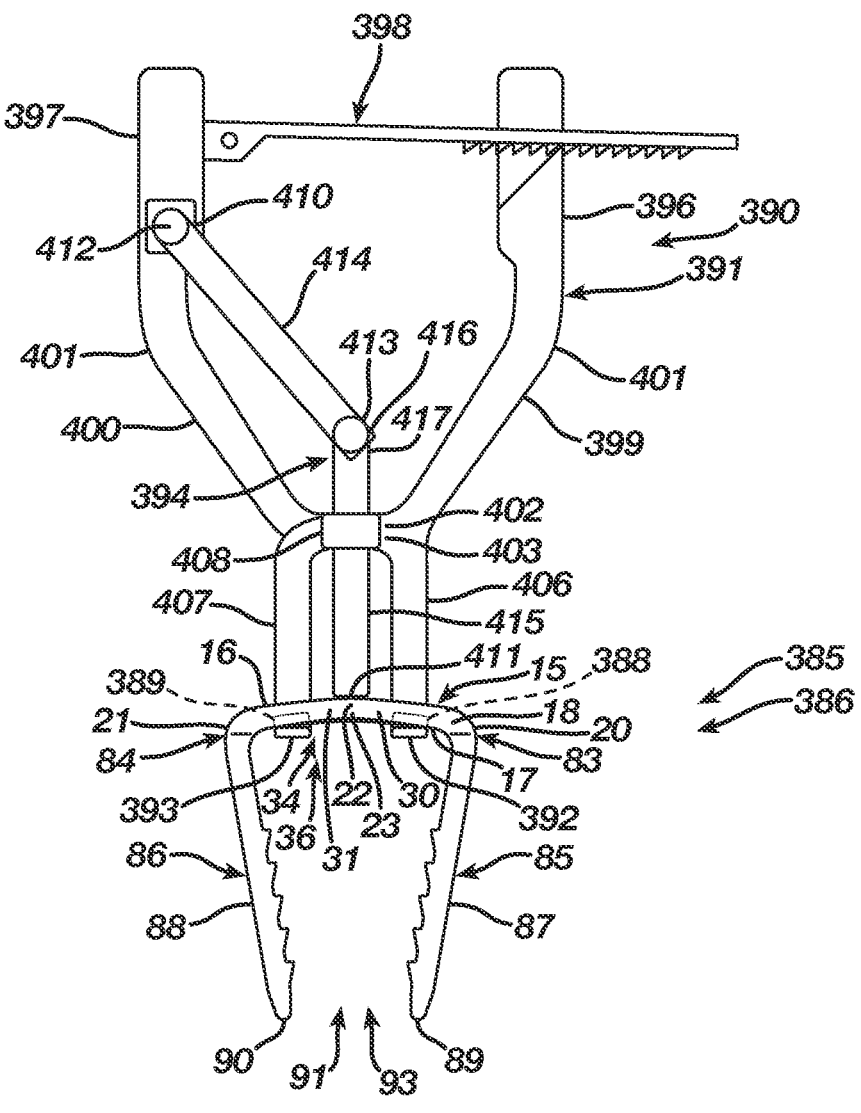
FIG. 33B is a front view illustrating the implant retainer according to the ninth embodiment and the orthopedic implant according to the ninth embodiment in the natural shape.
Figure 33C:
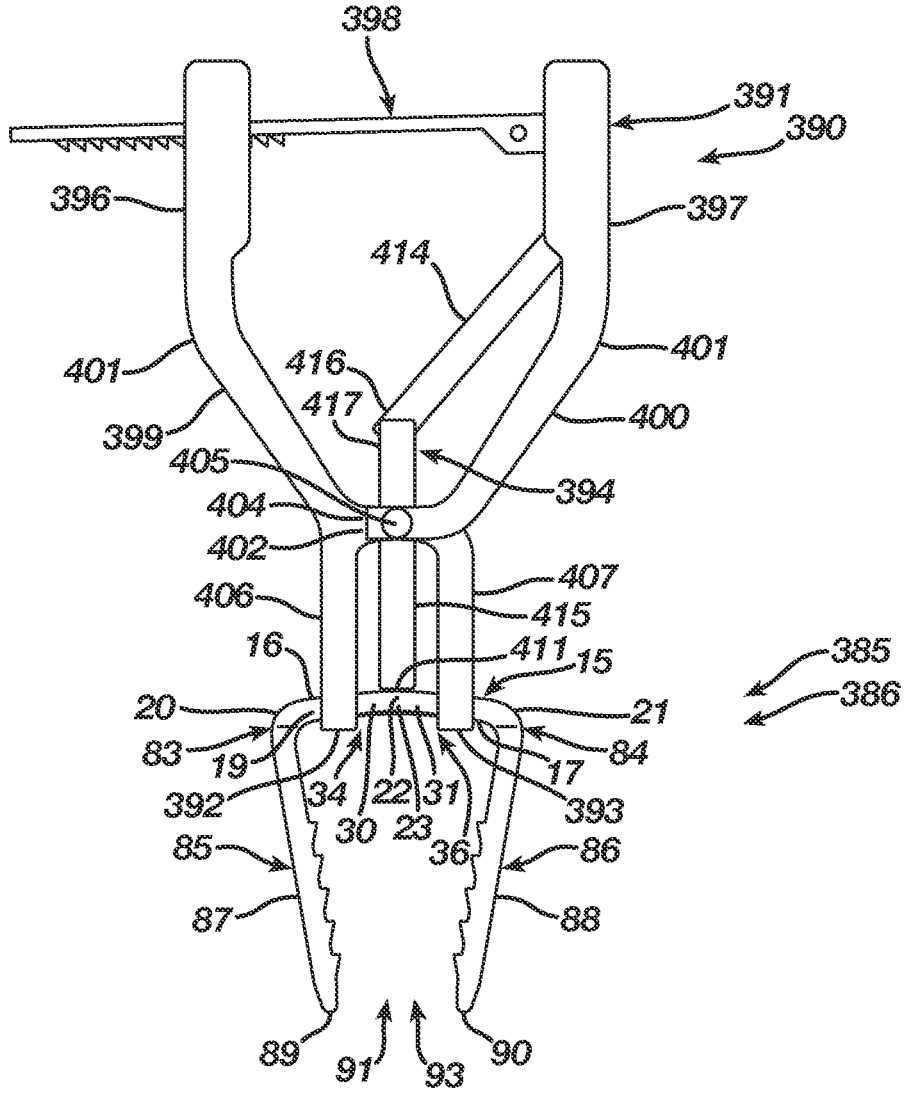
FIG. 33C is a rear view illustrating the implant retainer according to the ninth embodiment and the orthopedic implant according to the ninth embodiment in the natural shape.
Figure 34A:
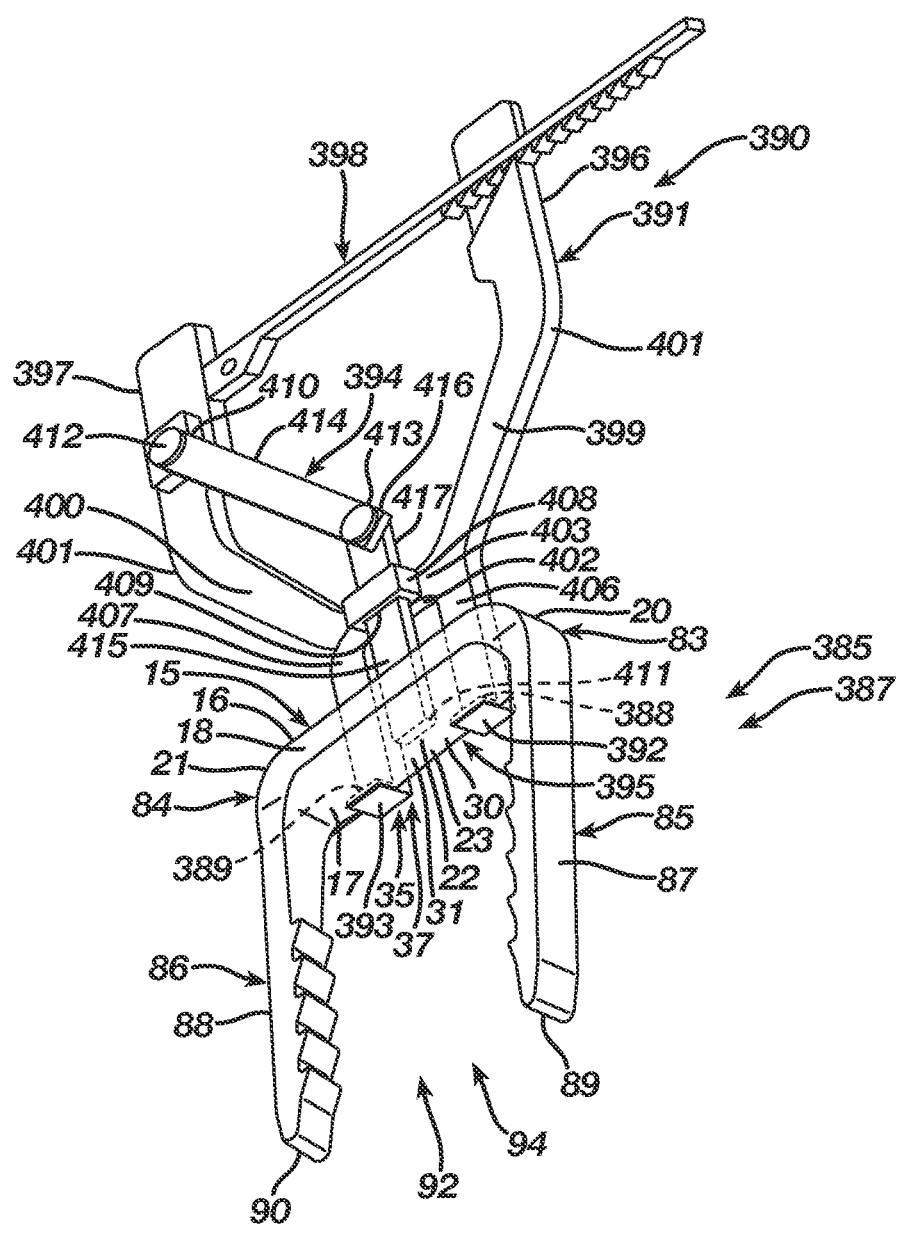
FIG. 34A is a bottom isometric view illustrating the implant retainer according to the ninth embodiment and the orthopedic implant according to the ninth embodiment in an insertion shape forming the orthopedic fixation system.
Figure 34B:
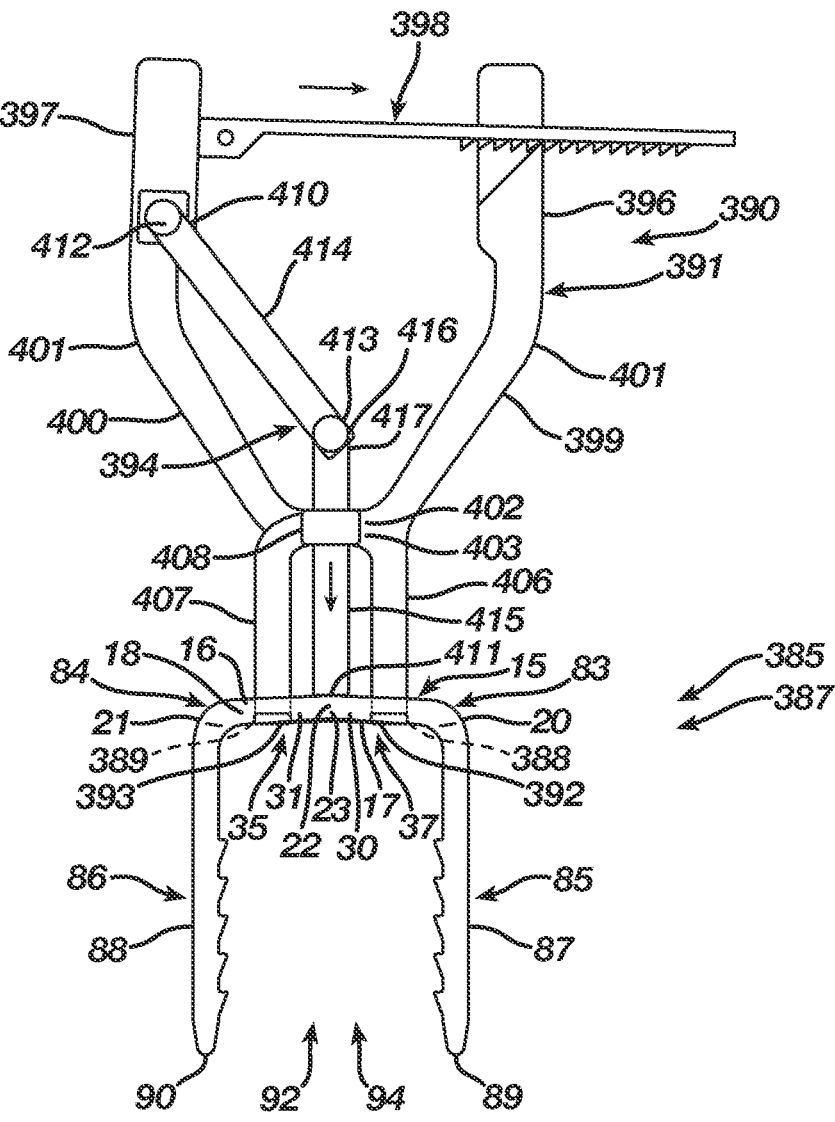
FIG. 34B is a front view illustrating the implant retainer according to the ninth embodiment and the orthopedic implant according to the ninth embodiment in the insertion shape forming the orthopedic fixation system.

FIGS. 33A-34B illustrate the orthopedic fixation system 10 including an orthopedic implant 385 according to a ninth embodiment and an implant retainer 390 according to a ninth embodiment. The orthopedic implant 385 according to the ninth embodiment includes a natural shape 386 as illustrated in FIGS. 33A-33C and an insertion shape 387 as illustrated in FIGS. 34A-34B. The implant 385 is substantially similar in design and operation relative to the orthopedic implant 80 according to the fourth embodiment such that, for the sake of brevity, only differences therebetween will be described herein. Moreover, one of ordinary skill in the art will recognize that like parts of the implant 385 labeled with like numerals of the implant 80 incorporate a design and function as previously set forth in the detailed description of the implant 80 according to the fourth embodiment. While the implant 80 includes the first and second apertures 28 and 29 and the catches 32 and 33 thereof in order to facilitate a securing of the implant 80 with an implant retainer, the implant 385 eliminates the first and second apertures 28 and 29 and the catches 32 and 33 in favor of securing features in the form of first and second grooves 388 and 389 configured to engage with the implant retainer 390. The first groove 388 is cut into the lower surface 17 of the bridge 15 along the second side 19 thereof exterior of the first side 30 of the transition section 22. Likewise, the second groove 389 is cut into the lower surface 17 of the bridge 15 along the second side 19 thereof exterior of the second side 31 of the transition section 22. The first groove 388 and the second groove 389 reside respectively exterior of the first side 30 and the second side 31 of the transition section 22 in order for the implant retainer 390 to constrain the implant 385 in the insertion shape 387.

The implant retainer 390 in the ninth embodiment comprises forceps 391 including first and second hooks 392 and 393, each of which is configured to engage with the implant 385, and a plunger 394 movable into engagement with the implant 385 at the transition section 22. The first and second hooks 392 and 393, which, in the ninth embodiment, extend substantially, completely perpendicular from the forceps 391, are spaced apart a distance 395 that places the first hook 392 exterior of one of the first and second sides 30 and 31 of the transition section 22 and the second hook 393 exterior of the opposite one of the first and second sides 30 and 31 of the transition section 22. The first and second hooks 392 and 393 and the first and second grooves 388 and 389 are correspondingly sized and spaced apart such that the first hook 392 inserts into one of the first and second grooves 388 and 389 while the second hook 393 inserts into the opposite one of the first and second grooves 388 and 389. The forceps 391 include handles 396 and 397 and a locking ratchet 398 extending between the handles 396 and 397 whereby the locking ratchet 398 is configured to arrest the movement of the handles 396 and 397 thereby locking the forceps 391 in engagement with the implant 385. The forceps 391 include shanks 399 and 400 extending respectively from the handles 396 and 397 at an angle 401 that directs the shanks 399 and 400 towards a convergence thereof. The forceps 391 includes a crossbar 402 extending from the shank 399 towards the shank 400. The crossbar 402 includes a first side 403 and a second side 404 that provides an engagement point for a hinge 405. The hinge 405 secures the shank 400 with the crossbar 402 and thus the shank 399 such that the handle 397 and the shank 400 via the hinge 405 pivot relative to the handle 396 and the shank 399 in order to produce a pivot point for the forceps 391. The forceps 391 include first and second blades 406 and 407 extending from the crossbar 402 whereby the first and second blades 406 and 407 terminate respectively in the first and second hooks 392 and 393, which in the ninth embodiment extend respectively substantially, completely perpendicular from the first and second hooks 392 and 393. The first and second hooks 392 and 393 are spaced apart across the crossbar 402 and extend respectively therefrom such that the first and second hooks 392 and 393 reside at the distance 395. The forceps 391 include a guide 408 defining a guide slot 409 secured centrally with the crossbar 402 at the first side 403 thereof that couples the plunger 394 with the forceps 391 while directing the plunger 394 between the first and second blades 406 and 407.

The plunger 394 includes a proximal end 410 and a distal end 411. The plunger 394 at the proximal end 410 connects with handle 397 using a pin 412 that allows the plunger 394 at the proximal end 410 to pivot relative to the handle 397; although the pin 412 may rigidly secure the plunger 394 with the handle 397. The plunger 394 includes a hinge 413 that directs the plunger 394 through the guide slot 409 of the guide 408 such that the plunger 394 resides between the first and second blades 406 and 407 with the distal end 411 thereof positioned above the first and second hooks 392 and 393. The plunger 394 includes a drive arm 414 incorporating the proximal end 410 and a plunger arm 415 inserted through the guide 408 via the guide slot 409 and incorporating the distal end 411. The hinge 413 pivotally couples the drive arm 414 with the plunger arm 415 at ends 416 and 417 opposite respectively to the proximal end 410 and the distal end 411.

Actuation of the forceps 391 and thus the plunger 394 includes a manipulation of the handle 397 relative to the handle 396, resulting in the hinge 413 translating a pivotal motion of the handle 397 into a reciprocating motion of the plunger 394 whereby the plunger 394 moves linearly either towards the first and second hooks 392 and 393 or away from the first and second hooks 392 and 393. In the implant retainer 390 according to the ninth embodiment, manipulation of the handle 397 relative to the handle 396 consists of closing the handles 396 and 397 and thus the forceps 391 such that the hinge 413 translates the pivotal motion of the handle 397, which is imparted to the plunger 394 via the connection thereof with the handle 397, into the reciprocating motion of the plunger 394 whereby the plunger 394 moves linearly towards the first and second hooks 392 and 393. More particularly, the pivotal motion of the handle 397 moves the drive arm 414 at the proximal end 410 toward the hinge 413, causing the hinge 413 to push the plunger arm 415 linearly towards the first and second hooks 392 and 393. Conversely, manipulation of the handle 397 relative to the handle 396 consists of opening the handles 396 and 397 and thus the forceps 391 such that the hinge 413 translates a pivotal motion of the handle 397, which is imparted to the plunger 394 via the connection thereof with the handle 397, into a reciprocating motion of the plunger 394 whereby the plunger 394 moves linearly away the first and second hooks 392 and 393. More particularly, the pivotal motion of the handle 397 moves the drive arm 414 at the proximal end 410 away from the hinge 413, causing the hinge 413 to pull the plunger arm 415 linearly away from the first and second hooks 392 and 393.

Forming the orthopedic fixation system 10 includes the implant retainer 390, which comprises the forceps 391, manipulated whereby the plunger 394 is retracted relative to the first and second hooks 392 and 393 such that the plunger 394 will reside above the upper surface 16 of the bridge 15 of the implant 385 and the first and second hooks 392 and 393 will reside below the lower surface 17 of the bridge 15 of the implant 385. The implant 385 then is mechanically deformed from the natural shape 386 to the insertion shape 387. More particularly, the implant 385 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. The movement of the bridge 15 further configures the first and second grooves 388 and 389 for receipt therein of one of the first and second hooks 392 and 393. Moreover, the movement of the bridge 15 progresses the first and second legs 87 and 88 from the natural position 91 where the first and second legs 87 and 88 reside at the first distance 93 to the insertion position 92 where the first and second legs 87 and 88 reside at the second distance 94. Mechanical deformation of the implant 385 may include cooling of the implant 385 whereby the implant 385 transitions from its austenite phase to its martensite phase in order to facilitate an easier mechanical deformation of the implant 385 from the natural shape 386 to the insertion shape 387 prior to an engagement of the implant retainer 390 with the implant 385.

After mechanical deformation of the implant 385 from the natural shape 386 to the insertion shape 387, the forceps 391 using the handles 396 and 397 are positioned relative to the implant 385 such that the first and second hooks 392 and 393 insert under the lower surface 17 of the bridge 15 respectively in alignment with the first and second grooves 388 and 389 while the plunger 394 is located above the upper surface 16 of the bridge 15 at the transition section 22. Once the forceps 391 are positioned, an actuation of the forceps 391, which consists of closing the handles 396 and 397 through a pivoting of the handle 397 towards the handle 396, moves the plunger 394 linearly towards the upper surface 16 of the bridge 15 such that the plunger 394 at the distal end 411 seats atop at the transition section 22. Closing of the forceps 391 continues until the seating of the plunger 394 atop the transition section 22 causes the first and second hooks 392 and 393 respectively to insert into the first and second grooves 388 and 389 and then tighten against the bridge 15. Upon the seating of the plunger 394 and the tightening of the first and second hooks 392 and 393 against the bridge 15, an engagement of the locking ratchet 398 locks the forceps 391 and prevents a release thereof from the implant 385. The locking of the forceps 391 at the plunger 394 and the first and second hooks 392 and 393 thereof with the implant 385 secures the forceps 391 with the implant 385 whereby the forceps 391 constrain the implant 385 in the insertion shape 387 and preclude the implant 385 from returning to the natural shape 386.

In an alternative forming of the orthopedic fixation system 10, the forceps 391 may be utilized to mechanically deform the implant 385 from the natural shape 386 to the insertion shape 387. The forceps 391 using the handles 396 and 397 are positioned relative to the implant 385 such that the first and second hooks 392 and 393 insert under the lower surface 17 of the bridge 15 respectively in alignment with the first and second grooves 388 and 389 while the plunger 394 is located above the upper surface 16 of the bridge 15 at the transition section 22. Once the forceps 391 are positioned, an actuation of the forceps 391, which consists of closing the handles 396 and 397 through a pivoting of the handle 397 towards the handle 396, moves the plunger 394 linearly towards the upper surface 16 of the bridge 15 such that the plunger 394 at the distal end 411 seats atop at the transition section 22. Closing of the forceps 391 continues until the seating of the plunger 394 atop the transition section 22 causes the first and second hooks 392 and 393 respectively to at least partially insert into and engage with the first and second grooves 388 and 389. Continued closing of the forceps 391 applies a force to the implant 385 that facilitates transition of the implant 385 from the natural shape 386 to the insertion shape 387. More particularly, the implant 385 via the transition section 22 mechanically deforms to store energy while also moving the bridge 15 from the natural form 34 where the first and second ends 20 and 21 reside at the first distance 36 to the insertion form 35 where the first and second ends 20 and 21 reside at the second distance 37. Moreover, the movement of the bridge 15 progresses the first and second legs 87 and 88 from the natural position 91 where the first and second legs 87 and 88 reside at the first distance 93 to the insertion position 92 where the first and second legs 87 and 88 reside at the second distance 94. After the implant 385 transitions to the insertion shape 387, the first and second hooks 392 and 393 respectively fully insert into the first and second grooves 388 and 389 and then tighten against the bridge 15. Upon the seating of the plunger 394 and the tightening of the first and second hooks 392 and 393 against the bridge 15, an engagement of the locking ratchet 398 locks the forceps 391 and prevents a release thereof from the implant 385. The locking of the forceps 391 at the plunger 394 and the first and second hooks 392 and 393 thereof with the implant 385 secures the forceps 391 with the implant 385 whereby the forceps 391 constrain the implant 385 in the insertion shape 387 and preclude the implant 385 from returning to the natural shape 386.

In accordance with the orthopedic fixation system 10, the forceps 391, when engaged with the implant 385 as previously described, retains the implant 385 in the insertion shape 387 such that the implant 385 is ready for securing with bone, bones, or bone pieces, and, in particular, with a first bone and a second bone, which are presented herein as an example. A surgeon aligns the first bone with the second bone at a fixation zone in an orientation that promotes fixation of the first bone with the second bone and a proper healing thereof. Upon alignment of the first bone with the second bone at the fixation zone, the surgeon forms a drill hole in the first bone and a drill hole in the second bone spaced apart a distance substantially equal to the second distance 94 of the first and second leg 87 and 88 of the implant 385. The surgeon using the forceps 391 then inserts the first leg 87 into the drill hole in the first bone and the second leg 88 into the drill hole in the second bone until the bridge 15 of the implant 385, which resides across the first bone and the second bone with the transition section 22 thereof located at the fixation zone, abuts the first and second bones.

In light of the affixation of the implant 385 with the first and second bones across the fixation zone, the surgeon removes the forceps 391 from the implant 385. The surgeon releases the locking ratchet 398 and actuates the forceps 391, which consists of opening the handles 396 and 397 through a pivoting of the handle 397 away from the handle 396, causing the plunger 394 to move linearly away from the upper surface 16 of the bridge 15 such that the plunger 394 at the distal end 411 releases from atop the transition section 22. After release of the plunger 394 from the bridge 15, the surgeon via the handles 396 and 397 withdraws the first and second hooks 392 and 393 respectively from the first and second grooves 388 and 389, thereby separating the forceps 391 from the implant 385. Upon the separation of the forceps 391 from the implant 385, the implant 385 attempts transition from the insertion shape 387 to the natural shape

386 whereby the implant 385 delivers the energy stored in the transition section 22 to the first bone and the second bone, resulting in the implant 385 affixing the first bone and the second bone through an application of a compressive force to the fixation zone.

The forceps 391 accordingly improve insertion of the implant 385 because the forceps 391 do not release constraint of the implant 385 until the implant 385 is affixed to the first and second bones with its transition section 22 located across the fixation zone thereof such that the forceps 391 prevent the implant 385 from prematurely delivering the energy stored therein to the first and second bones at the fixation zone thereof. Moreover, the inclusion of the first and second grooves 388 and 389 in the implant 385 improves implantation of the implant 385 because the engagement of the implant retainer 390 with the implant 385 at the first and second grooves 388 and 389 permits implanting of the implant 385 in the insertion position 387 into bone, bones, or bone pieces using the implant retainer 390 without having to tamp the implant 385 after removal of the implant retainer 390.

Figure 35:
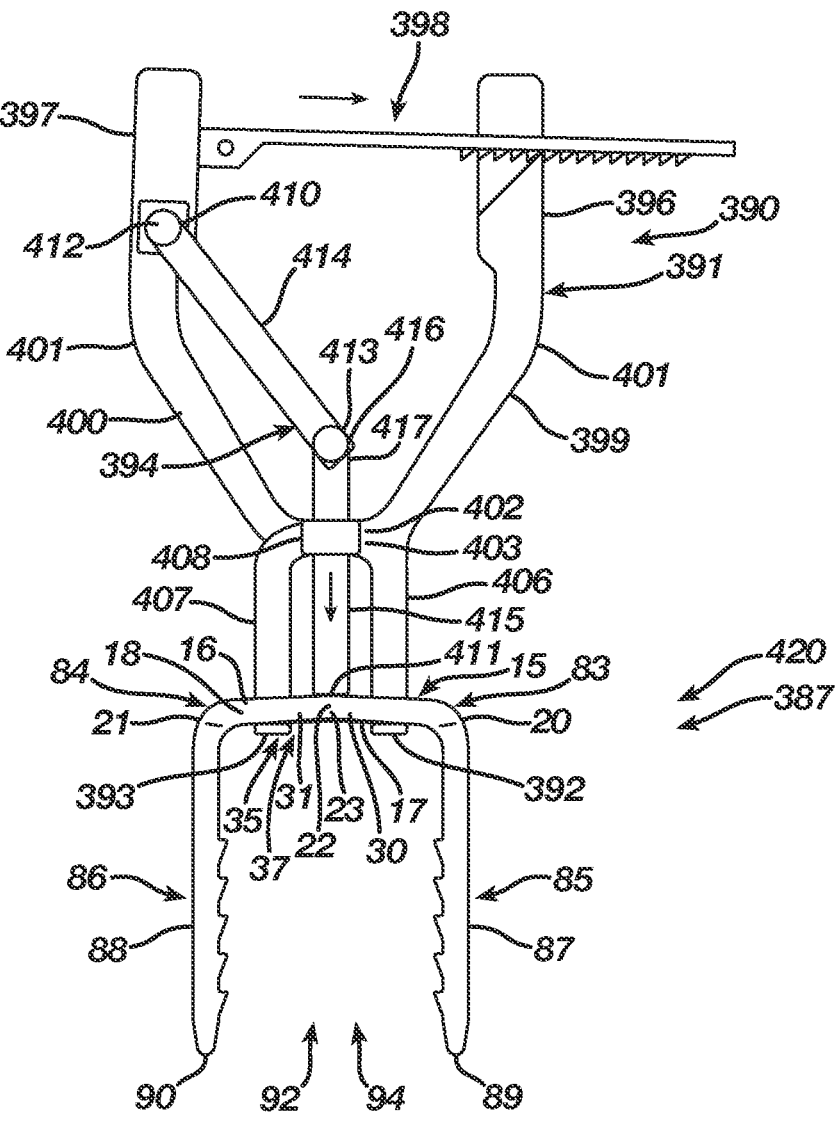
FIG. 35 is a front view illustrating the implant retainer according to the ninth embodiment and an orthopedic implant according to an alternative of the ninth embodiment in an insertion shape forming the orthopedic fixation system.

FIG. 35 illustrates the orthopedic fixation system 10 including an orthopedic implant 420 according to an alternative of the ninth embodiment and the implant retainer 390 according to the ninth embodiment. The implant 420 is substantially similar in design and operation relative to the implant 385 according to the ninth embodiment and the orthopedic implant 80 according to the fourth embodiment such that, for the sake of brevity, only differences therebetween will be described herein. Moreover, one of ordinary skill in the art will recognize that like parts of the implant 420 labeled with like numerals of the implant 385 and the implant 80 incorporate a design and function as previously set forth in the detailed description of the implant 385 according to the ninth embodiment and the implant 80 according to the fourth embodiment. While the implant 385 includes the first and second grooves 388 and 389 configured to engage with the first and second hooks 392 and 393 of the implant retainer 390, the implant 420 does not include first and second grooves cut into the lower surface 17 of the bridge 15. The implant retainer 390 engages with and constrains the implant 420 in the insertion shape 387 substantially similar as previously described with respect to the implant 385, except that the first and second hooks 392 and 393 abut the lower surface 17 of the implant 420 without insertion into first and second grooves. Furthermore, implantation of the implant 420 into bone, bones, or bone pieces using the implant retainer 390 is substantially similar as previously described with respect to the implant 385, except that the implant 420 must be tamped after removal of the implant retainer 390.

It should be understood that orthopedic implant 11 according to the first embodiment may be modified to function with the implant retainer 390 according to the ninth embodiment. In accordance therewith, the implant 11 may be modified by eliminating the first and second apertures 28 and 29 and the catches 32 and 33 thereof while including the first and second grooves 388 and 389 as previously described with respect to the implant 385 such that the implant retainer 390 is engageable with the modified implant 11 in order to constrain the modified implant 11 in the insertion shape 13. The implant retainer 390 therefore engages with and constrains the modified implant 11 in the insertion shape 13 substantially, completely identical to the implant 385 as previously described. Implantation of the modified implant 11 into bone, bones, or bone pieces using the implant retainer 390 is substantially similar as previously described with respect to the implant 385, except that the modified implant 11, as previously described with respect to the implant 11 according to the first embodiment, secures with the bone, bones, or bone pieces using anchoring members in the form of screws prior to the removal of the implant retainer 390. The implant retainer 390 accordingly improves insertion of the modified implant 11 because the implant retainer 390 does not release constraint of the modified implant 11 until the modified implant 11 is affixed to the first and second bones with its transition section 22 located across the fixation zone thereof such that the implant retainer 390 prevents the modified implant 11 from prematurely delivering the energy stored therein to the first and second bones at the fixation zone thereof.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system, comprising:
an implant transitionable between a natural shape and an insertion shape whereby a transition of the implant from the natural shape to the insertion shape stores deliverable energy and a transition of the implant from the insertion shape to the natural shape delivers stored energy, the implant, comprising:
a bridge with a first end and a second end,
a transition section disposed in the bridge, whereby the transition section deforms to move the implant between the natural shape and the insertion shape,
a first anchoring segment disposed at the first end of the bridge, the first anchoring segment comprising an opening configured to receive therethrough a first fixation member,
a second anchoring segment disposed at the second end of the bridge, the second anchoring segment comprising an opening configured to receive therethrough a second fixation member,
a first post protruding from the bridge adjacent the transition section at a first side thereof, the first post including an opening therethrough,
a second post protruding from the bridge adjacent the transition section at a second side, the second post including an opening therethrough, and
the first post and the second post protruding from the bridge, whereby, when the implant resides in the insertion shape, the opening of the first post and the opening of the second post align; and
an implant retainer configured to insert in the opening of the first post and the opening of the second post when the implant resides in the insertion shape, whereby the implant retainer interconnects the first post and second post while spanning the transition section, thereby constraining the implant in the insertion shape.

2. The orthopedic fixation system of claim 1, the first post and the second post each being removable from the bridge.

3. The orthopedic fixation system of claim 1, the implant retainer, comprising a pin being insertable in the opening of the first post and the opening of the second post when the implant resides in the insertion shape, whereby the pin interconnects the first post and second post while spanning the transition section, thereby constraining the implant in the insertion shape.

4. The orthopedic fixation system of claim 3, wherein a removal of the pin from the opening through the first post or the opening through the second post allows attempted transition of the implant from the insertion shape toward the natural shape.

5. The orthopedic fixation system of claim 3, wherein a cutting of the pin prior to a removal of the pin from the openings through the first post and the second post allows attempted transition of the implant from the insertion shape toward the natural shape.

6. The orthopedic fixation system of claim 3, the first post and the second post each being removable from the bridge.

7. The orthopedic fixation system of claim 3, the openings through the first and second posts each comprising a bore, the pin being insertable through the bore of the first post and the bore of the second post when the implant resides in the insertion shape, whereby the pin interconnects the first post and second post while spanning the transition section, thereby constraining the implant in the insertion shape and preventing the implant from returning to the natural shape.

8. The orthopedic fixation system of claim 1, comprising: the implant, comprising:
the transition section being a first transition section located at a center section of the bridge,
a second transition section between the first transition section and the first anchoring segment,
a third transition section between the first transition section and the second anchoring segment, whereby the first transition section, the second transition section, and the third transition section deform to move the orthopedic implant between the natural shape and the insertion shape,
the first post protruding from the bridge between the first transition section and the second transition section,
the second post protruding from the bridge between the first transition section and the third transition section,
a third post protruding from the bridge between the second transition section and the first anchoring segment, the third post including an opening therethrough,
a fourth post protruding from the bridge between the third transition section and the second anchoring segment, the fourth post including an opening therethrough, and
the first post, the second post, the third post, and the fourth post protruding from the bridge, whereby, when the implant resides in the insertion shape, the openings of the first post, the second post, the third post, and the fourth post align; and
the implant retainer being configured to insert in the openings of the first post, the second post, the third post, and the fourth post when the implant resides in the insertion shape, whereby the implant retainer interconnects the first post, the second post, the third post, and the fourth post while spanning the first transition section, the second transition section, and the third transition section, thereby constraining the implant in the insertion shape.

9. The orthopedic fixation system of claim 8, wherein the first transition section, the second transition section, and the third transition section produce a continuous curve in the implant when the implant resides in the natural shape.

10. The orthopedic fixation system of claim 8, the first post, the second post, the third post, and the fourth post each being removable from the bridge.

11. The orthopedic fixation system of claim 8, the implant retainer, comprising a pin being insertable in the openings of the first post, the second post, the third post, and the fourth post when the implant resides in the insertion shape, whereby the pin interconnects the first post, the second post, the third post, and the fourth post while spanning the first transition section, the second transition section, and the third transition section, thereby constraining the implant in the insertion shape.

12. The orthopedic fixation system of claim 11, wherein a removal of the pin from the openings through the fourth post, the second post, and the first post or a removal of the pin from the openings through the third post, the first post, and the second post allows attempted transition of the implant from the insertion shape toward the natural shape.

13. The orthopedic fixation system of claim 11, the openings through the first post, the second post, the third post, and the fourth post each comprising a bore, the pin being insertable through the bores of the first post, the second post, the third post, and the fourth post when the implant resides in the insertion shape, whereby the pin interconnects the first post, the second post, the third post, and the fourth post while spanning the first transition section, the second transition section, and the third transition section, thereby constraining the implant in the insertion shape and preventing the implant from returning to the natural shape.

14. The orthopedic fixation system of claim 11, wherein:
a removal of the pin from the opening through the fourth post allows attempted transition of the implant from the insertion shape toward a first intermediate shape;
a removal of the pin from the opening through the second post allows attempted transition of the implant from the first intermediate shape toward a second intermediate shape; and
a removal of the pin from the opening through the first post allows attempted transition of the implant from the second intermediate shape toward the natural shape.

15. The orthopedic fixation system of claim 11, wherein:
a removal of the pin from the opening through the third post allows attempted transition of the implant from the insertion shape toward a first intermediate shape;
a removal of the pin from the opening through the first post allows attempted transition of the implant from the first intermediate shape toward a second intermediate shape; and
a removal of the pin from the opening through the second post allows attempted transition of the implant from the second intermediate shape toward the natural shape.

16. An orthopedic fixation system, comprising:
an implant transitionable between a natural shape and an insertion shape whereby a transition of the implant from the natural shape to the insertion shape stores deliverable energy and a transition of the implant from the insertion shape to the natural shape delivers stored energy, the implant, comprising:
a bridge with a first end and a second end,
a transition section disposed in the bridge, whereby the transition section deforms to move the implant between the natural shape and the insertion shape,
a first anchoring segment disposed at the first end of the bridge,
a second anchoring segment disposed at the second end of the bridge,

a first post protruding from the bridge adjacent the transition section at a first side thereof, the first post including an opening therethrough,
a second post protruding from the bridge adjacent the transition section at a second side, the second post including an opening therethrough, and
the first post and the second post protruding from the bridge, whereby, when the implant resides in the insertion shape, the opening of the first post and the opening of the second post align;
an implant retainer configured to insert in the opening of the first post and the opening of the second post when the implant resides in the insertion shape, whereby the implant retainer interconnects the first post and second post while spanning the transition section, thereby constraining the implant in the insertion shape;
the implant retainer, comprising a pin being insertable in the opening of the first post and the opening of the second post when the implant resides in the insertion shape, whereby the pin interconnects the first post and second post while spanning the transition section, thereby constraining the implant in the insertion shape; and
the first post and the second post each being removable from the bridge, wherein a pivoting of the first post removes the pin from the opening through the second post or a pivoting of the second post removes the pin from the opening through the first post thereby allowing attempted transition of the implant from the insertion shape toward the natural shape.

17. An orthopedic fixation system, comprising:
an implant transitionable between a natural shape and an insertion shape whereby a transition of the implant from the natural shape to the insertion shape stores deliverable energy and a transition of the implant from the insertion shape to the natural shape delivers stored energy, the implant, comprising:
a bridge with a first end and a second end,
a first anchoring segment disposed at the first end of the bridge,
a second anchoring segment disposed at the second end of the bridge,
a first transition section, a second transition section, and a third transition section disposed along the bridge between the first anchoring segment and the second anchoring segment, whereby the first transition section, the second transition section, and the third transition section deform to move the implant between the natural shape and the insertion shape,
a first post protruding from the bridge between the first anchoring segment and the first transition section, the first post including an opening therethrough,
a second post protruding from the bridge between the first transition section and the second transition section, the second post including an opening therethrough,
a third post protruding from the bridge between the second transition section and the third transition section, the third post including an opening therethrough,
a fourth post protruding from the bridge between the third transition section and the second anchoring segment, the fourth post including an opening therethrough, and
the first post, the second post, the third post, and the fourth post protruding from the bridge, whereby, when the implant resides in the insertion shape, the openings of the first post, the second post, the third post, and the fourth post align; and an implant retainer being configured to insert in the openings of the first post, the second post, the third post, and the fourth post when the implant resides in the insertion shape, whereby the implant retainer interconnects the first post, the second post, the third post, and the fourth post while spanning the first transition section, the second transition section, and the third transition section, thereby constraining the implant in the insertion shape.

18. The orthopedic fixation system of claim 17, wherein the first transition section, the second transition section, and the third transition section produce a continuous curve in the implant when the implant resides in the natural shape.

19. The orthopedic fixation system of claim 17, the first post, the second post, the third post, and the fourth post each being removable from the bridge.

20. The orthopedic fixation system of claim 17, the implant retainer, comprising a pin being insertable in the openings of the first post, the second post, the third post, and the fourth post when the implant resides in the insertion shape, whereby the pin interconnects the first post, the second post, the third post, and the fourth post while spanning the first transition section, the second transition section, and the third transition section, thereby constraining the implant in the insertion shape.

21. The orthopedic fixation system of claim 20, wherein a removal of the pin from the openings through the fourth post, the third post, and the second post allows attempted transition of the implant from the insertion shape toward the natural shape.

22. The orthopedic fixation system of claim 20, the openings through the first post, the second post, the third post, and the fourth post each comprising a bore, the pin being insertable through the bores of the first post, the second post, the third post, and the fourth post when the implant resides in the insertion shape, whereby the pin interconnects the first post, the second post, the third post, and the fourth post while spanning the first transition section, the second transition section, and the third transition section, thereby constraining the implant in the insertion shape and preventing the implant from returning to the natural shape.

23. The orthopedic fixation system of claim 20, wherein:

a removal of the pin from the opening through the fourth post allows attempted transition of the implant from the insertion shape toward a first intermediate shape;

a removal of the pin from the opening through the third post allows attempted transition of the implant from the first intermediate shape toward a second intermediate shape; and a removal of the pin from the opening through the second post allows attempted transition of the implant from the second intermediate shape toward the natural shape.

* * * * *